United States Patent [19]

Karanewsky

[11] Patent Number: 5,194,634
[45] Date of Patent: Mar. 16, 1993

[54] DIHYDROXYHEPTANOIC ACIDS CONTAINING AN OXABICYCLOHEPTANE NUCLEUS USEFUL AS ANTIHYPERCHOLESTEROLEMIC AGENTS

[75] Inventor: Donald S. Karanewsky, Robbinsville, N.J.

[73] Assignee: E. R. Squibb & Sons, Inc., Princeton, N.J.

[21] Appl. No.: 921,781

[22] Filed: Jul. 30, 1992

Related U.S. Application Data

[62] Division of Ser. No. 851,386, Mar. 12, 1992, Pat. No. 5,157,134.

[51] Int. Cl.$^5$ ............................................. C07D 309/12
[52] U.S. Cl. ............................................. 549/292
[58] Field of Search ................................. 549/292

[56] References Cited

U.S. PATENT DOCUMENTS

| | | | |
|---|---|---|---|
| 4,710,513 | 12/1987 | Willard et al. | 549/292 |
| 4,812,583 | 3/1989 | Commons et al. | 549/292 |
| 4,855,481 | 8/1989 | Guindon et al. | 549/292 |

Primary Examiner—Marianne M. Cintins
Assistant Examiner—John Peabody
Attorney, Agent, or Firm—Burton Rodney

[57] ABSTRACT

Dihydroxyheptanoic acids containing an oxabicyloheptane nucleus are provided which have the structure

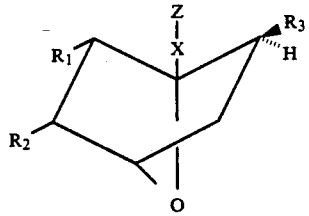

including all stereoisomers thereof, wherein Z is

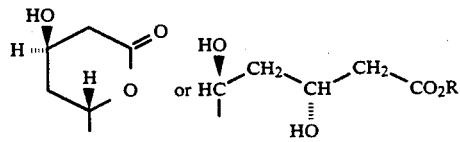

and X, $R_1$, $R_2$ and $R_3$ are as defined herein.

12 Claims, No Drawings

DIHYDROXYHEPTANOIC ACIDS CONTAINING AN OXABICYCLOHEPTANE NUCLEUS USEFUL AS ANTIHYPERCHOLESTEROLEMIC AGENTS

This is a division of application Ser. No. 851,386, filed Mar. 12, 1992, now U.S. Pat. No. 5,157,134.

FIELD OF THE INVENTION

The present invention relates to dihydroxyheptanoic acids containing an oxabicycloheptane nucleus which are HMG CoA reductase inhibitors and thus are useful as antihypercholesterolemic agents.

DESCRIPTION OF THE INVENTION

In accordance with the present invention, compounds are provided having the structure

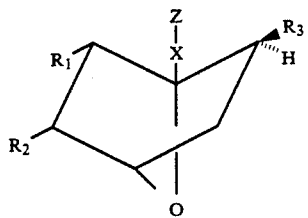

and include all stereoisomers thereof, wherein Z is

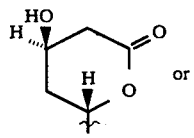

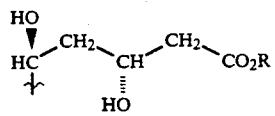

X is —$CH_2CH_2$— or —CH=CH—;
R is an alkali metal (such as Li, Na or K), lower alkyl or H;
$R_1$ is alkyl, arylalkyl, alkanoyloxyalkyl, arylalkyloxyalkyl, alkylaminocarbonyl, dialkylaminocarbonyl, alkanoylaminoalkyl, alkanoyl(alkyl)aminoalkyl or arylalkyl(alkyl)aminocarbonyl;
$R_2$ is H, alkyl, aralkyl, alkoxyalkyl, aralkoxyalkyl, hydroxyalkyl or alkanoyloxyalkyl;
$R_3$ is H, alkyl or aralkyl.

Thus the compounds of the invention include the following types of compounds.

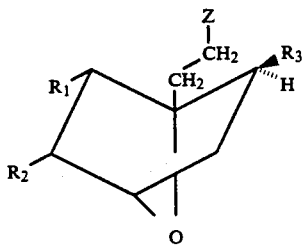

and

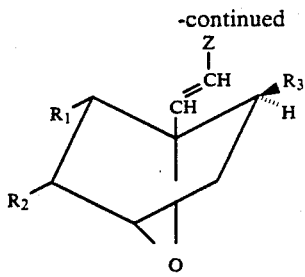

Preferred are compounds of structure IA wherein $R_1$ is branched alkanoyloxyalkyl or branched alkanoyl(alkyl)aminoalkyl, $R_2$ is arylalkyloxyalkyl, and $R_3$ is alkyl. Most preferred are compounds of structure IA wherein $R_1$ is

$R_2$ is $C_6H_5CH_2OCH_2$—, and $R_3$ is $CH_3$—; and Z is

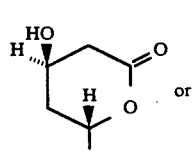

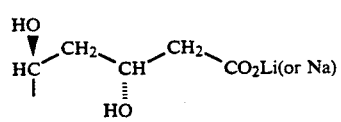

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, alkoxy, aryl, alkylaryl, haloaryl, cycloalkyl, alkylcycloalkyl, hydroxy, alkoxycarbonyl, alkanoyloxy, aroyloxy, alkylthio, alkylsulfinyl, alkylsulfonyl, arylthio, arylsulfinyl and/or arylsulfonyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 of the following groups: halogen, lower alkoxy, lower alkyl, hydroxy, lower alkoxycarbonyl, lower alkanoyl, aroyl, aryl, alkylthio, alkylsulfinyl, alkylsulfonyl, cycloalkylthio, cycloalkylsulfinyl, cycloalkylsulfonyl, arylthio and/or oxo.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 of the following groups, lower alkyl, halogen (Cl, Br, F or $CF_3$), lower alkoxy, aryl, nitro, and/or cyano.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine, with chlorine being preferred.

The term "lower alkenyl" as used herein refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The terms "alkanoyl" and "aroyl" refer to a lower alkyl group linked to a carbonyl group or an aryl group linked to a carbonyl group.

The term "haloalkyl" as used herein refers to any of the lower alkyl groups defined above substituted with a halogen as defined above, for example $CH_2F$, $CF_3$ and the like.

The term "metal ion" refers to alkali metal ions such as sodium, potassium or lithium and alkaline earth metal ions such as magnesium and calcium.

Compounds of the invention wherein X is —CH═CH— may be prepared by subjecting aldehyde X

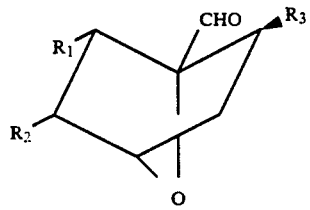

to a Horner-Emmons reaction wherein aldehyde X is treated with a homochiral phosphonate XI

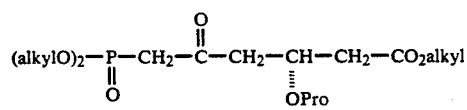

wherein Pro represents a protecting group such as t-butyldimethylsilyl, in the presence of a lithium salt such as lithium chloride and an amine base, such as 1,8-diazabicyclo[5.4.0]undec-7-ene (DBU) or isopropyldiethylamine, and an organic solvent such as acetonitrile, under an inert atmosphere such as argon, to form the protected olefinated compound XII

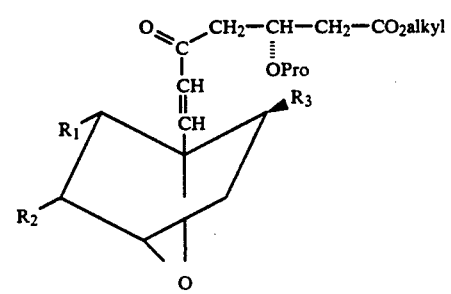

The chiral ketophosphonate XI is prepared as described in U.S. Pat. No. 4,804,770 and is employed in a molar ratio to aldehyde X of within the range of from about 1:1 to about 2:1.

The hydroxyl in olefin XII may be liberated by treating with fluoride (for example, HF, in an inert organic solvent such as acetonitrile or tetrabutylammonium fluoride in the presence of acetic acid) to form the ketone XIII

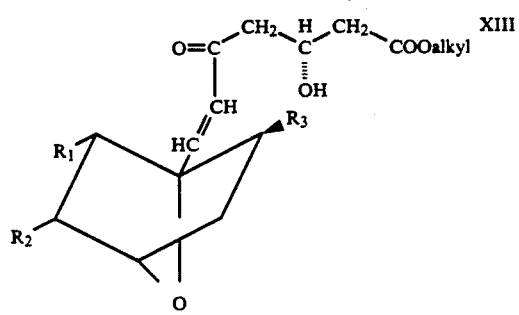

Next, the ketone in XIII is reduced by treating with a reducing agent such as sodium borohydride, in the presence of triethylborane, and an inert organic solvent such as tetrahydrofuran, and an alcohol such as methanol to form the 1,3-diol of the invention XIV

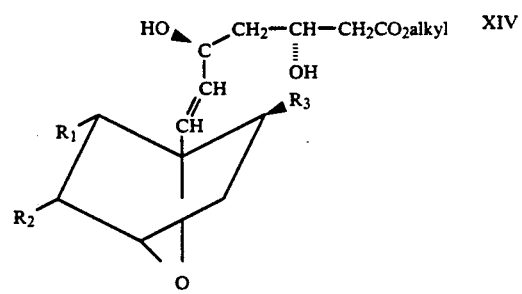

Alcohol XIV may then be hydrolyzed by treating XIV with aqueous alkali metal base such as sodium hydroxide or lithium hydroxide, in the presence of a suitable solvent such as dioxane, acetonitrile or tetrahydrofuran, to form the compound XIV of the invention XV

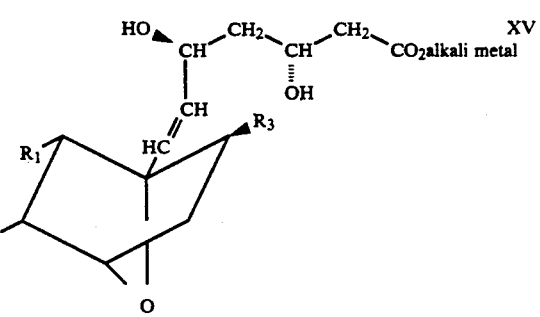

Compound XV may be converted to the corresponding acid XVI by treating XV with mild aqueous acid such as potassium bisulfate to form compound of the invention XVI

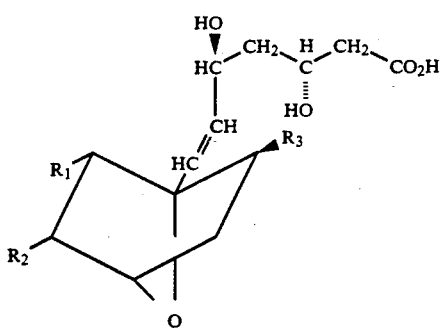

XVI

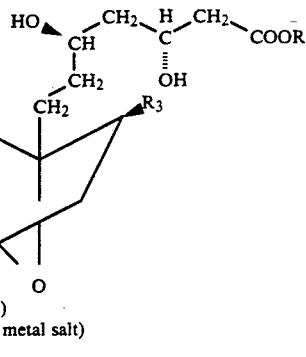

XIX (R = alkyl)
XX (R = alkali metal salt)
XXI (R = H)

Compounds of the invention wherein X is $CH_2-CH_2$ may be prepared by reducing the ketone XII by treating XII with hydrogen in the presence of a hydrogenation catalyst such as Pt/C, or Pd/C in the presence of an organic solvent, such as methanol, ethanol or ethyl acetate to form the corresponding saturated ketone XVII which may be hydrolyzed to the corresponding alkali metal salt XX and acid XXI of the invention and converted to the corresponding lactone of the invention.

The acids XVI and XXI may be converted to the corresponding lactone XXII or XXIII by treating acid XVI or XXI with a catalytic amount of trifluoroacetic acid at ambient temperature in an organic solvent such as ethyl acetate to form lactone XXII or XXIII.

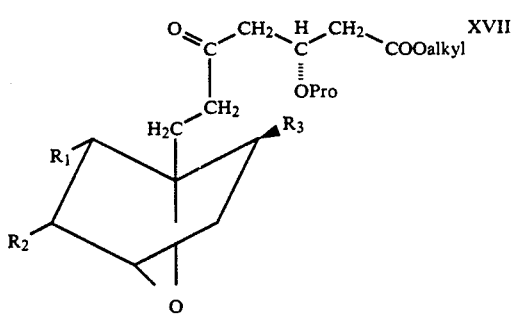

XVII

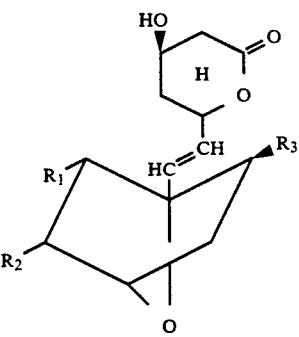

XXII which is then deprotected using deprotecting procedures described hereinbefore to remove the protecting group Pro and form the corresponding alcohol XVIII

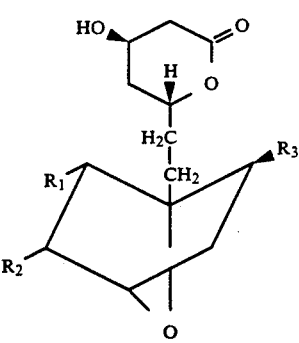

XXIII

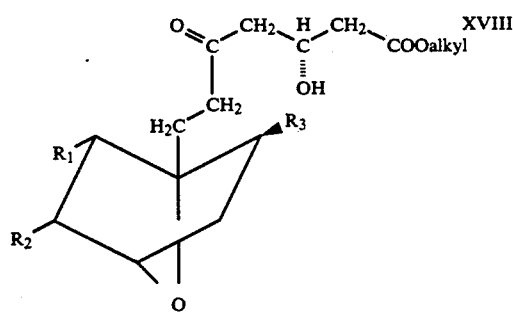

XVIII

Alcohol XVIII is then reduced employing procedures as described with respect to the reduction of XIII, to form the diol XIX Aldehyde starting material X wherein $R_1$ is $R_4CH_2CH_2-$ wherein $R_4$ is alkyl or aryl may be prepared starting with alcohol XX

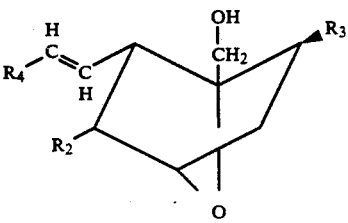

XX which is reduced by treatment with hydrogen in the presence of a catalyst such as palladium on charcoal and an alcohol solvent such as methanol and oxidized with Dess-Martin Periodinane or Swern reagent (oxalylchloride dimethylsulfoxide, trialkylamine) in methylene chloride to form the aldehyde XA

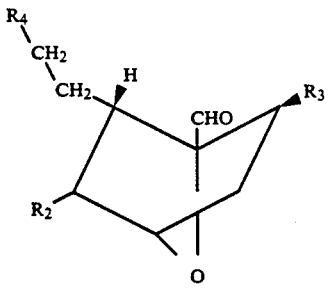
XA

Aldehyde starting material X wherein $R_1$ is

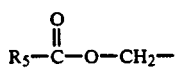

may be prepared from alcohol XX which is treated with amine base such as imidazole, triethylamine, ethyldiisopropylamine or N,N-dimethylaniline and then with a silyl chloride protecting agent (ProCl) such as tertiary-butyldimethylsilyl chloride, tertiary-butyldiphenylsilyl chloride, triethylsilyl chloride or phenyldimethylsilyl chloride, and an appropriate catalyst such as 4-(N,N-dimethylamino)pyridine (DMAP), for a period of from about 8 to about 24 hours, preferably from about 12 to about 16 hours, to form the protected compound which is treated with ozone followed by dimethylsulfide in an alcohol solvent such as methanol. The resulting crude product is treated under an inert atmosphere such as argon, with a reducing agent such as $LiAl(Ot-C_4H_9)_3H$, to form the protected reduced compound XXV

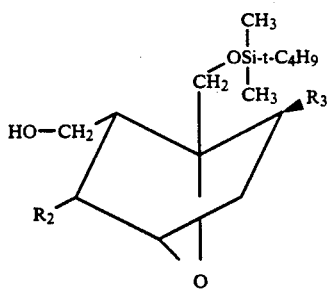
XXV

The crude product XXV is then acylated by treating same with an acylating agent of the structure XXVI

      XXVI (wherein $R_5$ is alkyl or aryl) employing a molar ratio of XXV:XXVI of within the range of from about 1:1 to about 1:2 in the presence of base such as pyridine and 4-(N,N-dimethylamino)pyridine (DMAP), under an inert atmosphere such as argon, at a temperature of from about 0° to about 25° C., for a period of from about 8 to about 24 hours, to form ester XXVII.

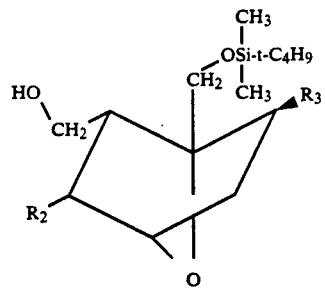
XXVII

Ester XXVII is made to undergo desilylation by treating XXVII under an inert atmosphere such as argon, with a desilylating agent such as HF in acetonitrile or $(n-C_4H_9)_4NF$ in THF to form the corresponding alcohol which is then oxidized via Dess-Martin periodinane by admixing a solution of Dess-Martin periodinane in an inert organic solvent such as methylene chloride, under an inert atmosphere such as argon, with t-butanol and a solution of the above alcohol in an inert organic solvent such as methylene chloride, to form aldehyde XXX

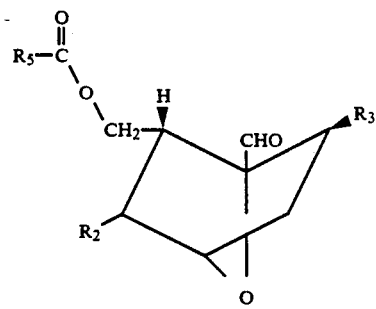
XXX

Other starting aldehydes may be prepared according to the following reaction sequences.

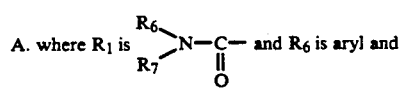

$R_7$ is alkyl, aralkyl or aryl

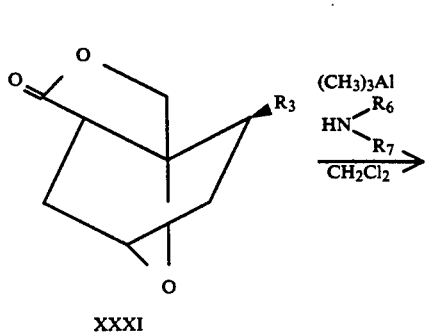
XXXI

-continued

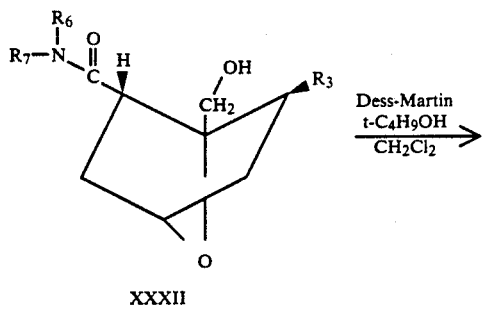

XXXII

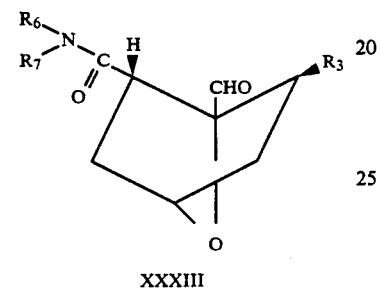

XXXIII

B. Where $R_1$ is $\underset{R_7}{\overset{R_6}{N}}-CH_2-$

XXXII $\xrightarrow{\text{LiAlH}_4}{\text{THF}}$

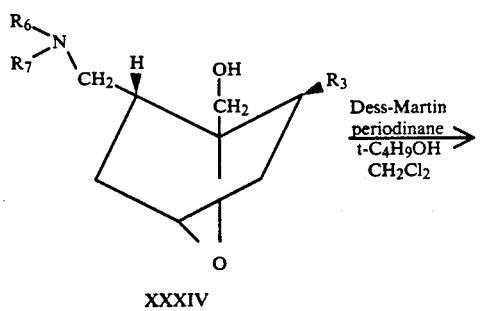

XXXIV

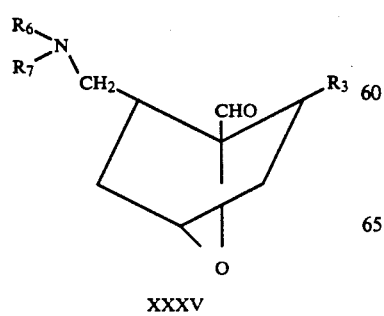

XXXV

-continued

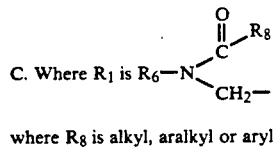

C. Where $R_1$ is $R_6-\underset{\underset{CH_2-}{|}}{\overset{\overset{O}{\|}}{N}}-\overset{O}{\overset{\|}{C}}-R_8$ where $R_8$ is alkyl, aralkyl or aryl XXXIV $\xrightarrow[\text{CH}_3\text{OH}]{\text{Reduction} \atop \text{H}_2, \text{Pd}-\text{C}}$ ($R_7 = CH_2C_6H_5$)

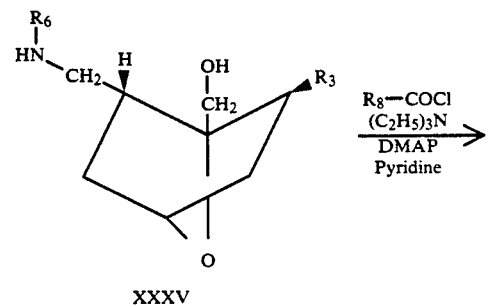

XXXV

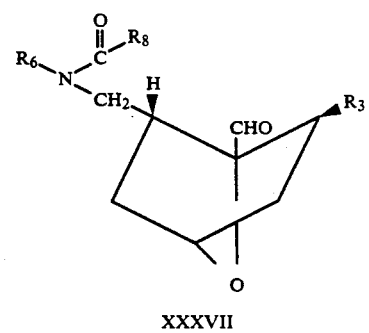

XXXVI

XXXVII

SCHEME 1
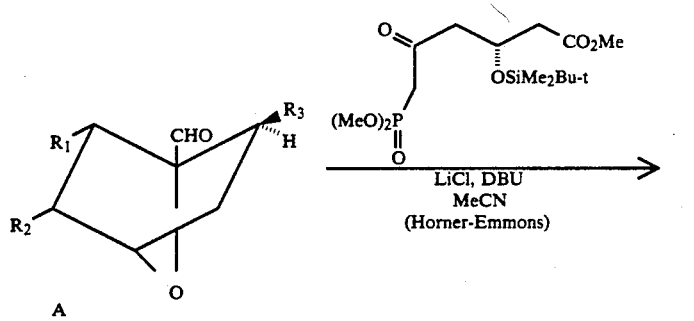
A
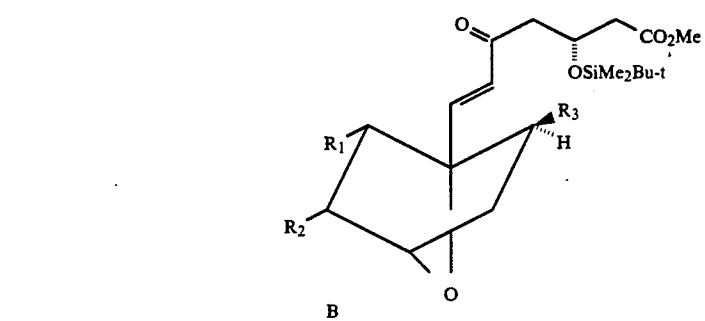
B
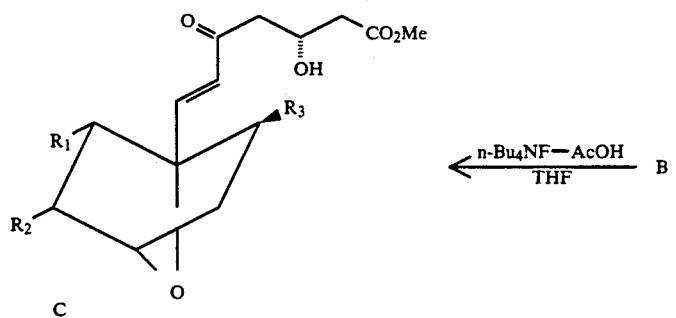
C
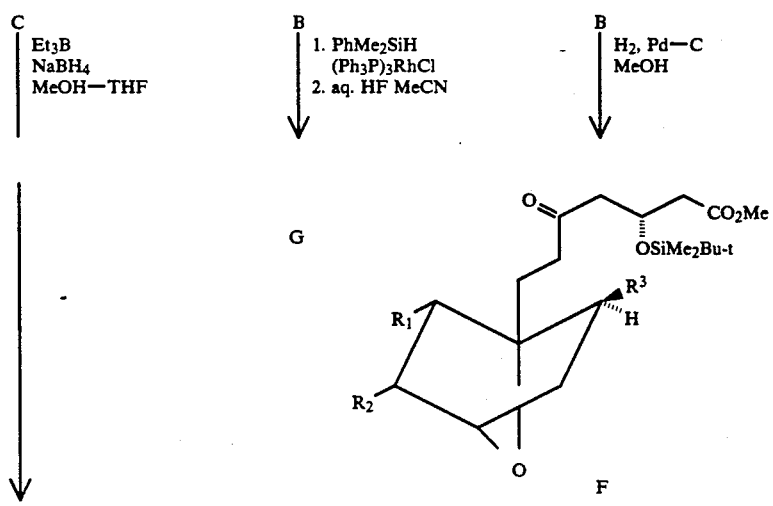

-continued
SCHEME 1
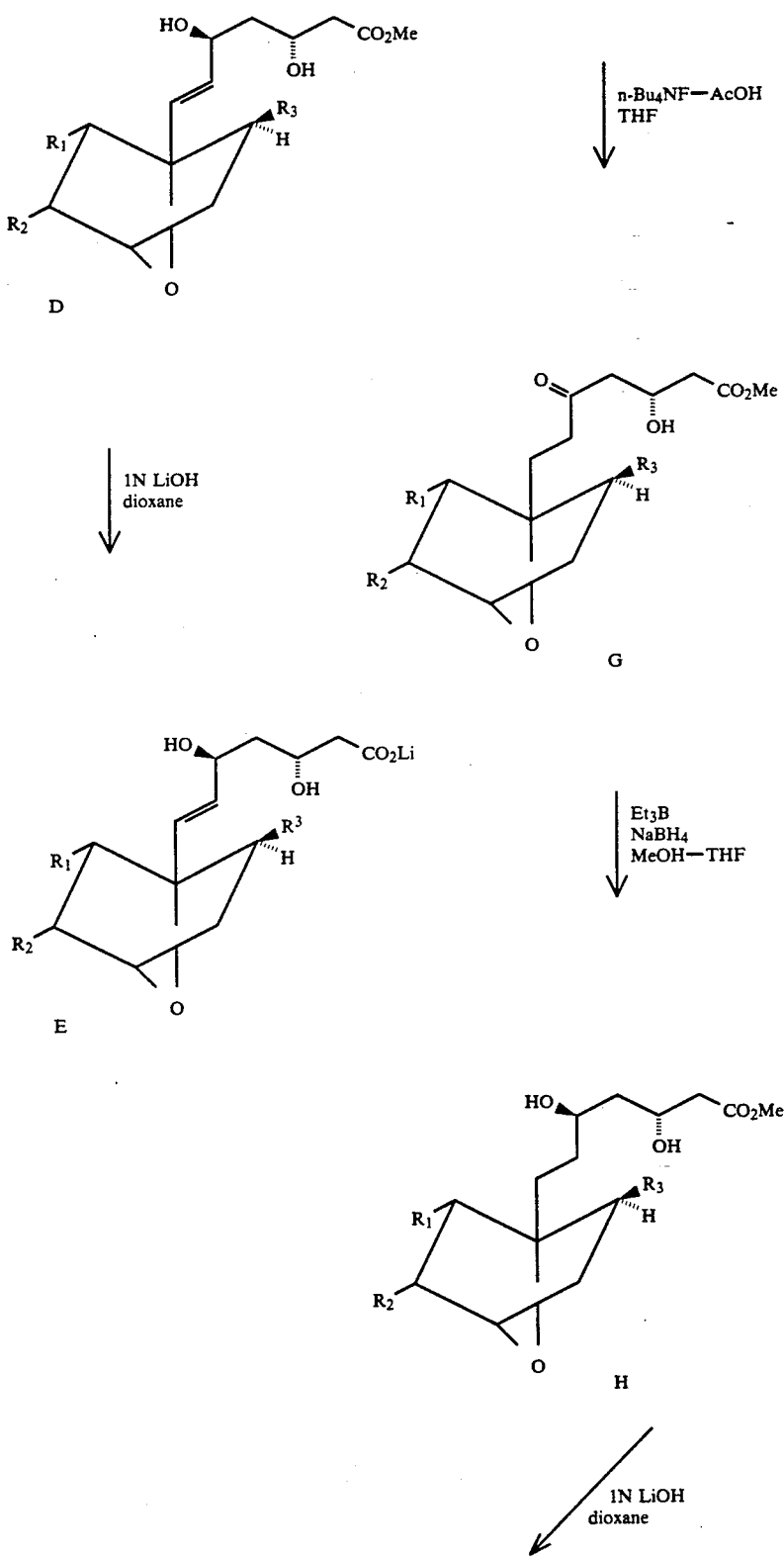

SCHEME 1
-continued
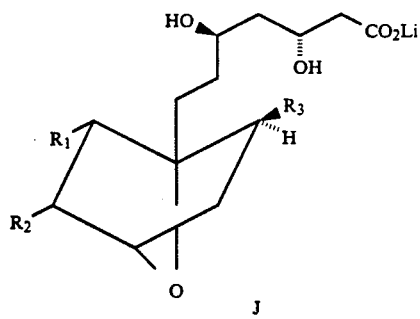
J
SCHEME 2
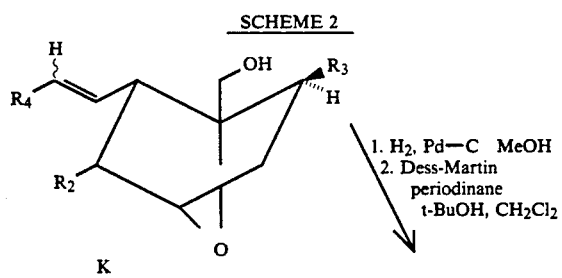
-continued
SCHEME 2
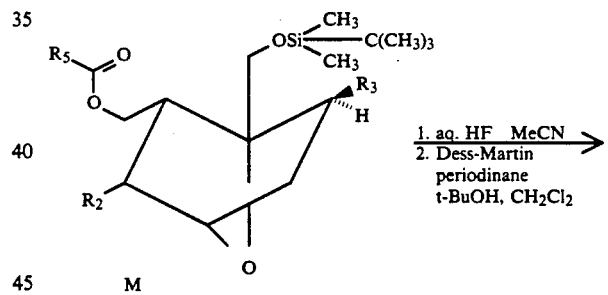
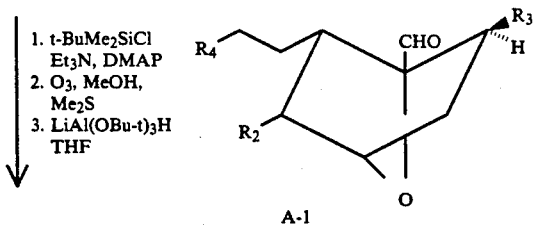
A-1
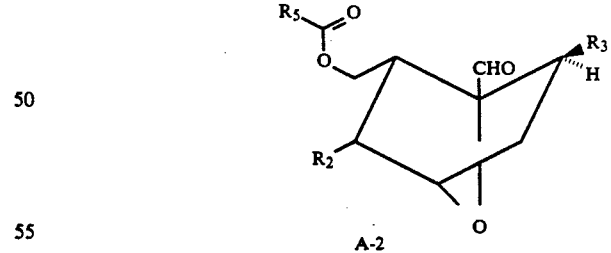
A-2
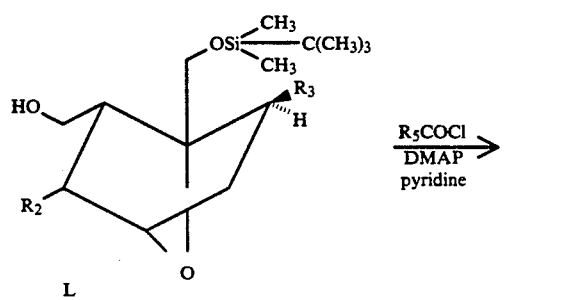
L

SCHEME 3
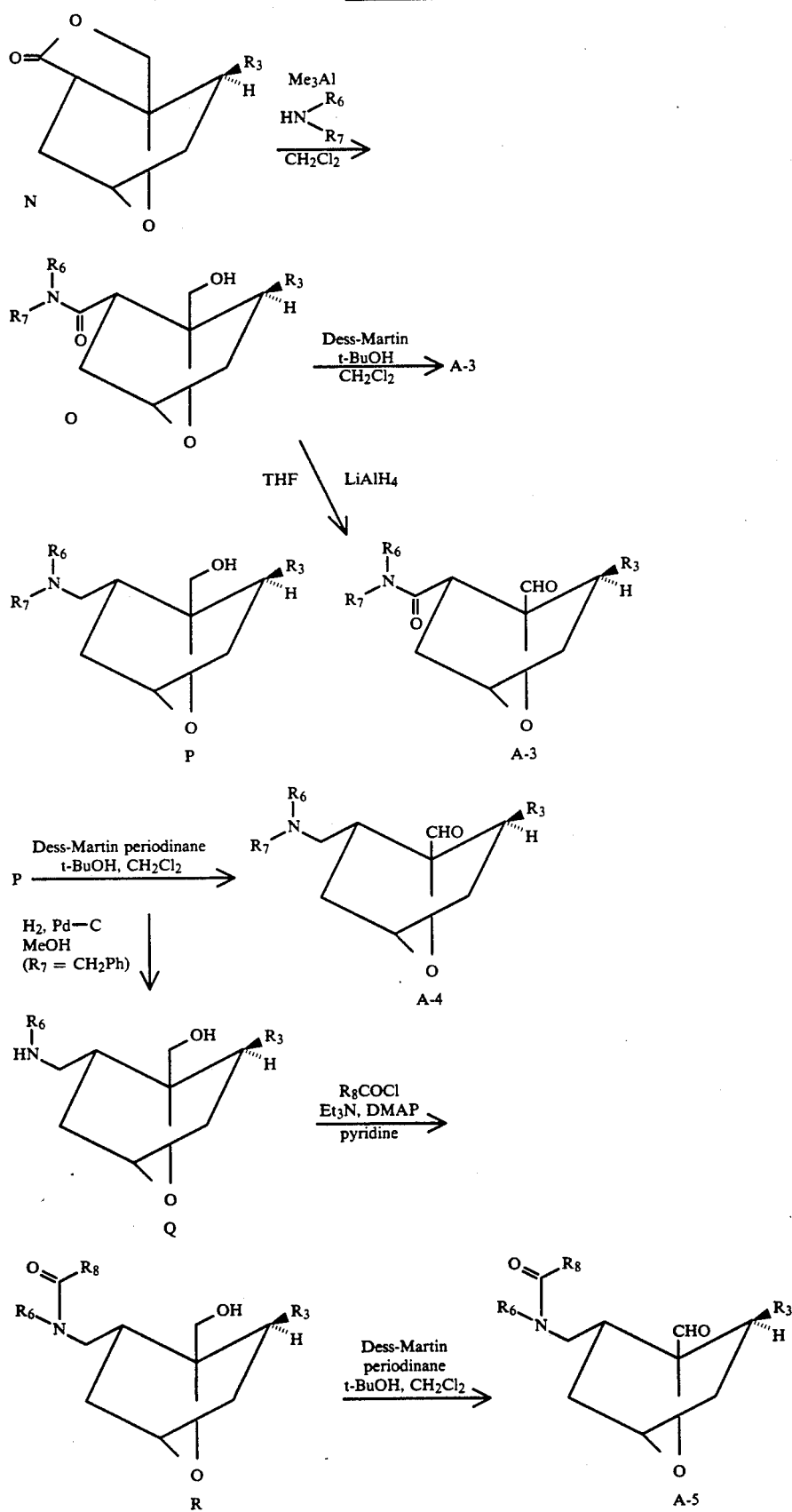

-continued
Scheme A.
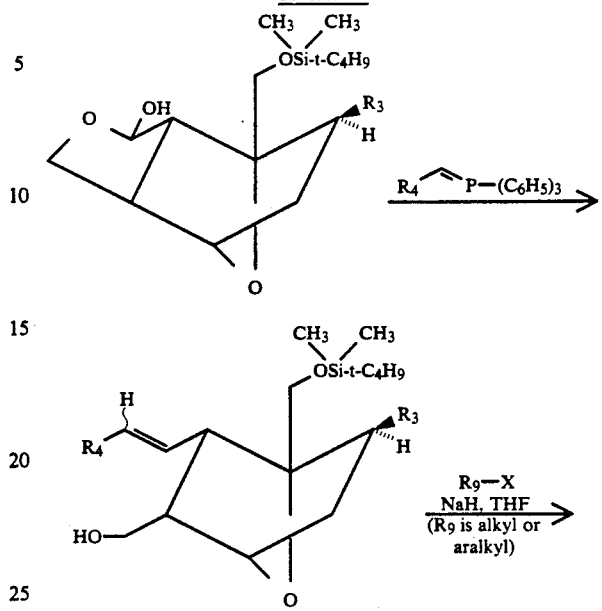
The starting compound XX may be prepared employing the following reactions.
Scheme A.
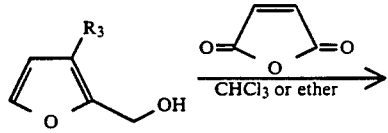
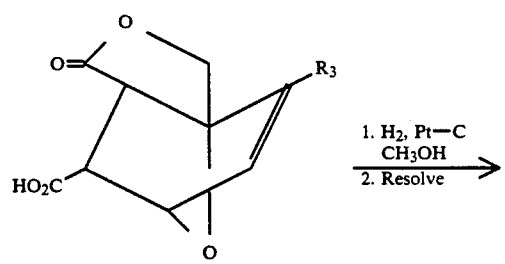
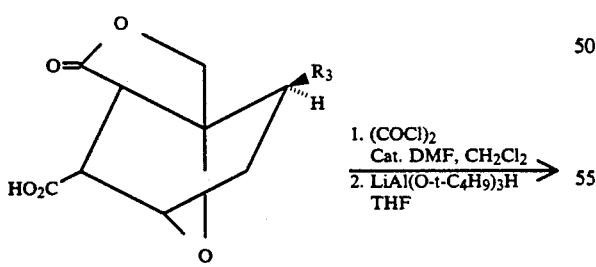
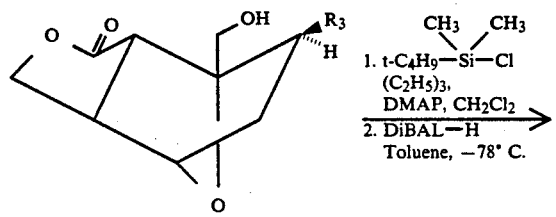
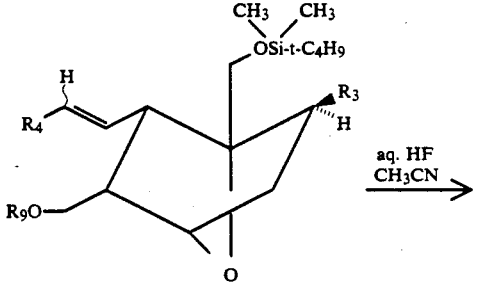
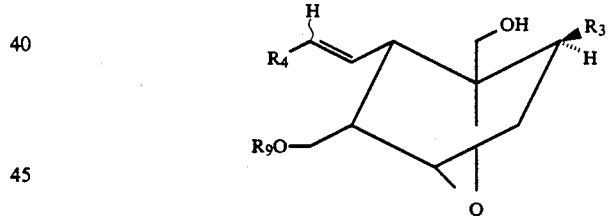
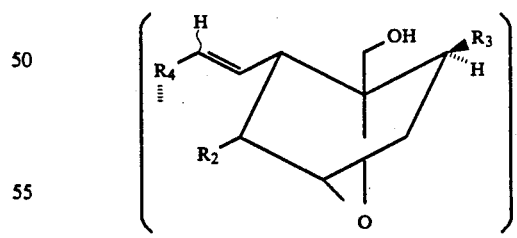
Scheme B. ($R_2$ = H only)
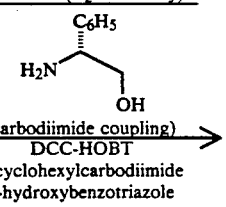

-continued
Scheme B. ($R_2$ = H only)

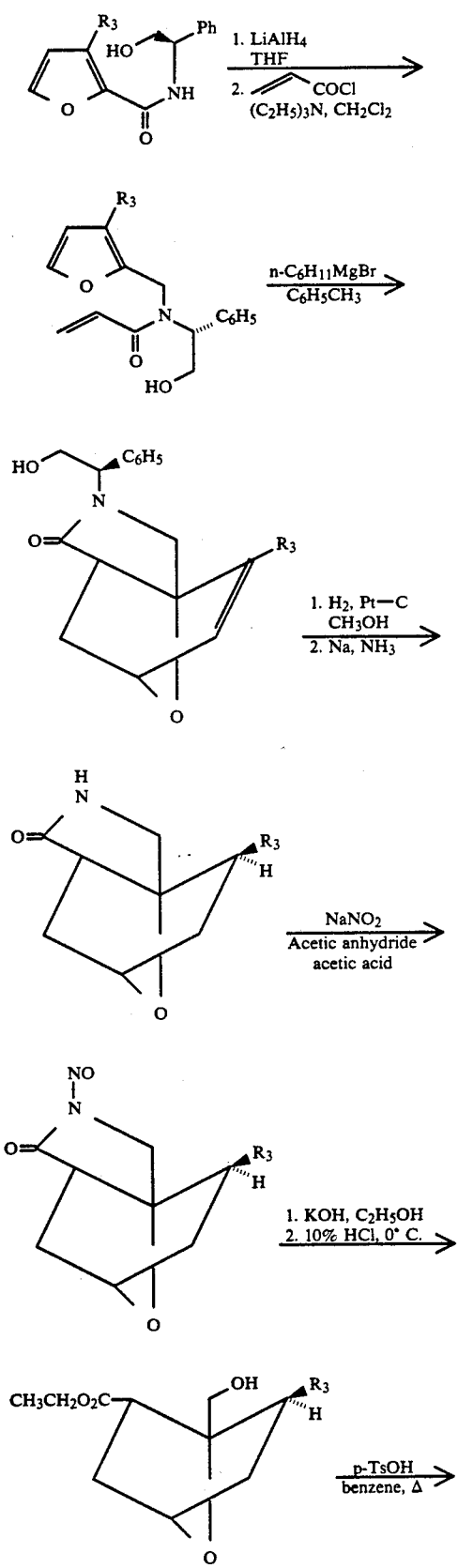

-continued
Scheme B. ($R_2$ = H only)

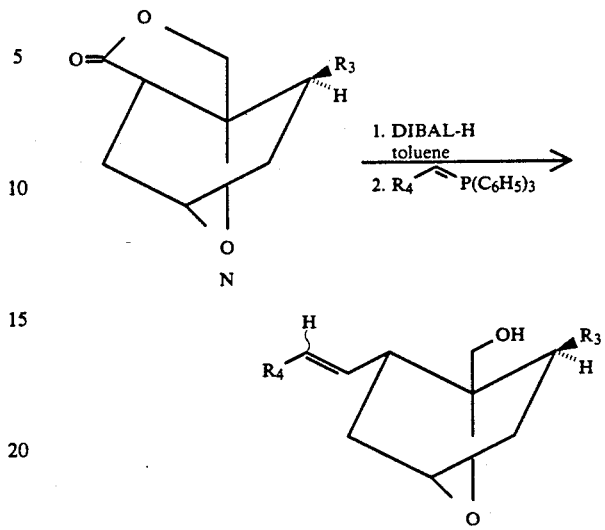

As will be apparent in the above reaction schemes and hereinafter, the terms
Me=$CH_3$
Et=$C_2H_5$
t-But=t-$C_4H_9$
Ac=$CH_3CO$
Ph=$C_6H_5$ The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels and lower plasma low density and intermediate density lipoprotein cholesterol levels.

As HMG CoA reductase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, DEAE-Sephadex as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors.

The above compounds to be employed in combination with the HMG CoA reductase inhibitor of the invention will be used in amounts as indicated in the Physicians' Desk Reference (PDR).

The compounds of this invention also have useful antifungal activities. For example, they may be used to control strains of Penicillium sp., *Aspergillus niger*, Cladosporium sp., *Cochliobolus miyabeorus* and *Helminthosporium cynodnotis*. For those utilities they are admixed with suitable formulating agents, powders, emulsifying agents or solvents such as aqueous ethanol and sprayed or dusted on the plants to be protected.

In addition, the compounds of the invention may be useful in elevating HDL-cholesterol while lowering levels of LDL-cholesterol and serum triglycerides, and for treating tumors.

The compounds of the invention prepared as described above are single, homochiral diastereomers. The compounds of the described absolute stereochemistry are preferred, but compounds with the opposite stereochemistry at one or more of the stereocenters are also within the scope of the present invention.

The compounds of the invention are inhibitors of 3-hydroxy-3-methyl-glutaryl coenzyme A (HMG-CoA) reductase and thus are useful in inhibiting cholesterol biosynthesis.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner and in amounts as known compounds suggested for use in inhibiting cholesterol biosynthesis, such as lovastatin or pravastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following working examples represent preferred embodiments of the invention. Unless otherwise specified, all temperature are in degrees Centigrade (°C.).

EXAMPLE 1

[1S-[1α(βR*,δR*),2α,4α]-β,δ-Dihydroxy-2-(2-phenylethyl)-7-oxabicyclo[2.2.1]heptane-1-heptanoic acid, monolithium salt A. (R)-N-(2-Hydroxy-1-phenylethyl)-2-furamide A solution of D-(-)-α-phenylglycinol (1.18 g, 8.43 mmole) and triethylamine (3.18 mL, 23 mmole) were dissolved in dry tetrahydrofuran (20 mL), cooled down to 0° C. (ice bath) and treated dropwise with furoyl chloride (0.76 mL or 1.0 g, 7.66 mmole). The reaction mixture was stirred at 0° C. for 1.0 hour, diluted with ether (100 mL) and washed with 5% HCl (20 mL). The aqueous phase was re-extracted with ether (100 mL) and the combined ether extracts were washed with brine (20 mL), dried (anhydrous MgSO$_4$), filtered and evaporated to dryness to give the title compound (1.79 g, quantitative crude yield) as a solid, m.p. 130–131° C.

TLC: Rf 0.17 (Silica gel; EtOAc: hexane-1:1).

B. (R)-N-(2-Hydroxy-1-phenylethyl)-2-aminomethylfuran

A solution of the Part A amide (11.15 g, 46 mmole) in dry tetrahydrofuran (25 mL) was added dropwise under N$_2$ to a cooled (0°, ice bath) suspension of 95% lithium aluminum hydride (LAH) (2.45 g, 61.3 mmol) in dry tetrahydrofuran (25 mL). The reaction mixture was refluxed for 2.5 hours, cooled in an ice bath and quenched by the sequential addition of H$_2$O (2.45 mL), 10% NaOH (3.68 mL) and water (7.35 mL). The resulting suspension was stirred for 30 minutes, mixed with Celite and filtered, washing the cake well with dichloromethane (250 mL). The combined filtrates were dried (anhydrous MgSO$_4$), filtered and evaporated to give the title compound as an oil (9.90 g, 99.1%).

TLC: Rf 0.45 (Silica gel; Acetone: hexane-2:3).

C. (R)-N-(2-Furanylmethyl)-N-(2-hydroxy-1-phenylethyl)-2-propenamide

A solution of the Part B amine (9.90 g, 45.6 mmole) and triethylamine (15.8 mL, 91.2 mmole, 2.5 eq.) in dry tetrahydrofuran (200 mL) was cooled down to 0° C. (ice bath) under N$_2$ and treated dropwise with acryloyl chloride (5.7 mL, 68.4 mmole, 1.5 eq.). The mixture was stirred at 0° C. for 1.0 hour and partitioned between 5% HCl (160 mL) and ether (3×250 mL). The combined ether extracts were washed with brine (100 mL), dried (anhydrous MgSO$_4$), filtered and evaporated to dryness to give a syrup (11.14 g) containing two products. The product mixture was dissolved in dioxane (100 mL), treated with 1N LiOH (41 mL, 1 eq.) and stirred at room temperature under N$_2$ for 1.0 hour. The mixture was acidified with 10% HCl to pH 5.5, concentrated to remove most of the dioxane and the resulting slurry partitioned between brine (2×100 mL) and ether (3×300 mL). The combined organic extracts were dried (anhydrous MgSO$_4$), filtered and evaporated to dryness. The crude product was chromatographed on a silica gel column (Baker, 500 mL), eluting the column with EtOAc: hexane mixture (1:4; 1:2; 1:1) to give the title compound as a homogeneous syrup (6.82 g, 55.1%).

TLC: Rf 0.33 (Silica gel; Acetone:hexane-2:3).

D. [3aS-[2(R*),3aα,6α,7aβ]]-2,3,7,7a-Tetrahydro-2-(2-hydroxy-1-phenylethyl)-3a,6-epoxy-3aH-isoindol-1(7aH)-one and E. [3aR-[2(R*),3aα,6α,7aβ]]-2,3,7,7a-Tetrahydro-2-(2-hydroxy-1-phenylethyl)-3a,6-epoxy-3aH-isoindol-1(7aH)-one A solution of Part C alcohol (4.61 g, 17.0 mmole) in dry tetrahydrofuran (115 mL) was cooled down to −78° C. (dry ice-acetone) under argon, treated with 2M hexylmagnesium bromide (8.60 mL, 17.2 mmole) and stirred at −78° for 30 minutes. The mixture was allowed to warm up to room temperature, the solvent blown off with a strong stream of argon and the resulting solid dried in vacuo (pump) for 1.5 hours. The off-white solid was suspended in dry toluene (140 mL) and refluxed under argon for 2.5 hours. The mixture was cooled, treated with 10% HCl (71 mL) and extracted with dichloromethane (3×250 mL). The combined organic extracts were washed with brine (140 mL), dried (anhydrous MgSO$_4$), filtered and evaporated to dryness. The product mixture was chromatographed on a silica gel column (Baker, 60–200 mesh, 800 mL), eluting the column with ethyl acetate to give title Part D alcohol (1.00 g, 22%) as an oil, Rf=0.20 (EtOAc) and the Part E alcohol (2.70g, 60%) as a solid, Rf=0.13 (EtOAc). Recrystallization of a 0.32 gm sample of the Part E alcohol from EtOAc gave 0.20 gm of pure product as fine needles, mp 125–126° C. The structure of the Part E alcohol was established by X-ray crystallography.

For the Part E alcohol:
Anal. Calc'd for $C_{16}H_{17}NO_3$: C, 70.83; H, 6.32; N, 5.16
Found: 3, 70.94; H, 6.33; N, 5.15.
$[\alpha]_D = -93.2°(C=1.01.\ MeOH)$.
$^1$H-NMR (CDCl$_3$, 270 MHz) δ 1.60 (dd, 1H, J=9, 12 Hz), 2.22 (dt, 1H, J=5 Hz), 2.57 (dd, 1H, J=9, 2 Hz), 3.44 (broad s, 1H), 3.57 (d, 1H, J=12 Hz), 4.00 (d, 1H, J=12 Hz), 4.12 (m, 2H), 5.07 (d, 1H, J=4 Hz), 5.20 (dd, 1H, J=9, 4 Hz), 6.38 (s, 2H), 7.21–7.37 (m, 5H).

F. [3aS-[2(R*),3aα,6α,7aβ]]-Hexahydro-2-(2-hydroxy-1-phenylethyl)-3a,6-epoxy-3aH-isoindol-1(7aH)-one A solution of Part D alcohol (5.1 g, 18.8 mmole) in dry methanol (230 mL) was treated with 5% Pd/C (448 mg) and hydrogenated at room temperature. The reaction mixture was, upon completion, stirred with Celite (5.0 g) and filtered through a millipore unit, washing the pad well with methanol. The clear filtrate was evaporated to dryness to give title alcohol as an oil (5.0 g, 97.3%).

TLC: R$_f$ 0.22 (Silica gel; EtOAc:MeOH-9:1).

G. 3aS-(3aα,6α,7aβ)]-Hexahydro-3a,6-epoxy-3aH-isoindol-1(7aH)-one

A solution of Part F alcohol (5.0 g, 18.3 mmole) in dry tetrahydrofuran (200 mL) was added to a cooled solution of liquid ammonia (2.0 l), stirred for 30 minutes then treated portionwise with sodium metal (4.2 g, 0.183 mole, 10 eq.). After addition was completed, the mixture was stirred at −78° for another two hours then quenched with solid ammonium chloride (19.2 g). The solution was allowed to warm up to room temperature overnight to evaporate off the ammonia, diluted with water (100 mL) and extracted with dichloromethane (3×400 mL). The combined organic extracts were washed with brine (100 mL), dried (anhydrous MgSO$_4$), filtered and evaporated to dryness. The product mixture (3.88 g, oil) was chromatographed on a silica gel column (Baker, 60-200 mesh, 400 mL), eluting the column with EtOAc:Hexane mixtures (1:1; 9:1) and ethyl acetate to give title compound as a homogeneous oil (2.29 g, 81.6%).

TLC: R$_f$ 0.37 (Silica gel; EtOAc:CH$_3$OH-9:1).

H. [3aS-(3aα,6α,7aβ)]-Hexahydro-2-nitroso-3a,6-epoxy-3aH-isoindol-1(7aH)-one

Part G compound (500 mg, 3.26 mmole) was dissolved in a mixture of glacial acetic acid (3.3 mL) and acetic anhydride (16.3 mL), cooled down to 0° under nitrogen and treated over a period of 5 hours with sodium nitrite (4.9 g, 71.0 mmole). The mixture was stirred at 0° (ice water) for another 20 hours in the cold room and the resulting yellow-green solution was poured onto ice water (25 mL) and extracted with diethyl ether (ether) (3×50 mL). The combined organic extracts were washed with 5% NaHCO$_3$ (2×25 mL), brine (25 mL), dried (anhydrous MgSO$_4$), filtered and evaporated to dryness. The crude product (500 mg, yellow-green oil) was chromatographed quickly through a silica gel column (Baker, 60-200 mesh, 25 mL), eluting the column with EtOAc: Hexane (1:1). The desired fractions were combined and evaporated to dryness, to give title compound as a homogeneous oil (444.8 mg, 68.8%).

TLC: R$_f$ 0.75 (Silica gel; EtOAc:CH$_3$OH (MeOH)-9:1).

I. [3aS-(3aα,6α,7aβ)]-Tetrahydro-3H-3a,6-epoxyisobenzofuran-1(7aH)-one

A solution of Part G compound (1.87 g, 9.44 mmole) in absolute ethanol (20 mL) was cooled down to 0° (ice water) and treated dropwise with a solution of 2N KOH in EtOH (13.8 mL). The mixture was stirred at 0° for 20 minutes, acidified with 10% HCl (14.7 mL) and stirred for another 15 minutes at 0°. The mixture was evaporated to dryness, azeotroping off the residual HCl by evaporating the semi-solid several times with acetonitrile. The product was triturated with ethyl acetate (3×200 mL) and the combined extracts were evaporated to dryness. The product mixture (1.82 g) was dissolved in dry benzene (75 mL), treated with TsOH.H$_2$O (150 mg) and stirred overnight at room temperature under N$_2$. The solution was evaporated to dryness, and the crude product was chromatographed on a silica gel column (Baker, 60-200 mesh, 150 mL), eluting the column with EtOAc:Hexane mixtures (1:4; 1:1). The desired fractions were combined and evaporated to give title compound as a semi-solid (1.3 g, 80.7%).

TLC: R$_f$ 0.35 (Silica gel; EtOAc:Hexane-1:1).

J. [3aS-(3aα,6α,7aβ)]-Hexahydro-3H-3a,6-epoxyisobenzofuran-1-ol

A solution of Part I compound (650 mg, 3.82 mmole) in dry toluene (17.3 mL) was cooled down to −78° (dry ice-acetone) under argon, treated dropwise with 1.0M diisobutyl aluminum hydride (DiBAL) in heptane (9.5 mL) and stirred at −78° for 3 hours. The mixture was quenched by adding silica gel (7.0 g) and water (1.15 mL), allowed to warm up to room temperature and stirred for 30 minutes. The slurry was filtered, washing the silica gel well with ethyl acetate (3×100) and EtOAc:MeOH (9:1; 2×50 mL). The combined filtrates were evaporated to dryness and the crude product mixture (639.9 mg) was chromatographed on a silica gel column (Baker, 60-200 mesh, 50 mL), eluting the column with EtOAc:Hexane mixtures (1:4; 1:2; 1:1) and ethyl acetate. The desired fractions were combined and evaporated to give title compound as a homogeneous oil (467.3 mg, 71.1%).

TLC: R$_f$ 0.22 (Silica gel; EtOAc:Hexane-1:1).

A minor product, R$_f$ 0.08, was obtained as a homogeneous oil (87.8 mg, 13.3%) and shown by H$^1$-NMR and C$^{13}$-NMR spectral data to be the overreduced compound, i.e., the diol.

K. [1S-[1α,2α(E),4α]]-2-(2-Phenylethenyl)-7-oxabicyclo[2.2.1]heptane-1-methanol

A suspension of benzyltriphenylphosphonium chloride (7.63 g, 19.6 mmole, 7.37 eq.) in dry tetrahydrofuran (72 mL) was cooled down to 0° (ice water) under argon and treated dropwise with a solution of 1.73M K-t-amylate (8.65 mL, 1.89 g or 15 mmole; 5.6 eq.) and stirred at 0° for one hour. The suspension was then treated with a solution of Part J compound (457.4 mg, 2.66 mmole) in dry tetrahydrofuran (10 mL), stirred at 0° for 1 hour and at room temperature for 2 hours. The mixture was partitioned between 5% KHSO$_4$ (30 mL) and ethyl acetate (3×100 mL). The combined organic extracts were washed with brine (25 mL), dried (anhydrous MgSO$_4$), filtered and evaporated to dryness. The crude product (5.3 g) was chromatographed on a silica gel column (LPS-1), eluting the column with EtOAc:Hexane (1:4) to give title compound as a waxy solid (635.4 mg, 100%).

TLC: R$_f$ 0.43 (Silica gel; EtOAc:Hexane-1:1).

L. [1S-(1α,2α,4α)-2-(2-Phenylethyl)-7-oxabicyclo[2.2.1]heptane-1-methanol

A solution of Part K compound (635.4 mg, 2.77 mmole) in dry methanol (40 mL) was treated with 5% Pd/C (50 mg) and hydrogenated at room temperature. The reaction mixture, upon completion, was filtered through a Celite pad in a millipore unit, washing the pad well with methanol. The clear filtrate was evaporated to dryness to give title compound as a heavy oil (654.3 mg, 100%).

TLC: $R_f$ 0.45 (Silica gel; EtOAc:Hexane-1:1).

M. [1S-(1α,2α,4α)]-2-(2-Phenylethyl)-7-oxabicyclo2.2.1]heptane-1-carboxaldehyde

A mixture of t-butyl alcohol (t-BuOH) (0.22 mg, 2.32 mmole; 1.4 eq.) and Dess-Martin periodinane (987.4 mg; 2.32 mmole; 1.4 eq.) in dry dichloromethane (12 mL) was stirred under argon for 15 minutes, treated with a solution of Part L compound (383.3 mg, 1.66 mmole) in dry dichloromethane (7.0 mL) and stirred at room temperature for 6.0 hours. The mixture was diluted with ether (50 mL), poured into 1N NaHCO$_3$ (15 mL) containing a seven-fold excess of Na$_2$S$_2$O$_3$ (3.0 g) and stirred until all the precipitates went into solution. The aqueous phase was extracted with ether (2×50 mL) and the combined organic extracts were washed with 1N NaHCO$_3$ (15 mL), brine (15 mL), dried (anhydrous MgSO$_4$), filtered and evaporated to dryness. The crude product mixture (452.8 mg) which contained a small amount of starting material and a trace of a more polar component, $R_f$ 0.18, was chromatographed on a silica gel column (Baker, 60-200 mesh, 40 mL), eluting the column with EtOAc:Hexane (1:4). The desired fractions were combined and evaporated to dryness to give title compound as a homogeneous oil (331.4 mg, 87.1%).

TLC: $R_f$ 0.70 (Silica gel; EtOAc:Hexane-1:1).

N. [1R-[1α(R*,E),2α,4α]]-3-[[(1,1-Dimethylethyl)dimethylsilyl]oxy]-5-oxo-7-[2-(2-phenylethyl)-7-oxabicyclo[2.2.1]hept-1-yl]-6-heptenoic acid, methyl ester A solution of (R)-6-(dimethoxyphosphinyl)-3-[[(1,1-dimethylethyl)dimethylsilyl]oxy-5-oxo-hexanoic acid, methyl ester (prepared as described in U.S. Pat. No. 4,804,770) (594 mg; 1.6 mmole) in dry acetonitrile (8 mL) was treated successively with dry LiCl (65 mg), 1,8-diazabicyclo[5.4.0]undec-7-ene (DBU) (195 μL) and Part M compound (290 mg, 1.26 mmole) as a suspension in dry acetonitrile (8.0 mL) and stirred overnight (18 hrs.) at room temperature under argon. The reaction mixture was partitioned between 5% KHSO$_4$ (15 mL) and ethyl acetate (3×50 mL) and the combined organic extracts were washed with saturated NaHCO$_3$ (15 mL), brine (15 mL), dried (anhydrous MgSO$_4$), filtered and evaporated to dryness. The crude product was chromatographed on a silica gel column (Whatman LPS-1), eluting the column with EtOAc:Hexane (1:4). The desired fractions were combined and evaporated to dryness to give title compound as a homogeneous oil (487.8 mg, 77.1%).

TLC: $R_f$ 0.55 (Silica gel; acetone:hexane-2:3).

O. [1R-[1α(R*,2α,4α]]-β-[[(1,1-Dimethylethyl)dimethylsilyl]oxy]-δ-oxo-2-(2phenylethyl)-7-oxabicyclo[2.2.1]heptane-1-heptanoic acid, methyl ester A solution of Part N compound (487.7 mg; 1.0 mmole) in dry methanol (40 mL) was treated with 5% Pd/C (40 mg) and hydrogenated at room temperature. The reaction mixture, upon completion, was filtered through a Celite pad in a millipore unit, washing the pad well with methanol. The clear filtrate was evaporated to give title compound as a homogeneous oil (490 mg, 100%).

TLC: $R_f$ 0.38 (Silica gel; EtOAc:Hexane-1:4).

P [1R-[1α(R*),2α,4α]]-β-Hydroxy-δ-oxo-2-(2-phenylethyl)-7-oxabicyclo[2.2.1]heptane-1-heptanoic acid, methyl ester A solution of Part O compound (470 mg; 0.91 mmole) in dry tetrahydrofuran (25 mL) was treated with glacial acetic acid (0.44 mL; 7.28 mmole; 8 eq.), followed by 1M (C$_4$H$_9$)$_4$NF/THF (5.7 mL, 5.7 mmole; 6 eq.) and stirred at room temperature under argon for 2.5 days. The reaction mixture was diluted with ice water (20 mL) and extracted with ether (2×100 mL). The combined organic extracts were washed with saturated sodium bicarbonate (15 mL), brine (20 mL), dried (anhydrous MgSO$_4$), filtered and evaporated to dryness. The crude product (382.9 mg) was chromatographed on a silica gel column (LPS-1), eluting the column with EtOAc: hexane mixtures (1:4; 1:1) to give title compound as a homogeneous oil (288.5 mg, 88.3%).

TLC: $R_f$ 0.47 (Silica gel; EtOAc:hexane-1:1).

Q. [1S-[1α(βR*,δR*),2α,4α]-β,δ-Dihydroxy-2-(2-phenylethyl)-7-oxabicyclo[2.2.1]-heptane-1-heptanoic acid, methyl ester A solution of Part P compound (360 mg, 0.96 mmole) in dry tetrahydrofuran (14.2 mL) was treated with 1M triethylboron (Et$_3$B)-THF (1.42 mL; 1.42 mmole; 1.48 eq.), stirred at room temperature under argon for 30 minutes then cooled down to −78° (dry ice-acetone). The cooled solution was treated with sodium borohydride (85.1 mg; 2.25 mmole; 2.34 eq.), followed by the dropwise addition of dry methanol (3.55 mL) and the reaction mixture stirred at −78° for 2 hours. The mixture was quenched by treatment at −78° with 30% H (2.13 mL)—H$_2$O (7.1 mL), stirred for 15 minutes, warmed up to room temperature and stirred for another 30 minutes. The mixture was then diluted with water (10 mL) and extracted with ethyl acetate (3×100 mL). The combined organic extracts were washed with saturated NaHCO$_3$ (15 mL), brine (20 mL), dried (anhydrous MgSO$_4$), filtered and evaporated to dryness. The crude product (441.5 mg) was chromatographed (flash) on a silica gel column (LPS-1), eluting the column with EtOAc:Hexane (1:1). The desired fractions were combined and evaporated to give title compound as a homogeneous oil (363.3 mg, 100%).

TLC: $R_f$ 0.13 (Silica gel; EtOAc:hexane-1:1).

R. [1S-[1α(βR*,δR*),2α,4α]-β,δ-Dihydroxy-2-(2-phenylethyl)-7-oxabicyclo[2.2.1]heptane-1-heptanoic acid, monolithium salt A solution of Part Q ester (361.4 mg, 0.96 mmole) in dioxane (7.1 mL) was treated with 1N LiOH (1.42 mL) and stirred at room temperature under argon for 1.0 hour. The reaction mixture was stripped to dryness and the solid obtained (~516 mg) slurried in water (3.0 mL) and chromatographed on an HP-20 column (1"×3"), eluting the column with steam-distilled water (250 mL), followed by 50% aqueous CH$_3$OH (500 mL). The fractions containing the desired compound were combined, evaporated to dryness and dried in vacuo for 1.0 hour. The solid was dissolved in water (30 mL) and lyophilized to give title product as a fluffy solid (323 mg, 91.3%).

IR (KBr) (1578 cm$^{-1}$, strong, C=O; 3206 cm$^{-1}$, strong, OH).

TLC: $R_f$ 0.50 (Silica gel; CH$_2$Cl$_2$—CH$_3$OH—HOAc—20:1:1).

Anal. Calc'd for C$_{21}$H$_{29}$LiO$_5$: C, 68.46; H, 7.93 Found: C, 68.15; H, 7.97.

H$^1$-NMR Spectrum (270 MHz, CD$_3$OD) δ 1.20-1.93 (m, 15H), 2.21-2.45 (m, 3H), 2.59-2.70 (m, 1H), 3.77 (quint, 1H), 4.09 (quint, 1H), 4.45 (t, 1H, J=~4), 7.09-7.28 (m, 5H).

EXAMPLE 2

[1R-[1α(βR*,δR*),2α,4α]]-β,δ-Dihydroxy-2-(2-phenylethyl)-7-oxabicyclo[2.2.1]heptane-1-heptanoic acid, monolithium salt A. [3aR-(2(R*),3α,6α,7aβ)]-Hexahydro-2-(2-hydroxy-1-phenylethyl)-3a,6-epoxy-3aH-isoindol-1(7aH)-one A solution of Example 1, Part E compound (12.3 g, 45.3 mmole) in dry methanol (550 mL) was treated with 5% Pd/C (1.08 g) and hydrogenated at room temperature. The reaction mixture was, upon completion, diluted with methanol (500 mL) and filtered through a Celite pad in a millipore unit, washing the pad well with methanol. The clear filtrate was evaporated to dryness to give title compound as a solid (12.10 g, 97.7%).

TLC $R_f$ 0.17 (Silica gel; EtOAc).

B. [3aR-(3aα,6α,7aβ)]-Hexahydro-3a,6-epoxy-3aH-isoindol-1(7aH)-one

A solution of Part A compound (12.1 g, 44.3 mmole) in dry tetrahydrofuran (450 mL) was added to a cooled (−78°; dry ice-acetone) solution of liquid ammonia (4.0 l), stirred for 30 minutes, then treated portionwise with sodium metal (10.2 g; 0.44 mole; 10 eq.). After addition was completed, the mixture was stirred at −78° for another 2 hours, then quenched with solid ammonium chloride (42.5 g). The solution was allowed to warm up to room temperature overnight to evaporate off the ammonia, diluted with water (250 mL) and extracted with dichloromethane (3×1.0 l). The combined organic extracts were washed with brine (200 mL), dried (anhydrous MgSO₄), filtered and evaporated to dryness. The product mixture (8.15 g) was chromatographed on a silica gel column (Baker, 60-200 mesh, 400 mL), eluting the column with EtOAc:Hexane mixtures (1:1; 1:4) and ethyl acetate to give title compound as a colorless oil (5.9 g, 36.9%).

TLC: $R_f$ 0.30 (Silica gel; EtOAc:MeOH-9:1).

C. [3aR-(3aα,6α,7aβ)]-Hexahydro-2-nitroso-3a,6-epoxy-3aH-isoindol-1(7aH)-one

Part B compound (5.9 g, 38.5 mmole) was dissolved in a mixture of glacial acetic acid (39 mL) and acetic anhydride (194 mL), cooled down to 0° (ice water) under nitrogen and treated with sodium nitrite (58.0 g, 0.84 mole) over a period of 5 hours. The mixture was stirred at 0° (ice water) for another 20 hours in the cold room and the resulting yellow-green solution was poured onto ice water (250 mL) and extracted with dichloromethane (3×500 mL). The combined organic extracts were washed with saturated NaHCO₃ (250 mL), dried (anhydrous MgSO₄), filtered and evaporated to dryness. The crude product (7.45 g, yellow-green oil) was chromatographed on a silica gel column (Baker, 6-200 mesh, 400 mL), eluting the column with EtOAc:Hexane mixtures (1:4; 1:1; 4:1) to give title compound as a yellow oil (4.75 g, 62.3%).

TLC: $R_f$ 0.48 (Silica gel; EtOAc:hexane-1:1).

D. [3aR-(3aα,6α,7aβ)]-Tetrahydro-3a,6-epoxyisobenzofuran-1(7aH)-one

A solution of Part C compound (4.75 g, 24.0 mmole) in absolute ethanol (50 mL) was cooled down to 0° (ice water) and treated dropwise with a solution of 2N KOH in ethanol (EtOH) (35 mL). The mixture was stirred under nitrogen at 0° for 20 minutes at 0°. The mixture was evaporated to dryness, azeotroping off the residual HCl by evaporating the semi-solid several times with acetonitrile. The product was triturated with ethyl acetate (2×500 mL) and the combined extracts were evaporated to dryness. The product mixture (3.33 g) was dissolved in dry benzene (150 mL), treated with TsOH.H₂O (300 mg) and stirred overnight at room temperature under N₂. The solution was evaporated to dryness and the crude product chromatographed on silica gel column (Whatman LPS-1), eluting the column with EtOAc:Hexane (1:4). The desired fractions were combined and evaporated to give title compound as a semisolid (2.60 g, 63.9%).

TLC: $R_f$ 0.33 (Silica gel; EtOAc:hexane-1:1).

E. [3aR-(3aα,6α,7aβ)]-Hexahydro-3a,6-epoxyisobenzofuran-1-ol

A solution of Part D compound (1.0 g, 5.88 mmole) in dry toluene (27 mL) was cooled down to 78° (dry ice-acetone) under argon, treated dropwise with 1.0M diisobutyl aluminum hydride (DiBAL) in heptane (7.8 mL, 7.79 mmole) and stirred at −78° for 3.0 hours. The mixture was quenched by adding silica gel (7.0g) and water (0.94 mL) at −78°, allowed to warm up to room temperature and stirred for 30 minutes. The slurry was filtered, washing the silica gel with ethyl acetate (3×100 mL) and EtOAc:MeOH (9:1, 2×100 mL). The combined filtrates were evaporated to dryness and the crude product chromatographed on a silica gel column (Baker, 60-200 mesh, 150 mL), eluting the column with EtOAc:Hexane mixtures (1:4; 1:2; 1:1) and ethyl acetate. The desired fractions were combined and evaporated to give title compound as an oil (732.9 mg, 86.1%).

TLC: $R_f$ 0.17 (Silica gel; EtOAc:hexane-1:1).

F. [1R-[1α,2α(E),4α]]-2-(2-Phenylethenyl)-7-oxabicyclo[2.2.1]heptane-1-methanol

A suspension of benzyltriphenylphosphonium chloride (4.17 g, 10.7 mmole or 7.4 eq.) in dry tetrahydrofuran (45 mL) was cooled down to 0° (ice water) under argon and treated dropwise with 1.73M K-t-amylate (4.73 mL; 8.2 mmole; 5.7 eq.). The resulting suspension was stirred at 0° for 1.0 hour, treated with a solution of Part E compound (250 mg, 1.45 mmole) in dry tetrahydrofuran (6.0 mL), stirred at 0° for another hour and at room temperature overnight. The mixture was partitioned between 5% KHSO₄ (15 mL) and ethyl acetate (3×60 mL) and the combined organic extracts were washed with brine (15 mL), dried (anhydrous MgSO₄), filtered and evaporated to dryness. The crude product (3.2 g) was chromatographed on a silica gel column (Baker, 60-200 mesh, 150 mL), eluting the column with EtOAc:hexane (1:4). The desired fractions were combined and evaporated to give title compound as a colorless oil (328.6 mg, 98.7%).

TLC: $R_f$ 0.50 (Silica gel; EtOAc:hexane-1:1).

G. 1R-(1α,2α,4α)]-2-(2-Phenylethyl)-7-oxabicyclo[2.2.1]heptane-1-methanol

A solution of Part F compound (328.6 mg, 1.43 mmole) in dry methanol (30 mL) was treated with 5% Pd/C (30 mg) and hydrogenated at room temperature. The reaction mixture, upon completion, was filtered through a Celite pad in a millipore unit, washing the pad well with methanol. The clear filtrate was evaporated to dryness to give title compound as a colorless, viscous oil (319.1 mg, 96.7%).

TLC: $R_f$ 0.50 (Silica gel; EtOAc:Hexane-1:1).

H. [1R-(1α,2α,4α)]-2-(2-Phenylethyl)-7-oxabicyclo[2.2.1]heptane-1-carboxaldehyde A mixture of t-butanol (0.20 mL; 2.11 mmole; 1.5 eq.) and Dess-Martin periodinane (892.5 mg; 2.11 mmole; 1.5 eq.) in dry dichloromethane (6.5 mL) was stirred under argon for 15 minutes, treated with a solution of Part G compound (319.1 mL; 1.39 mmole) in dry dichloromethane (6.5 mL) and stirred at room temperature for 20 hours. The mixture was diluted with $CH_2Cl_2$ (50 mL), poured in 1N $NaHCO_3$ (18 mL) containing a seven-fold excess of $Na_2S_2O_3$ (3.48 g) and stirred until all the precipitates went into solution. The aqueous phase was extracted with $CH_2Cl_2$ (2×50 mL) and the combined organic extracts were washed with brine (20 mL), dried (anhydrous $MgSO_4$), filtered and evaporated to dryness. The crude product mixture (363.3 mg) which contained a small amount of starting material and a trace of a more polar component, $R_f 0.18$, was chromatographed on a silica gel column (LPS-1), eluting the column with EtOAc:Hexane (1:4). The desired fractions were combined and evaporated to dryness to give title compound as a colorless oil (318.7 mg, 84.0%).

TLC: $R_f 0.38$ (Silica gel; EtOAc:Hexane-1:1).

I [1S-[α(R*,E),2α,4α]]-3-[[(1,1-Dimethylethyl)dimethylsilyl]oxy]-5-oxo-7-[2-(2-phenylethyl)-7-oxabicyclo[2.2.1]hept-1-yl]-6-heptenoic acid, methyl ester A solution of (R)-6-(dimethoxyphosphinyl)-3-[[(1,1-dimethylethyl)dimethylsilyl]oxy]-5-oxo-hexanoic acid, methyl ester (533.7 mg, 1.39 mmole) in dry acetonitrile (8 mL) was treated successively with dry LiCl (59 mg), 1,8-diazabicyclo[5.4.0]undec-7-ene (DBU) (175 μL) and Part H compound (267 mg, 1.17 mmole) as a suspension in dry acetonitrile (8.0 mL) and stirred overnight at room temperature under argon. The reaction mixture was partitioned between 5% $KHSO_4$ (15 mL) and ethyl acetate (3×50 mL) and the combined organic extracts washed with saturated $NaHCO_3$ (15 mL), brine (20 mL), dried (anhydrous $MgSO_4$), filtered and evaporated to dryness. The crude product (726.6 mg) was chromatographed on a silica gel column (LPS-1), eluting the column with EtOAc:Hexane (1:4). The desired fractions were combined and evaporated to dryness to give title compound as a colorless oil (479.8 mg, 84.2%).

TLC: $R_f 0.77$ (Silica gel; EtOAc:Hexane-1:1).

J. [1S-[1α(R*),2α,4α]]-β-[[(1,1-Dimethylethyl)dimethylsilyl]oxy]-δ-oxo-2-(2-phenylethyl)-7-oxabicyclo[2.2.1]heptane-1-heptanoic acid, methyl ester A solution of Part I compound (479.8 mg, 0.99 mmole) in dry methanol (40 mL) was treated with 5% Pd/C (40 mg) and hydrogenated at room temperature. The reaction mixture, upon completion, was filtered through a Celite pad in a millipore unit, washing the pad well with methanol. The clear filtrate was evaporated to dryness to give title compound as a colorless oil (488.6 mg, 100%).

TLC: $R_f 0.23$ (Silica gel; EtOAc:Hexane-1.4).

K. [1S-[1α(R*),2α,4α]]-β-Hydroxy-δ-oxo-2-(2-phenylethyl)-7-oxabicyclo[2.2.1]heptane-1-heptanoic acid, methyl ester A solution of Part I compound (409 mg, 0.84 mmole) in dry tetrahydrofuran (25 mL) was treated with glacial acetic acid (0.44 mL; 7.28 mmole; 8.6 eq.) followed by 1M $(C_4H_9)_4NF/THF$ (5.7 mL; 5.46 mmole; 8.6 eq.) and stirred overnight at room temperature. The reaction mixture was diluted with ice water (20 mL) and extracted with ether (3×100 mL). The combined organic extracts were washed with saturated $NaHCO_3$ (15 mL), brine (15 mL), dried (anhydrous $MgSO_4$), filtered and evaporated to dryness. The crude product (~700 mg) was chromatographed on a silica gel column (LPS-1), eluting the column with EtOAc:Hexane mixtures (1:4; 1:1). The desired fractions were combined and evaporated to dryness to give title compound as a colorless oil (305.3 mg, 91.8%).

TLC: $R_f 0.32$ (Silica gel; EtOAc:Hexane-1:1).

L. [1R-[1α(βR*,δR*),2α,4α]]-β,δ-Dihydroxy-2-(2-phenylethyl)-7-oxabicyclo[2.2.1]heptane-1-heptanoic acid, methyl ester A solution of Part K compound (315.7 mg, 0.84 mmole) in dry tetrahydrofuran (12.4 mL) was treated with 1M $(C_2H_5)_3B$ (1.24 mL, 1.24 mmole, 1.48 eq.), stirred at room temperature under argon for 30 minutes then cooled down to −78° (dry ice-acetone). The cooled solution was treated with sodium borohydride (74.5 mg, 1.97 mmole, 2.34 eq.) followed by the dropwise addition of dry methanol (3.55 mL) and the reaction mixture stirred at −78° for two hours. The mixture was quenched by treatment at −78° with 30% $H_2O_2$ (1.86 mL)-$H_2O$ (6.2 mL), stirred for 15 minutes, warmed up to room temperature and stirred for another 30 minutes. The mixture was then diluted with water (8.0 mL) and extracted with ethyl acetate (3×100 mL). The combined organic extracts were washed with saturated $NaHCO_3$ (15 mL), brine (20 mL), dried (anhydrous $MgSO_4$), filtered and evaporated to dryness. The crude product (387.9 mg) was chromatographed on a silica gel column (LPS-1), eluting the column with EtOAc:Hexane 1:1). The desired fractions were combined and evaporated to dryness to give title compound as a colorless oil (298.7 mg, 94.3%).

TLC: $R_f 0.18$ (Silica gel; EtOAc:hexane-1:1).

M. [1R-[1α(βR*,δR*),2α,4α]]-β,δ-Dihydroxy-2-(2-phenylethyl)-7-oxabicyclo[2.2.1]heptane-1-heptanoic acid, monolithium salt A solution of Part L ester (298.7 mg, 0.79 mmole) in dioxane (5.9 mL) was treated with 1N LiOH (1.17 mL, 1.17 mmole or 1.5 eq.) and stirred at room temperature for 1.0 hour. The reaction mixture was evaporated to dryness and the residue was dissolved in a minimal amount of $H_2O$ and chromatographed on an HP-20 column (1"×3"), eluting the column with steam-distilled water (250 mL), followed by 50% aqueous $CH_3OH$ (500 mL). The fractions containing the desired product were combined, evaporated to dryness, redissolved in steam-distilled water (30 mL), and lyophilized. Title salt was obtained as a flocculent solid (290 mg, 94.6%).

IR (1579 cm$^{-1}$, strong, C=O; 2941 cm$^{-1}$, strong, —OH).

TLC: $R_f 0.27$ (Silica gel; $CH_2Cl_2$:$CH_3OH$:acetic acid (HOAc)-20:1:1).

Anal. Calc'd for $C_{21}H_{29}LiO_5$ 1.1 $H_2O$: C, 64.97; H, 8.10

Found: C, 64.89; H, 8.06.

H$^1$-NMR Spectrum (270 MHz, $CD_3OD$): δ 1.18–2.08 (m, 15H), 2.22–2.46 (m, 3H), 2.58–2.70 (m, 1H), 3.77 (quint, 1H), 4.09 (quint, 1H), 4.45 (t, 1H, J=~6), 7.08–7.28 (m, 5H).

EXAMPLE 3

[1R-[1α(βR*),6R*),2α,4α]]-2-[(2,2-Dimethyl-1-oxobutoxy)methyl-β, δ-dihydroxy-7-oxabicyclo[2.2.1]-heptane-1-heptanoic acid, monolithium salt A. [1R-(1α,2α,4α)]-2-Ethenyl-7-oxabicyclo[2.2.1]heptane-1-methanol A suspension of methyltriphenylphosphonium bromide (4.42 g, 12.4 mmole) in dry tetrahydrofuran (30 mL) was cooled down to −78° C. (dry ice-acetone)

under argon, treated with 1.6M n-butyllithium (6.8 mL, 10.9 mmole; 3.9 eq.) in hexane and stirred at −78° C. for 30 minutes and at 0° (ice water) for 1.0 hour. The reaction mixture was then treated 1.0 with a solution of [1S-(1α,3aβ,6β,7α)]-hexahydro-3H-3a,6-epoxyisobenzofuran-ol (prepared as described in Example 2, Part E) (482.9 mg, 2.8 mmole) in dry tetrahydrofuran (12 mL), stirred at 0° for 30 minutes, allowed to warm up to room temperature and stirred another 18 hours. The mixture was quenched with saturated ammonium chloride (5.0 mL), diluted with ethyl acetate (50 mL) and decanted, extracting the thick aqueous slurry two more times with ethyl acetate (50 mL). The combined organic extracts were dried (anhydrous MgSO$_4$), filtered and evaporated to dryness. The crude product was chromatographed on a silica gel column (LPS-1), eluting the column with EtOAc:Hexane (1:4) to give title compound as a colorless oil (354.1 mg, 74.2%).

TLC: $R_f$ 0.37 (Silica gel; EtOAc:hexane-1:1).

B. [1R-(1α,2α,4α)]-1-[[[(1,1-Dimethylethyl)dimethylsilyl]oxy]methyl]-2-ethenyl-7-oxabicyclo[2.2.1]heptane A solution of Part A compound (354.1 mg, 2.08 mmole) in dry methylene chloride (5 mL) was treated with t-butyldimethylsilylchloride (374.5 mg, 2.50 mmole, 1.2 eq.), 4-dimethylaminopyridine (50 mg) and triethylamine (0.35 mL, 2.53 mmole) and stirred at room temperature under argon for 16 hours. The mixture was diluted with dichloromethane (10 mL) and partitioned between 5% KHSO$_4$ (15 mL) and dichloromethane (2×50 mL). The combined organic extracts were dried (anhydrous MgSO$_4$), filtered and evaporated to dryness. The crude product was chromatographed on a silica gel column (LPS-1), eluting the column with EtOAc: Hexane (1:9) to give title compound as a colorless oil (534.7 mg, 95.8%).

TLC: $R_f$ 0.93 (Silica gel; EtOAc:Hexane-1:1).

C. [1R-(1α,2α,4α)]-1-[[[(1,1-Dimethylethyl)dimethylsilyl]oxy]methyl]-7-oxabicyclo[2.2.1]heptane-2-methanol A solution of Part B compound (534.7 mg, 1.99 mmole) was dissolved in dry methanol (25 mL), cooled down to −78° C. (dry ice-acetone) and ozone was bubbled through the solution until a blue color persisted. The solution was then purged with nitrogen until the blue color was discharged, treated with dimethylsulfide (0.57 mL) and stirred at −78° for 30 minutes. The mixture was evaporated to dryness and dried in vacuo for 40 minutes. The residual syrup was dissolved in dry tetrahydrofuran (25 mL), cooled down to 0° (ice water) and treated with lithium tri-tert-butoxyaluminum hydride (1.26 g, 4.96 mmole). The reaction mixture was allowed to warm up to room temperature, stirred for 1.5 hours under nitrogen then quenched with saturated sodium sulfate (5.7 mL) and stirred for 30 minutes The suspension was decanted, washing the solids well with dichloromethane (100 mL). The combined organic extracts were dried (anhydrous MgSO$_4$), filtered and evaporated to dryness. The crude product (531.3 mg) was chromatographed on a silica gel column (LPS-1), eluting the column with EtOAc:hexane (1:7). The desired fractions were combined and evaporated to give title compound as a colorless oil (440.9 mg, 81.3%).

TLC: $R_f$ 0.25 (Silica gel; EtOAc:hexane-1:4).

D. [1R-(1α,2α,4α)]-1-[[[(1,1-Dimethylethyl)dimethylsilyl]oxy]methyl]-7-oxabicyclo[2.2.1]heptane-2-methanol, 2,2-dimethylbutanoate A solution of Part C compound (440 mg, 1.61 mmole) in dry dichloromethane (15 mL) was treated with 4-dimethylaminopyridine (40 mg) and triethylamine (0.59 mL, 4.27 mmole, 2.66 eq.), cooled down to 0° (ice water) and treated with a solution of 2,2-dimethylbutyryl chloride (433.5 mg, 3.22 mmole, 2 eq.). The reaction mixture was stirred at 0° for 1 hour, at room temperature for 24 hours, then partitioned between 5% HCl (10 mL) and dichloromethane (3×50 mL). The combined organic extracts were washed with brine (15 mL), dried (anhydrous MgSO$_4$), filtered and evaporated to dryness. The crude product (769 mg) was chromatographed on a silica gel column (LPS-1), eluting the column with EtOAc:Hexane (1:9). The desired fractions were combined and evaporated to dryness, evaporating the residual syrup several times from toluene then dried in vacuo to remove the acid chloride which coeluted with the product. Title compound was obtained as an oil (525.6 mg, 88.1%).

TLC: $R_f$ 0.80 (Silica gel; EtOAc:hexane-1:4).

E. [1R-(1α,2α,4α)]-7-Oxabicyclo[2.2.1]heptane-1,2-dimethanol, 2-(2,2-dimethylbutanoate)

A solution of Part D compound (525.6 mg, 1.42 mmole) was dissolved in dry acetonitrile (32 mL), treated with 48% hydrofluoric acid (0.54 mL) and stirred at room temperature for 1.5 hours under argon. The reaction mixture was partitioned between a solution of NaHCO$_3$ (1.27 g) in water (10 mL) and ethyl acetate (3×75 mL). The combined organic extracts were washed with brine (20 mL), dried (anhydrous MgSO$_4$), filtered and evaporated to dryness. The crude product (380.6 mg) was chromatographed on a silica gel column (LPS-1), eluting the column with EtOAc:Hexane mixtures (1:7; 1:4). The desire fractions were combined and evaporated to give title compound as a colorless oil (348.8 mg, 96%).

TLC: $R_f$ 0.12 (Silica gel; EtOAc:Hexane-1:4).

F. [1R-(1α,2α,4α)]-2-](2,2-Dimethyl-1-oxobutoxy)methyl]-7-oxabicyclo[2.2.1]heptane-1-carboxaldehyde A solution of Dess-Martin periodinane (917.6 mg, 2.10 mmole, 1.5 eq.) and t-butyl alcohol (0.21 mL, 1.5 eq.) in dry dichloromethane (6.7 mL) was stirred at room temperature under nitrogen for 15 minutes, treated with a solution of Part E compound (348.8 mg, 1.36 mmole) in dry dichloromethane (6.7 mL), and continued stirring at room temperature for 20 hours. The reaction mixture was then diluted with dichloromethane (85 mL), and poured into a solution of Na$_2$S$_2$O$_3$ (3.62 g, 7-fold excess) in 1N NaHCO$_3$ (20 mL), stirring the mixture until the precipitates went into solution. The aqueous phase was re-extracted with dichloromethane (2×85 mL) and the combined organic extracts were washed with brine (25 mL), dried (anhydrous MgSO$_4$), filtered and evaporated to dryness. The crude product (348.6 mg) was chromatographed on a silica gel column (LPS-1), eluting the column with EtOAc:Hexane (1:4). The desired fractions were combined and evaporated to dryness to give title compound as a colorless oil (291.5 mg, 84.2%).

TLC: $R_f$ 0.67 (Silica gel; EtOAc:Hexane-1:1).

G. [1S-[1α(R*,E),2α,4α]]-3-[[(1,1-Dimethylethyl)dimethylsilyl]oxy]-7-[2-[(2,2-dimethyl-1-oxobutoxy)methyl]-7-oxabicyclo[2.2.1]hept-1-yl]-5-oxo-6-heptenoic acid, methyl ester (R)-6-(Dimethoxyphosphinyl)-3-[[(1,1-dimethylethyl)dimethylsilyl]oxy]-5-oxo-hexanoic acid, methyl ester (586.0 mg, 1.58 mmole) was dissolved in dry acetonitrile (8.0 mL) and treated successively with dry LiCl (64 mg), 1,8-diazabicyclo [5.4.0]undec-7-ene (DBU) (96%, 190 μL) and a solution of Part F compound (291.5 mg, 1.14 mmole) in dry acetonitrile (8.0 mL). The mixture became cloudy within 10 minutes and was stirred at room temperature under argon for 20 hours, quenched with 5% KHSO$_4$ and extracted with ethyl acetate (3×75 mL). The combined organic extracts were washed with saturated NaHCO$_3$ (12 mL), brine (20 mL), dried (anhydrous MgSO$_4$), filtered and evaporated to dryness. The crude product (784.1 mg) was chromatographed on a silica gel column (LPS-1), eluting the column with EtOAc:Hexane (1:4). The desired fractions were combined and evaporated to give title compound as a colorless oil (570 mg, 97.9%).

TLC: R$_f$ 0.32 (Silica gel; EtOAc:Hexane-1:4).

H.  [1S-[1α(R*),2α,4α]]-β-[[(1,1-Dimethylethyl)dimethylsilyl]oxy]-2-[(2,2-dimethyl-1-oxobutoxy)methyl]-δ-oxo-7-oxabicyclo[2.2.1]heptane-1-heptanoic acid, methyl ester A solution of Part G compound (570 mg, 1.12 mmole) in dry methanol (50 mL) was treated with 10% Pd/C (50 mg) and hydrogenated at room temperature. The reaction mixture, upon completion, was filtered through a Celite pad in a millipore unit, washing the pad well with methanol. The clear filtrate was evaporated to dryness to give title compound as a colorless oil (539.7 mg, 94.5%).

TLC: R$_f$ 0.77 (Silica gel; EtOAc:Hexane-1:1).

I.  [1S-[1α(R*),2α,4α]]-2-[(2,2-Dimethyl-1-oxobutoxy)-methyl-β-hydroxy-δ-oxo-7-oxabicyclo[2.2.1]heptane-1-heptanoic acid, methyl ester A solution of Part H compound (488.5 mg, 0.95 mmole) in dry tetrahydrofuran (25 mL) was treated with glacial acetic acid (0.44 mL, 7.28 mmole, 7.7 eq.), followed by 1 M (C$_4$H$_9$)$_4$NF/THF (5.7 mL, 5.46 mmole, 5.7 eq.) and stirred at room temperature under argon for 2.5 days. The reaction mixture was diluted with ice water (15 mL) and extracted with ether (3×100 mL). The combined organic extracts were washed with saturated NaHCO$_3$ (15 mL), brine (15 mL), dried (anhydrous MgSO$_4$), filtered and evaporated to dryness. The crude product (465 mg) was chromatographed on a silica gel column (LPS-1), eluting the column with EtOAc:Hexane mixtures (1:4; 1:1) to give title compound as a colorless oil (338.9 mg, 94.4%).

TLC: R$_f$ 0.47 (Silica gel; EtOAc:Hexane-1:1).

J.  [1R-[1α(βR*,δR*),2α,4α]]-2-[(2,2-Dimethyl-1-oxobutoxy)methyl]-β,δ-dihydroxy-7-oxabicyclo[2.2.1]heptane-1-heptanoic acid, methyl ester A solution of Part I compound (376.9 mg, 0.95 mmol) in dry tetrahydrofuran (14.0 mL) was treated with 1M (C$_2$H$_5$)$_3$B (1.40 mL, 1.42 mmole, 1.49 eq.), stirred at room temperature under argon for 30 minutes then cooled down to −78° (dry-ice-acetone). The cooled solution was treated with sodium borohydride (84 mg, 2.2 mole, 2.33 eq.), followed by the dropwise addition of methanol (3.5 mL) and the reaction mixture stirred at −78° for 2.0 hours. The mixture was quenched by treatment at −78° with 30% H$_2$O$_2$ (2.1 mL)-H$_2$O (7.0 mL), stirred for 15 minutes, warmed up to room temperature and stirred for another 30 minutes. The mixture was then diluted with water (10 mL) and extracted with ethyl acetate (3×100 mL). The combined organic extracts were washed with saturated NaHCO$_3$ (15 mL), brine (20 mL), dried (anhydrous MgSO$_4$), filtered and evaporated to dryness. The crude product was chromatographed on a silica gel column (LPS-1), eluting the column with EtOAc:Hexane (1:1). The desired fractions were combined to give title compound as a colorless oil (365.5 mg, 96.1%).

TLC: R$_f$ 0.18 (Silica gel; EtOAc:Hexane-1:1).

K.  [1R-[1α(βR*,δR*),2α,4α]]-2-[(2,2-Dimethyl-1-oxobutoxy)methyl]-β,δ-dihydroxy-7-oxabicyclo[2.2.1]heptane-1-heptanoic acid, monolithium salt A solution of Part J ester (365.5 mg, 0.91 mmole) in dioxane (7.0 mL) was treated with 1N LiOH (0.96 mL, 1.05 eq.) and stirred at room temperature under argon for 1.0 hour. The reaction mixture was stripped to dryness and the residual syrup dissolved with a minimum amount of water (~3.0 mL) and chromatographed on an HP-20 column (1"×3"), eluting the column with steam-distilled water (400 mL), followed by 50% aqueous CH$_3$OH (500 mL). The desired fractions were combined, evaporated to dryness. The residue was dissolved in water (30 mL) and lyophilized to give title salt as a fluffy solid (305.1 mg, 85.4%).

IR (1581 cm$^{-1}$, strong, C=O of —COO$^-$; 1727 cm$^{-1}$, strong, C=O of —COOR; 2969 cm$^{-1}$, strong, OH).

TLC: R$_f$ 0.27 (Silica gel; CH$_2$Cl$_2$-HOAc-CH$_3$OH-20:1:1).

Anal. Calc'd for C$_{20}$H$_{33}$O$_7$Li.0.5 H$_2$O: C, 59.84; H, 8.54

Found: C, 59.74; H, 8.34.

H$^1$-NMR Spectrum (270 MHz, CD$_3$OD): δ 0.86 (t, 3H, J = ~7), 1.24 (s, 6H), 1.43–1.82 (m, 13H), 1.94–2.42 (m, 4H), 3.69–3.83 (m, 2H), 4.05–4.19 (m, 2H), 4.46 (t, 1H, J = ~4).

EXAMPLE 4

1R-[1α(βR*,δR*),2α,4α]]-β,δ-Dihydroxy-2-[[methyl(-phenylmethyl)amino]carbonyl]-7-oxabicyclo[2.2.1]-heptane-1-heptanoic acid, monolithium salt A.  [1R-(1α,2α,4α)]-1-(Hydroxymethyl)-N-methyl-N-(phenylmethyl)-7-oxabicyclo[2.2.1]heptane-2-carboxamide A mixture of Example 2 Part D compound (300 mg, 1.76 mmole) and 0.33 m (CH$_3$)$_2$AlN(CH$_3$)CH$_2$C$_6$H$_5$ (30 mL, 1.75 g, 9.90 mmole) was refluxed under argon for 2.5 days. The mixture was cooled, treated dropwise with 5% KHSO$_4$ (23 mL) and extracted with ethyl acetate (2×100 mL). The combined organic extracts were washed with brine (20 mL), dried (anhydrous MgSO$_4$), filtered and evaporated to dryness. The crude product (899.7 mg) was chromatographed on a silica gel column (LPS-1), eluting the column with EtOAc:Hexane mixtures (1:1; 9:1) and ethyl acetate. The desired fractions were combined and evaporated to dryness to give title compound as a colorless oil (498.7 mg, 100%).

TLC: R$_f$ 0.19 (Silica gel; Acetone:Hexane-2:3).

B.  [1R-(1α,2α,4α)]-1-Formyl-N-methyl-N-(phenylmethyl)-7-oxabicyclo[2.2.1]heptane-2-carboxamide A mixture of Dess-Martin periodinane (764 mg, 1.8 mmole, ~1.5 eq.) and t-butyl alcohol (0.17 mL, 1.5 eq.) in dry dichloromethane (15 mL) was stirred at room temperature for 15 minutes under argon and treated with a solution of Part A compound (330 mg, 1.2 mmole) in dry dichloromethane (15 mL). The mixture was stirred for another 21 hours, diluted with dichloromethane (100 mL), then poured into a solution of Na$_2$S$_2$O$_3$ (3.0 g, 7-fold excess) in 1N NaHCO$_3$ (16 mL), stirring the suspension until all the precipitates went into solution. The aqueous phase was extracted two more times with dichloromethane (100 mL) and the combined organic extracts were washed with brine (20 mL), dried (anhydrous MgSO$_4$), filtered and evaporated to dryness. The crude product (392.4 mg) was chromatographed on a silica gel column (LPS-1), eluting the column with EtOAc:Hexane (1:1). The desired fractions were combined and evaporated to give title compound as a colorless oil (261.3 mg, 79.8%).

TLC: R$_f$ 0.43 (Silica gel; Acetone:Hexane-2:3).

C. [1S-[1α(R*,E),2α,4α]]-3-[[(Dimethylethyl)dimethylsilyl]oxy]-7-[2-[[methyl(phenylmethyl)amino]carbonyl]-5-oxo-7-oxabicyclo[2.2.1]hept-1-yl]-6-heptenoic acid, methyl ester A solution of (R)-6-(dimethoxyphosphinyl)-3-[[(1,1-dimethylethyl)dimethylsilyl]oxy]-5-oxo-hexanoic acid, methyl ester (492.3 mg, 1.33 mmole) in dry acetonitrile (6.7 mL) was treated successively with lithium chloride (56 mg, 1.32 mmole), 1,8-diazabicyclo[5.4.0]undec-7-ene (96%, 160 μL) and a solution of Part B compound (261.8 mg, 0.96 mmole) in dry acetonitrile (7.3 mL) under argon. The reaction mixture became cloudy within 10 minutes, was stirred for 19 hours at room temperature, then partitioned between 5% KHSO$_4$ (13 mL) and ethyl acetate (3×100 mL). The combined organic extracts were washed with saturated NaHCO$_3$ (10 mL), brine (20 mL), dried (anhydrous MgSO$_4$), filtered and evaporated to dryness. The crude product (607.4 mg) was chromatographed on a silica gel column (LPS-1), eluting the column with EtOAc:Hexane mixtures (1:2; 1:1). The desired fractions were combined and evaporated to give title compound as a colorless oil (424.6 mg, 83.5%).

TLC: R$_f$ 0.52 (Silica gel; Acetone:Hexane-2:3).

D. [1S-[1α(R*),2α,4α]]-β-[[(Dimethylethyl)dimethylsilyl]oxy]-2-[[methyl(phenylmethyl)amino]carbonyl]-δ-oxo-7-oxabicyclo[2.2.1]-heptane-1-heptanoic acid, methyl ester A solution of Part C compound (424.6 mg, 0.80 mmole) in dry methanol (50 mL) was treated with 5% Pd/C (50 mg) and hydrogenated at room temperature. The reaction mixture, upon completion, was diluted with methanol (50 mL) and filtered through a Celite pad in a millipore unit, washing the pad well with methanol. The clear filtrate was evaporated to give title compound as a colorless oil (390 mg, 91.7%).

TLC: R$_f$ 0.55 (Silica gel; Acetone:Hexane-2:3).

E. [1S-[1α(R*),2α,4α]]-β-Hydroxy-2-[[methyl(phenylmethyl)amino]carbonyl]-δ-oxo-7-oxabicyclo[2.2.1]heptane-1-heptanoic acid, methyl ester A solution of Part D compound (390 mg, 0.73 mmole) in dry tetrahydrofuran (25 mL) was treated with glacial acetic acid (0.38 mL, 6.29 mmole, 8.6 eq.) followed by 1N (C$_4$H$_9$)$_4$NF/THF (4.98 mL, 4.77 mmole, 6.5 eq.) and stirred at room temperature under argon for 2.5 days. The reaction mixture was diluted with ice water (15 mL) and extracted with ethyl acetate (3×100 mL). The combined organic extracts were washed with saturated NaHCO$_3$ (8.0 mL), brine (15 mL), dried (anhydrous MgSO$_4$), filtered and evaporated to dryness. The crude product (~500 mg) was chromatographed on a silica gel column (LPS-1), eluting the column with Acetone:CH$_2$Cl$_2$ mixtures (1:6; 1:4). The desired fractions were combined to give title compound as a colorless oil (285.2 mg, 93.6%).

TLC: R$_f$ 0.28 (Silica gel; Acetone: CH$_2$Cl$_2$-1:4).

F. [1R-[α(βR*,δR*),2α,4α]]-β,δ-Dihydroxy-2-[[methyl(phenylmethyl)amino]carbonyl]-7-oxabicyclo[2.2.1]heptane-1-heptanoic acid, methyl ester A solution of Part E compound (285.2 mg, 0.68 mmole) in dry tetrahydrofuran (10 mL) was treated with 1M (C$_2$H$_5$)$_3$B (1.0 mL, 1.0 mmole, 1.47 eq.) at room temperature for 30 minutes under argon then cooled down to −78° (dry ice-acetone). The cooled solution was treated with sodium borohydride (60 mg, 1.59 mmole, 2.33 eq.) followed by the dropwise addition of dry methanol (2.5 mL) and the reaction mixture stirred at −78° for 2 hours. The mixture was quenched by treatment at −78° with 30% H$_2$O$_2$ (1.5 mL)-H$_2$O (5.0 mL), stirred for 15 minutes, warmed up to room temperature and stirred for another 30 minutes. The mixture was then diluted with water (10 mL) and extracted with ethyl acetate (3×100 mL). The combined organic extracts were washed with saturated NaHCO$_3$ (12 mL), brine (15 mL), dried (anhydrous MgSO$_4$), filtered and evaporated to dryness. The crude product (298.5 mg) was chromatographed on a silica gel column (LPS-1), eluting the column with Acetone:CH$_2$Cl$_2$ mixtures (1:3; 1:1; 4:1). The desired fractions were combined and evaporated to give title ester as a colorless oil (267.0 mg, 93.6%).

TLC: R$_f$ 0.12 (Silica gel; Acetone: CH$_2$Cl$_2$-1:3).

G [1R-[1α(βR*,δR*),2α,4α]]-β,δ-Dihydroxy-2-[[methyl(phenylmethyl)amino]carbonyl]-7-oxabicyclo[2.2.1]heptane-1-heptanoic acid, monolithium salt A solution of Part F ester (267.0 mg, 0.64 mmole) in dioxane (3.4 mL) was treated with 1N LiOH (0.66 mL, 0.66 mmole or 1.03 eq.) and stirred at room temperature under argon for 1.0 hour. The reaction mixture was evaporated to dryness and the residual syrup dissolved in H$_2$O (~5 mL) and chromatographed on an HP-20 column (1"×3"), eluting the column with steam-distilled water (400 mL), followed by 50% aqueous methanol (500 mL). The desired fractions were combined, evaporated to dryness. The residue was dissolved in steam distilled water (~25 mL) and lyophilized to give title salt as light, fluffy solid.

IR (1586 cm$^{-1}$, strong, C=O of COO$^-$; 1617 cm$^{-1}$, strong, C=O of —CONR$_2$; 3415 cm$^{-1}$, strong, —OH).

TLC: R$_f$ 0.50 (Silica gel; CH$_2$Cl$_2$:CH$_3$OH:HOAc-20:1:1).

Anal. Calc'd for C$_{22}$H$_{30}$NO$_6$Li.0.6 H$_2$O: C, 62.58; H, 7.45; N, 3.32

Found: C, 62.32; H, 7.56; N, 3.42.

H$^1$-NMR Spectrum (270 MHz, CD$_3$OD): δ 1.36–1.93 (m, 12H), 1.98–2.16 (m, 2H), 2.21–2.42 (m, 2H), 2.97 (s, 1H), 3.06 (s, 2H), 3.09–3.22 (m, 2H), 3.68–3.81 (m, 1H), 4.09 (quint, 1H), 4.45–4.62 (m, 2H), 7.17–7.41 (m, 5H).

EXAMPLE 5

[1R-[1α(βR*,δR*),2α,4α]]-2-[[(2,2-Dimethyl-1-oxobutyl)methylamino]methyl]-β,δ-dihydroxy-7-oxabicyclo[2.2.1]heptane-1-heptanoic acid, monolithium salt A. [1R-(1α,2α,4α)]-2-[[Methyl(phenylmethyl)amino]methyl]-7-oxabicyclo[2.2.1]-heptane-1-methanol A solution of Example 4, Part A compound (249 mg, 0.90 mmole) in dry tetrahydrofuran (20 mL) was treated with 95+% lithium aluminum hydride (LAH) (50 mg, 1.25 mmole) and refluxed under argon for 2.5 hours. The mixture was cooled, quenched by the sequential addition of H$_2$O (0.05 mL), 10% NaOH (0.075 mL) and water (0.15 mL) and stirred for 30 minutes. The mixture was diluted with CH$_2$Cl$_2$ (50 mL), treated with a small amount of Celite and filtered through a millipore unit, washing the pad well with CH$_2$Cl$_2$ (50 mL). The filtrate and washings were evaporated to dryness to give the crude product (242.8 mg) containing traces of three more polar components. The product mixture was chromatographed on a silica gel column (LPS-1), eluting the column with EtOAc:hexane mixture (1:1; 1.5 liters). The desired fractions were combined and evaporated to dryness to give title compound as a colorless oil (179.8 mg, 76.4% yield).

TLC: $R_f$ 0.49 (Silica gel; Acetone:Hexane-2:3).

B.  [1R-(1α,2α,4α)]-2-[(Methylamino)methyl]-7-oxabicyclo[2.2.1]heptane-1-methanol A solution of Part A compound (354.2 mg, 1.36 mmole) in dry methanol (40 mL) was treated with 5% Pd/C (40 mg) and hydrogenated at room temperature. The reaction mixture, upon completion, was diluted with methanol (50 mL) and filtered through a millipore unit, washing the catalyst well with methanol. The combined organic filtrates were evaporated to dryness and dried in vacuo to give title compound as a thick oil (234.6 mg, 100% crude yield).

TLC: $R_f$ 0.08 (Silica gel; $CH_2Cl_2$:MeOH-7:3).

C.  [1R-(1α,2α,4α)]-2-[[(2,2-Dimethyl-1-oxobutyl)methylamino]methyl]-7-oxabicyclo[2.2.1]heptane-1-methanol A solution of Part B compound (230 mg, 1.34 mmole) in dry dichloromethane (15 mL) was treated with dimethylaminopyridine (34 mg) and triethylamine (0.55 mL, 3.99 mmole). The mixture was cooled down to 0° C. (ice bath), treated with a solution of dimethylbutyryl chloride (390 mg, 2.91 mmole) or 2.2 eq.) in dry dichloromethane (4.2 mL), warmed up to room temperature and stirred under $N_2$ for 26 hours. The mixture was diluted with $CH_2Cl_2$ (100 mL), washed with 5% HCl (10 mL). The acid wash was back-extracted two more times with $CH_2Cl_2$ (100 mL). The combined organic extracts were washed with brine (20 mL), dried (anhydrous $MgSO_4$), filtered and evaporated to dryness. The crude product mixture (476.1 mg) was chromatographed on silica gel column (Baker, 60-200 mesh, 50 mL), eluting the column with Acetone:Hexane mixtures (1:4, 1:1). The fractions containing the diacylated product were combined and evaporated to dryness.

The crude product (290 mg, 0.83 mmole) was dissolved in dioxane (10 mL), treated with 1N LiOH (2.5 mL, ~59.8 mg or 3 eq.) and stirred under $N_2$ for 2.5 days. The crude mixture was evaporated to remove most of the dioxane then partitioned between 5% $KHSO_4$ (10 mL) and ethyl acetate (3×100 mL). The combined organic extracts were washed with brine (15 mL), dried (anhydrous $MgSO_4$), filtered and evaporated to dryness. The crude product was chromatographed on a silica gel column (LPS-1), eluting the column with EtOAc:hexane (1:1). The desired fractions were combined and evaporated to dryness to give title compound as a colorless oil (155.3 mg, 43.0%).

TLC: $R_f$ 0.32 (Silica gel; Acetone:Hexane-2:3).

D.  [1R-(1α,2α,4α)]-2-[[(2,2-Dimethyl-1-oxobutyl)methylamino]methyl]-7-oxabicyclo[2.2.1]heptane-1-carboxaldehyde A solution of the Dess-Martin periodinane (367.2 mg, 0.87 mmole, 1.5 eq.) and t-butanol (80 μL, 1.5 eq.) in dry dichloromethane (5.0 mL) was stirred under argon for 15 minutes at room temperature then treated with a solution of Part C compound (155 mg, 0.58 mmole) in dry dichloromethane (8.0 mL), and stirred for an additional 20 hours under argon. The reaction mixture was diluted with dichloromethane (50 mL), poured into a solution of $Na_2S_2O_3$ (1.44 g, 7-fold excess) in 1N $NaHCO_3$ (8.0 mL), and stirred until the precipitates went into solution. The aqueous solution was separated from the organic phase, extracted with dichloromethane (2×50 mL) and the combined organic extracts were washed with brine (10 mL), dried (anhydrous $MgSO_4$), filtered and evaporated to dryness. The crude product (250 mg) was chromatographed on a silica gel column (LPS-1), eluting the column with EtOAc:Hexane (1:4) to give title compound as a colorless oil (127.0 mg, 81.9%).

TLC: $R_f$ 0.48 (Silica gel; Acetone:Hexane-2:3).

E.  [1S-[1α(R*,E),2α,4α]]-3-[[(1,1-Dimethylethyl)dimethylsilyl]oxy]-7-[2-[[(2,2-dimethyl-1-oxobutyl)methylamino]methyl-5-oxo-7-oxabicyclo[2.2.1]hept-1-yl]-6-heptenoic acid, methyl ester (R)-6-(Dimethoxyphosphinyl)-3-[[(1,1-dimethyl)dimethylsilyl]oxy]-5-oxo-hexanoic acid, methyl ester (244.1 mg, 0.66 mmole) was dissolved in dry acetonitrile (3.5 mL) and treated successively with dry LiCl (27 mg), 1,8-diazabicyclo [5.4.0]undec-7-ene (96%, 80 μL) and a solution of Part D compound (127.0 mg, 0.47 mmole) in dry acetonitrile (4.5 mL). The mixture became cloudy within 10 minutes and was stirred at room temperature under argon for 20 hours, quenched with 5% $KHSO_4$ and extracted with ethyl acetate (3×40 mL). The combined organic extracts were washed with saturated $NaHCO_3$ (6.0 mL), brine (6.0 mL), dried (anhydrous $MgSO_4$), filtered and evaporated to dryness. The crude product (304.7 mg) was chromatographed on a silica gel column (LPS-1), eluting the column with EtOAc:Hexane mixtures (1:4; 1:1). The desired fractions were combined and evaporated to give title compound as a colorless oil (224.3 mg, 91.1%).

TLC: $R_f$ 0.48 (Silica gel; EtOAc:Hexane-1:1).

F.  [1S-[1α(R*), 2α,4α]]-β-[[(1,1-Dimethylethyl)dimethylsilyl]oxy]-2-[[(2,2-dimethyl-1-oxobutyl)methylamino]methyl]-δ-oxo-7-oxabicyclo[2.2.1]heptane-1-heptanoic acid, methyl ester A solution of Part E compound (224.3 mg, 0.43 mmole) in dry methanol (25 mL) was treated with 5% Pd/C (20 mg) and hydrogenated at room temperature. The reaction mixture, upon completion was diluted with methanol (25 mL) and filtered through a millipore unit, washing the pad well with methanol. The clear filtrate was evaporated to dryness to give title compound as a colorless oil (223.5 mg, 98.9%).

TLC: $R_f$ 0.50 (Silica gel; EtOAc:Hexane-1:1).

G.  [1S-[1α(R*),2α,4α]]-2-[[(2,2-Dimethyl-1-oxobutyl)methylamino]methyl]-β-hydroxy-δ-oxo-7-oxabicyclo[2.2.1]heptane-1-heptanoic acid, methyl ester A solution of Part F compound (223.5 mg, 0.43 mmole) in dry tetrahydrofuran (12 mL) was treated with glacial acetic acid (0.2 mL, 3.44 mmole, 8 eq.) followed by 1M $(C_4H_9)_4NF$/THF (2.55 mL, 2.58 mmole, 6 eq.) and stirred at room temperature under argon for 2.5 days. The reaction mixture was diluted with ice water (8.0 mL) and extracted with ether (3×100 mL). The combined organic extracts were washed with saturated $NaHCO_3$ (7.0 mL), brine (7.0 mL), dried (anhydrous $MgSO_4$), filtered and evaporated to dryness. The crude product (~900 mg) was chromatographed on a silica gel column (LPS-1), eluting the column with EtOAc:hexane mixtures (1:1; 4:1) to give title compound as a colorless oil (156.8 mg, 88.6%).

TLC: $R_f$ 0.08 (Silica gel; EtOAc:Hexane-1:1).

H.  [1R-[1α(βR*,δR*),2α,4α]]-2-[[(2,2-Dimethyl-1-oxobutyl)methylamino]methyl]-β,δ-dihydroxy-7-oxabicyclo[2.2.1]heptane-1-heptanoic acid, methyl ester A solution of Part G compound (156.8 mg, 0.38 mmole) in dry tetrahydrofuran (5.6 mL) was treated with 1M $(C_2H_5)_3B$ (0.56 mL, 0.568 mmole, 1.49 eq.), stirred at room temperature under argon for 30 minutes then cooled down to $-78°$ C. (dry ice-acetone). The cooled solution was treated with sodium borohydride (34 mg, 0.89 mmole, 2.34 eq.), followed by the dropwise addition of methanol (1.4 mL) and the reaction mixture stirred at $-78°$ C. for 2.0 hours. The mixture was quenched by treatment at $-78°$ C. with 30% $H_2O_2$ (0.84 mL)-$H_2O$ (2.8 mL), stirred for 15 minutes, warmed up to room temperature and stirred for another 30 minutes. The mixture was then diluted with water (6 mL) and extracted with ether (3×60 mL). The combined organic extracts were washed with saturated $NaHCO_3$ (6 mL), brine (8 mL), dried (anhydrous $MgSO_4$), filtered and evaporated to dryness to give title ester as a colorless oil (159.5 mg, 100% crude yield).

TLC: $R_f$ 0.17 (Silica gel; EtOAc:hexane-9:1).

I. [1R-[1α(βR*,δR*),2α,4α]]-2-[[(2,2-Dimethyl-1-oxobutyl)methylamino]methyl]-β,δ-dihydroxy-7-oxabicyclo[2.2.1]heptane-1-heptanoic acid, monolithium salt A solution of Part H ester (159.5 mg, 0.38 mmole) in dioxane (2.0 mL) was treated with 1N LiOH (1.56 mL, ~4 eq.) and stirred at room temperature under argon for 1.0 hour. The reaction mixture was stripped to dryness and dried in vacuo (pump) for 1.0 hour. The residue was dissolved in a minimum amount of water (~3.0 mL) and chromatographed on an HP-20 column (1"×2.5"), eluting the column with steam-distilled water (250 mL), followed by 5% aqueous $CH_3CN$ (200 mL), 20% aqueous $CH_3CN$ (200 mL) and 50% aqueous $CH_3CN$ (200 mL). The desired fractions were combined, evaporated to dryness. The residue was dissolved in water (10 mL) and lyophilized to give title salt as a fluffy solid (147.0 mg, 95.3%).

IR (1586 cm$^{-1}$, strong, C=O of —COO$^-$; 1612 cm$^{-1}$, strong, C=O of —CONR; 2968 cm$^{-1}$, strong, —OH).

TLC: $R_f$ 0.10 (Silica gel; $CH_2Cl_2$:MeOH:HOAc-20:1:1).

Anal. Calc'd for $C_{21}H_{36}NO_6Li \cdot 1.3\ H_2O$: C, 58.81; H, 9.07; N, 3.26

Found: C, 58.78; H, 9.31; N, 3.17.

H$^1$-NMR Spectrum (270 MHz, CD$_3$OD): δ 0.86 (t, 3H, J=~7), 1.23 (s, 6H), 1.43–1.78 (m, 15H), 1.97–2.10 (m, 1H), 2.21–2.41 (m, 3H), 3.06 (s, 3H), 3.13–3.39 (m, 1H), 3.53–3.81 (m, 2H), 4.12 (quint, 1H), 4.44 (t, 1H, J=~4).

EXAMPLE 6

[1S-[1α(3R*,5S*,6E),2α,4α]]-7-[2-[(Phenylmethoxy)methyl]-7-oxabicyclo[2.2.1]hept-1-yl]-3,5-dihydroxy-6-heptenoic acid, monolithium salt A. [1R-(1α,2α,4α)]-2-[(Phenylmethoxy)methyl]-7-oxabicyclo[2.2.1]heptane-1-methanol and
B. [1R-(1α,2α,4α)]-1-[(Phenylmethoxy)methyl]-7-oxabicyclo[2.2.1]heptane-2-methanol To a solution of Example 3, Part C alcohol (0.537 g, 1.97 mmole) in dry THF (6.0 mL) at 0° C. under argon was added 60% NaH-oil dispersion (0.120 g, 3.0 mmole). After stirring at 0° C. for 1 hour, benzylbromide (350 μL, 2.94 mmole) and tetrabutyl-ammonium iodide (0.045 g) were added, the mixture warmed to room temperature and stirred for 20 hours. The mixture was then partitioned between EtOAc-5% $KHSO_4$, the organic phase washed with saturated $NaHCO_3$ and saturated NaCl solutions, dried over $Na_2SO_4$ and evaporated to dryness. TLC (EtOAc-hexane; 1:4) shows two isomeric product spots $R_f$=0.43 (major) and 0.39 (minor). Flash chromatography on silica gel (60 g, LPS-1) eluting with EtOAc-hexane (5:95) gave two fractions:0.444 g (>95% major isomer) and 0.106 g (major:minor; 1:4).

Each of these fractions was desilylated separately with 48% HF-acetonitrile. Thus, the major product (0.444 g) was dissolved in acetonitrile (6.0 mL) and treated with 48% aqueous HF (0.22 mL, 6.1 mmole). The minor fraction (0.106 g) was likewise dissolved in acetonitrile (2.0 mL) and treated with 48% aqueous HF (0.05 mL, 1.39 mmole). After 1.5 hours, each mixture was diluted with EtOAc, washed with saturated NaHCO$_3$ and saturated NaCl solutions, dried over $Na_2SO_4$ and evaporated to dryness. The product from the major silyl ether was chromatographed on silica gel (20 g, LPS-1) eluting with EtOAc-hexane (2:8) to give pure A (0.280 g) as a colorless oil, TLC (EtOAc-hexane; 1:4) $R_f$=0.11. Likewise, chromatography of the product from the minor silyl ether on silica gel (15 g, LPS-1) eluting with EtOAc-hexane (35:65) gave an additional 0.015 g of A (total: 0.295 g, 60% overall) and B (0.053 g, 11% overall) as a colorless oil, TLC EtOAc-hexane; 1:4) $R_f$=0.07.

A:
$^1$H NMR (CD$_3$CN, 270 MHz) δ 1.16 (1H, m), 1.30–1.80 (5H, m), 2.15 (1H, m), 3.02 (1H, t, exchanges with D$_2$O), 3.10 (1H, dd), 3.40 (1H, t), 3.65 (1H, dd, becomes AB d with D$_2$O exchange), 3.84 (1H, dd, becomes AB d with D$_2$O exchange), 4.38 (1H, t), 4.47 (2H, s), 7.33 (5H, m).

B:
$^1$H NMR (CD$_3$CN, 270 MHz) δ 1.28 (1H, m), 1.43–1.73 (5H, m), 1.95 (1H, m), 2.81 (1H, t, exchanges with D$_2$O), 3.15 (1H, m, becomes dd with D$_2$O exchange), 3.43 (1H, m, becomes dd with D$_2$O exchange), 3.82 (2H, AB q), 4.39 (1H, m), 4.55 (2H, s), 7.33 (5H, m).

C. [1R-(1α,2α,4α)]-2-[(Phenylmethoxy)methyl]-7-oxabicyclo[2.2.1]heptane-1-carboxaldehyde To a solution of Dess-Martin periodinane (1.006 g, 2.37 mmole) and t-butanol (225 μL, 2.39 mmole) in $CH_2Cl_2$ (6.0 mL) was added a solution of Part A alcohol (0.290 g, 1.17 mmole) in $CH_2Cl_2$ (2 mL). After stirring at room temperature for 3.5 hours, the mixture was diluted with $CH_2Cl_2$ (50 mL) and poured onto a solution of $Na_2S_2O_3$ (2.62 q, 16.6 mmole) in 1.0N NaHCO$_3$ solution (20 mL, 20 mmole) and stirred vigorously for 15 minutes. The organic phase was separated, dried over $Na_2SO_4$ and evaporated to dryness. The crude product was purified by flash chromatography on silica gel (15 g, LPS-1) eluting with EtOAc-hexane (15:85) to give title aldehyde (0.252 g, 88%) as a colorless oil.

TLC (EtOAc-hexane; 4:6) $R_f$=0.41 ($R_f$ of A=0.23).
$^1$H NMR (CD$_3$CN, 270 MHz) δ 1.28 (1H, m), 1.50–1.83 (5H, m), 2.50 (1H, m), 3.17 (1H, dd), 3.28 (1H, t), 4.40 (2H, s), 4.56 (1H, t), 7.30 (5H, m), 9.83 (1H, s).

D. [1S-[1α(R*,E),2α,4α]]-3-[[(1,1-Dimethylethyl)dimethylsilyl]oxy]-5-oxo-7-[2-[(phenylmethoxy)methyl]-7-oxabicyclo[2.2.1]hept-1-yl]-6-heptenoic acid, methyl ester To a solution of (R)-6-(dimethoxyphosphinyl)-3-[[(1,1-dimethylethyl)dimethylsilyl]oxy]-5-oxo-hexanoic acid, methyl ester (0.545 g, 1.43 mmole) in dry acetonitrile (6.0 mL) at room temperature under argon was successively anhydrous LiCl (0.060 g, 1.43 mmole), DBU (160 μL, 1.07 mmole) and a solution of Part C aldehyde (0.252 g, 1.02 mmole) in dry acetonitrile (2.0 mL). After 15 minutes, the LiCl has gone into solution and a cloudy precipitate begins to form. After stirring at room temperature for 18 hours, the mixture was partitioned between EtOAc-5% $KHSO_4$, the organic phase washed with 5% $KHSO_4$, saturated $NaHCO_3$, and saturated NaCl solutions, dried over $Na_2SO_4$ and evaporated to dryness. The crude product was purified by flash chromatography on silica gel (20 g, LPS-1) eluting with EtOAc-hexane (15:85) to give title enone (0.513, 100%) as a colorless oil.

TLC (EtOAc-hexane; 4:6) $R_f$=0.57 ($R_f$ of Part C aldehyde=0.41).

E. [1S-[1α(R*,E),2α,4α]]-3-Hydroxy-5-oxo-7-[2-[(phenylmethoxy)methyl]-7-oxabicyclo[2.2.1]hept-1-yl]-6-heptenoic acid, methyl ester To a solution of Part D enone (0.513 g, 1.02 mmole) in dry THF (8.0 mL) was added successively acetic acid (460 μL, 8.04 mmole) and 1.0M tetrabutylammonium fluoride-THF (6.0 mL). After stirring at room temperature for 4 days, the mixture was partitioned between EtOAc-5% $KHSO_4$ (50 mL each). The organic phase was washed with saturated $NaHCO_3$ and saturated NaCl solution, dried over $Na_2SO_4$ and evaporated to dryness. The crude product was purified by flash chromatography on silica gel (20 g, LPS-1) eluting with EtOAc-hexane (35:65) to give title enone-alcohol (0.388 g, 98%) as a colorless oil.

TLC (EtOAc-hexane; 4:6) $R_f$=0.26 ($R_f$ of Part D enone=0.54).

$^1$H NMR ($CD_3CN$, 270 MHz) δ 1.32 (1H, m), 1.55 (2H, m), 1.80 (3H, m), 2.27 (1H, m), 2.40 (2H, m), 2.70 (2H, m), 3.03 (1H, dd), 3.19 (1H, t), 3.34 (1H, d, exchanges with $D_2O$), 3.62 (3H, s), 4.33 (2H, s), 4.39 (1H, m), 4.48 (1H, t), 6.27 (1H, d), 7.15 (1H, d), 7.30 (5H, m).

F. [1S-[1α(3R*,5S*,6E),2α,4α]]-7-[2-[(Phenylmethoxy)methyl]-7-oxabicyclo[2.2.1]hept-1-yl]-3,5-dihydroxy-6-heptenoic acid, methyl ester A solution of trimethylacetic acid (0.006 g, 0.06 mmole) in 1.0M triethylborane-THF (1.20 mL, 1.20 mmole) was stirred at room temperature under argon for 1 hour. To this solution was added a solution of Part E keto-alcohol (0.388 g, 1.00 mmole) in dry THF (8 mL). After stirring at room temperature under argon for an additional 1 hour, the mixture was cooled to −78° C. (dry ice-EtOH bath) and treated successively with $NaBH_4$ (0.120 g, 3.17 mmoles) and methanol (2.0 mL, added dropwise). After stirring at −78° C. for 3 hours, the solution was treated dropwise with 30% $H_2O_2$ (2.4 mL)-water (8.0 mL) and allowed to warm to room temperature. After stirring at room temperature for 30 minutes, the mixture was partitioned between EtOAc-water. The organic phase was washed successively with 5% $KHSO_4$, saturated $NaHCO_3$ and saturated NaCl, dried over $Na_2SO_4$ and evaporated to dryness. The crude product was purified by flash chromatography on silica gel (20 g, LPS-1) eluting with acetone-hexane (3:7) to give title diol (0.317 g, 81%) as a colorless oil.

TLC (acetone-hexane; 4:6) $R_f$=0.24 ($R_f$ of Part E enone-alcohol=0 36).

$^1$H NMR ($CD_3CN$, 270 MHz) δ 1.35–1.80 (8H, m), 2.12 (1H, m), 2.38 (2H, m), 2.99 (1H, dd), 3.38 (1H, dd), 3.38 (1H, d, exchanges with $D_2O$), 3.60 (1H, d, exchanges with $D_2O$), 3.62 (3H, s), 4.10 (1H, m), 4.25 (1H, m, becomes q with $D_2O$ exchange), 4.40 (2H, AB, q), 4.43 (1H, t), 5.68 (1H, dd), 5.96 (1H, d), 7.30 (5H, m).

G. [1S-[1α(3R*,5S*,6E),2α,4α]]-7-[2-[(Phenylmethoxy)methyl]-7-oxabicylco[2.2.1]hept-1-yl]-3,5-dihydroxy-6-heptenoic acid, monolithium salt To a solution of Part F methyl ester (0.317 g, 0.813 mmole) in dioxane (3.0 mL) was added 1.0N LiOH (1.10 mL, 1.10 mmole) and the resulting solution stirred at room temperature under argon for 45 minutes. The solution was then evaporated to dryness and the crude product purified by chromatography on HP-20 (20 mL bed volume, 1 inch diameter column) eluting first with water (300 mL) then with methanol-water (50:50; 500 mL). The product containing fractions were combined and evaporated to dryness. The residue was taken up in water, filtered through a polycarbonate membrane and lyophilized to give title lithium salt (0.285 g, 92%) as a fluffy, white solid, mp 77–82° C. (becomes glass).

TLC (AcOH-MeOH-$CH_2Cl_2$; 1:1:20) $R_f$=0.15.

$[α]_D$= +19.1° (c=0.55, MeOH)

$^1$H NMR ($CD_3OD$, 270 MHz) δ 1.45–1.85 (8H, m), 2.15 (1H, m), 2.30 (2H, m), 3.05 (1H, t), 3.45 (1H, dd), 4.05 (1H, m), 4.30 (1H, q), 4.39 (1H, AB d), 4.47 (1H, t), 4.49 (1H, AB d), 5.75 (1H, dd), 6.00 (1H, d), 7.30 (5H, m).

Anal. Calc'd for $C_{21}H_{27}O_6Li+0.52 H_2O$: C, 64.38; H, 7.21

Found: C, 64.39; H, 7.23.

EXAMPLE 7

1S-[1α(3R*,5S*,6E),2α,3α,4α]]-7-[2-[(2,2-Dimethyl-1-oxobutoxy)methyl]-3-[(phenylmethoxy)methyl]-7-oxabicyclo[2.2.1]hept-1-yl]-3,5-dihydroxy-6-heptenoic acid, monolithium salt A. (3aα,4α,7α,7aα)-2,3,3a,7a-Tetrahydro-4-hydroxymethyl-4,7-epoxyisobenzofuran-1,3(7aH)-dione A mixture of furfuryl alcohol (44.3 mL, 0.513 mole) and maleic anhydride (50.0 g, 0.510 mole) in $Et_2O$ (500 mL) was stirred at room temperature under argon for 5 days. The resulting precipitate was filtered off and washed thoroughly with $Et_2O$ and dried in vacuo to give the title anhydride (75.17 g, 75%) as a white crystalline solid, mp 84–86° C.

IR (nujol) 1870 and 1790 $cm^{-1}$.

$^1$H NMR ($d^6$-acetone, 270 MHz) δ 3.40 ppm (1H, AB d), 3.54 (1H, AB d), 3.98 (1H, AB d), 4.22 (1H, AB d), 5.34 (1H, s), 6.65 (2H,s).

B. (3aα,6α,7α,7aβ)-2,3,7,7a-Tetrahydro-1-oxo-3H-3a,6-epoxyisobenzofuran-7-carboxylic acid The Part A anhydride (75.17 g, 0.384 mole) in acetonitrile (500 mL) was treated with DMAP (2.0 g, 0.016 mole) and stirred at room temperature for 24 hours. The mixture was concentrated to about half the original volume, the precipitated product collected and washed with cold acetonitrile to give the title lactone-acid (45.16 g) as a buff colored, crystalline solid. Treatment of the mother liquor with charcoal, filtration (Celite) and concentration gave an additional 2.17 g of the title compound (total: 47.33 g, 63%). Recrystallization of a 0.10 g sample from acetonitrile-benzene gave 0.085 g of the pure title compound as white plates, mp 124–126° C.

TLC (AcOH-MeOH-$CH_2Cl_2$; 1:1:20) $R_f$=0.29.

IR (nujol) 1785 and 1710 $cm^{-1}$.

$^1$H NMR ($d^6$-acetone, 270 MHz) δ 2.80 ppm (1H, AB d), 3.10 (1H, AB d), 4.58 (1H, AB d), 4.90 (1H, AB d), 5.18 (1H, s), 6.58 (1H, AB d), 6.67 (1H, AB d), 10.85 (1H, broad s).

Anal. Calc'd for $C_9H_8O_5$: C, 55.11; H, 4.11 Found: C, 55.40; H, 4.17.

C. (3aα,6α,7α,7aα)-Hexahydro-1-oxo-3H-3a,6-epoxyisobenzofuran-7-carboxylic acid

A suspension of 10% Pt-C (1.5 g) in a solution of the Part B olefin (20.0 g, 102 mmole) in methanol (600 mL) was hydrogenated on a Parr apparatus at a pressure of 35 psi for 3 hours. The mixture filtered through Celite and evaporated to dryness. This reaction was repeated two more times using the same amounts of starting olefin, catalyst and solvent (total of 60.0 g, 306 mmole of starting olefin) The combined crude product of all three runs was triturated with EtOAc to give the title lactone acid (54.50 g, 90%) as a white crystalline solid. Concentration of the mother liquor yielded an additional crop of the title compound (3.65 g, total: 58.15 g, 96%) mp 191–193° C.

TLC (AcOH-MeOH-CH$_2$Cl$_2$; 1:1:20) R$_f$=0.29.

$^1$H NMR (d$^6$-acetone, 270 MHz) δ 1.65–2.10 (4H, m), 3.17 (1H, AB d), 3.36 (1H, AB d), 4.54 (2H, AB q), 4.75 (1H, d), 10.6 (1H, broad s).

Anal. Calc'd for C$_9$H$_{10}$O$_5$: C, 54.55; H, 5.09 Found: C, 54.46; H, 5.22.

D. [3aR-(3aα,6α,7α,7aβ)]-Hexahydro-1-oxo-3H-3a,6-epoxyisobenzofuran-7-carboxylic acid, (S)-α-methylbenzenemethanamine salt The following procedure was used for the large scale resolution of Part C lactone-acid. To a solution of Part C lactone-acid (20.0 g, 101 mmole) in methanol (600 mL) was added R(+) alpha-methylbenzylamine (13.0 mL, 101 mmole). After standing at room temperature for 3 hours, the crystallized salt was collected and washed with 150 mL of cold methanol to give 12.84 g of the less soluble R(+) amine salt. Evaporation of the mother liquor and trituration of the residue with ether gave 17.60 g of the more soluble R(+) amine salt. This salt (17.60 g) was dissolved in water (150 mL) and through an AG50-X8 (H+ form, 200 mL bed volume, 2 inch diameter column) eluting with water. The product containing fractions were combined and lyophilized to give 10.55 g of the partially resolved (+) lactone acid as a fluffy, white solid. This acid (10.55 g, 53.3 mmole) was taken up in methanol (400 mL) and treated with S(−) alpha-methylbenzylamine (7.0 mL, 54.3 mmole). After 2 hours, the crystallized product was collected to give title S(−) amine salt (11.36 g, 35% based on Part C compound) as white needles, mp 191–194° C.(d). [alpha]$_D$=−3.8° (c=0.55, MeOH). The structure of the title salt was determined by X-ray crystallography.

Anal. Calc'd for C$_{17}$H$_{21}$NO$_5$ C, 63.94; H, 6.63; N, 4.39 Found: C, 63.91; H, 6.66; N, 4.48.

E. [3aR-(3aα,6α,7α,7aα)]-Hexahydro-1-oxo-3H-3a,6-epoxyisobenzofuran-7-carboxylic acid A solution of the Part D resolved salt (11.36 g, 35.6 mmole) in water (250 mL) was passed through an AG50-X8 (H+ form, 200 mL bed volume, 2 inch diameter column) eluting with water. The product containing fractions were combined and lyophilized to give title compound as a fluffy, white solid. The product was taken up in methanol, evaporated and triturated with Et$_2$O to give title (+)-lactone acid (6.645 g, 94%) as white crystals, mp 182–184° C. [alpha]$_D$=+29.8° (c=0.63, MeOH).

TLC (AcOH-MeOH-CH$_2$Cl$_2$; 1:1:20) R$_f$=0.29.

$^1$H NMR (d$^6$-acetone, 270 MHz) δ 1.65–2.10 (4H, m), 3.17 (1H, AB d), 3.36 (1H, AB d), 4.54 (2H, AB q), 4.75 (1H, d), 10.6 (1H, broad s).

Anal. Calc'd for C$_9$H$_{10}$O$_5$: C, 54.55; H, 5.09 Found: C, 54.38; H, 5.05.

The optical purity of the title acid can be checked by conversion to its amide with S(−) alpha-methylbenzylamine. Thus, to a solution of (+)-lactone acid (0.062 g, 0.31 mmole) in CH$_2$Cl$_2$ (2 mL) at 0° C. under argon was added oxalyl chloride (40 μL, 0.46 mmole) and DMF (5 μL). The mixture was allowed to warm to room temperature, stirred for 1 hour and evaporated to dryness. The crude acid chloride was taken up in CH$_2$Cl$_2$ and treated successively with S(−) alpha-methylbenzylamine (45 μL, 0.35 mmole) and triethylamine (65 μL, 0.47 mmole) at 0° C. under argon. The mixture was allowed to warm to room temperature, stirred for 1 hour and partitioned between CH$_2$Cl$_2$-5% KHSO$_4$. The organic phase was dried over Na$_2$SO$_4$ and evaporated to dryness to give the amide (0.088 g, 93%) as a white crystalline solid.

TLC (MeOH-CH$_2$Cl$_2$; 1:9) single spot R$_f$=0.60.

$^1$H NMR (CD$_3$CN, 270 MHz) δ 1.36 (3H, d), 4.71 (1H, s). The S(−) alpha-methylbenzylamine-amide prepared from the racemic Part C acid showed two spots R$_f$'s=0.60 and 0.55 (isomers). $^1$H NMR (CD$_3$CN, 270 MHz) δ 1.36 (1.5H, d), 1.41 (1.5H, d), 4.62 (0.5H, d), 4.71 (0.5H, d).

F. [3aS-(3aα,4β,7β,7aα)]-Hexahydro-7-(hydroxymethyl)-4,7-epoxyisobenzofuran-1(7aH)-one To a suspension of Part E compound (6.30 g, 31.8 mmole) in dry CH$_2$Cl$_2$ (80 mL) at 0° C. under argon was added oxalyl chloride (3.50 mL, 40.1 mmole) and DMF (150 μL). The mixture was allowed to warm to room temperature, stirred for 2 hours and evaporated to dryness. The crude acid chloride was suspended in dry THF (100 mL), cooled in an ice bath and treated with LiAl(OC$_4$H$_9$-t)$_3$ (17.65 g, 69.3 mmole). After stirring at 0° C. for 1 hour and at room temperature for 2.5 hours, the mixture was placed in an ice bath and quenched with saturated Na$_2$SO$_4$ solution (15 mL). The mixture was dried over MgSO$_4$, filtered through Celite and evaporated to dryness. The crude product was purified by flash chromatography on silica gel (75 g, LPS-1) eluting with acetone-hexane (4:6) to give title alcohol (4.487 g, 77%) as a white, crystalline solid. Trituration with Et$_2$O gave title alcohol (4.267 g, 73%) as white crystals. Recrystallization of a 100 mg sample from EtOAc-hexane gave analytically pure title alcohol (85 mg) as white needles, mp 121–121.5° C.

[alpha]$_D$=−71.9° (c=0.51, CHCl$_3$).

TLC (MeOH-CH$_2$Cl$_2$; 1:9) R$_f$=0.59.

$^1$H NMR (CD$_3$CN, 270 MHz) δ 1.55–1.85 (4H, m), 1.90 (3H, m, 1H exchangeable with D$_2$O), 3.88 (2H, doublet of AB quartets, becomes AB quartet on D$_2$O exchange), 4.03 (1H, m), 4.40 (1H, m), 4.46 (1H, d).

Anal. Calc'd for C$_9$H$_{12}$O$_4$: C, 58.69; H, 6.57 Found: C, 58.70; H, 6.65.

G. [3aS-(3aα,4β,7β,7aα)]-7-[[[(1,1-Dimethylethyl)dimethylsilyl]oxy]methyl]hexahydro-4,7-epoxyisobenzofuran-1(7aH)-one To a solution of Part F lactone-alcohol (3.00 g, 16.3 mmole) and triethylamine (2.70 mL, 19.5 mmole) in dry CH$_2$Cl$_2$ (20 mL) was added t-butyldimethylsilyl chloride (17.9 mmole) and dimethylamino pyridine (DMAP) (0.39 g, 3.2 mmole). After stirring at room temperature for 4 hours, the mixture was washed with 5% KHSO$_4$, dried over Na$_2$SO$_4$ and evaporated to dryness. The crude product was purified by flash chromatography on silica gel (70 g, LPS-1) eluting with EtOAc-hexane (2:8) to give title alcohol (4.848 g, 100%) as a colorless oil TLC (acetone-Et$_2$O; 1:9) R$_f$=0.65 (R$_f$ of Part F compound=0.16).

$^1$H NMR (CD$_3$CN, 270 MHz) δ 0.07 ppm (3H, s), 0.08 (3H, s), 0.90 (9H, s), 1.44–1.88 (4H, m), 2.84 (2H, m), 3.93 (1H, AB d), 4.00 (1H, dd), 4.07 (1H, AB d), 4.35 (1H, t), 4.43 (1H, d).

H. [1R-(1α,3aα,4β,7β,7aα)]-7-[[[(1,1-Dimethylethyl)dimethylsilyl]oxy]methyl]-octahydro-4,7-epoxyisobenzofuran-1-ol To a solution of Part G lactone (4.828 g, 16.2 mmole) in dry toluene (60 mL) at −78° C. (dry ice-EtOH bath) under argon was added via syringe 1.0M DiBAL-heptane (24.5 mL, 24.5 mmole). After 2 hours at −78° C., TLC (EtOAc-hexane; 1:1) still shows unreacted starting material; an additional portion of 1.0M DiBAL-heptane (8.0 mL, 8.0 mmole) was added. After an additional 1 hour at −78° C., the reaction was quenched by the addition of silica gel (40 g, Merck) and water (5.0 mL) and the mixture allowed to warm to room temperature. After stirring at room temperature for 30 minutes, the mixture was filtered, the silica gel washed thoroughly with EtOAc and the combined filtrate evaporated to dryness. The crude product was purified by flash chromatography on silica gel (80 g, LPS-1) eluting with EtOAc-hexane (3:7) to give title lactol (4.543 g, 93.5%) as a white, crystalline solid, mp 50–51° C.

[alpha]$_D$= −13.6° (c=0.62, CHCl$_3$).

TLC (EtOAc-hexane; 1:1) R$_f$=0.21 (R$_f$ of Part G lactone=0.36).

Anal. Calc'd for C$_{15}$H$_{28}$O$_4$Si: C, 59.96; H, 9.39 Found: C, 59.97; H, 9.59.

I. [1R-(1α,2α,3α,4α)]-1-[[[(1,1-Dimethylethyl)dimethylsilyl]oxy]methyl]-2-ethenyl-7-oxabicyclo2.2.1]heptane-3-methanol To a suspension of methyl triphenylphosphonium bromide (17.88 g, 50.0 mmole) in dry THF (125 mL) at −78° C. under argon was added 1.6M n-C$_4$H$_9$Li-hexane (27.5 mL, 44 mmole) dropwise via syringe. After stirring at −78° C. for 0.5 hour and at 0° C. for 1 hour, Part H lactol (3.75 g, 12.5 mmole) was added to the yellow-orange ylide solution and the mixture allowed to warm to room temperature. After stirring at room temperature for 18 hours, the reaction was quenched by the addition of saturated NH$_4$Cl solution (8.0 mL) diluted with EtOAc (125 mL), dried over Na$_2$SO$_4$, filtered and evaporated to dryness. The crude product was purified by flash chromatography on silica gel (80 g LPS-1) eluting with EtOAc-hexane (25:75) to give title alcohol (3.498 g, 94%) as a colorless oil.

TLC (EtOAc-hexane; 3:2) R$_f$=0.53 (R$_f$ of Part H lactol=0.37).

J. [1R-(1α,2α,3α,4α)]-1-[[[(1,1-Dimethylethyl)dimethylsilyl]oxy]methyl]-2-ethenyl-3-[(phenylmethoxy)methyl]-7-oxabicyclo[2.2.1]heptane To a solution of Part I alcohol (2.50 g, 8.39 mmole) in dry THF (20 mL) at 0° C. under argon was added 60% NaH-oil dispersion (0.520 g, 13.0 mmole). After stirring at 0° C. for 0.5 hour, benzylbromide (1.50 mL, 12.6 mmole) and tetrabutylammonium iodide (0.20 g) were added, the mixture warmed to room temperature and stirred for 18 hours. The mixture was then partitioned between EtOAc-5% KHSO$_4$, the organic phase washed with saturated NaHCO$_3$ and saturated NaCl solutions, dried over Na$_2$SO$_4$ and evaporated to dryness. The crude product was purified by flash chromatography on silica gel (80 g, LPS-1) eluting with Et$_2$O-hexane (5:95) to give title benzyl ether (2.94 g, 90%) as a colorless oil.

TLC (Et$_2$O-hexane; 3:7) R$_f$=0.58.

K. [1R-(1α,2α,3α,4α)]-1-[[[(1,1-Dimethylethyl)dimethylsilyl]oxy]methyl]-3-[(phenylmethoxy)methyl]-7-oxabicyclo[2.2.1]heptane-2-methanol A solution of Part J olefin (2.94 g, 7.58 mmole) in methanol (50 mL) at −78° C. (dry ice-EtOH bath) was treated with ozone until the blue color of excess ozone was observed. Nitrogen was passed through the solution until the blue color was discharged and dimethylsulfide (2.75 mL) was added. After stirring at −78° C. for 1 hour and at 0° C. for 2 hours, the mixture was evaporated to dryness to give the crude aldehyde as a colorless oil.

TLC (EtOAc-hexane; 3:2) R$_f$=0.76 (R$_f$ of Part J olefin=0.89).

The crude aldehyde was taken up in dry THF (50 mL), cooled in an ice bath and treated with LiAl(OC$_4$H$_9$-t)$_3$H (4.83 g, 19.0 mmole) and then allowed to warm to room temperature. After stirring at room temperature for 1 hour, the mixture was placed in an ice bath and quenched with saturated Na$_2$SO$_4$ solution (15 mL). The mixture was dried over Na$_2$SO$_4$, filtered through Celite and evaporated to dryness. The crude product was purified by flash chromatography on silica gel (80 g, LPS-1) eluting with Et$_2$O-hexane (3:7) to give title alcohol (2.76 g, 93%) as a colorless oil.

TLC (EtOAc-hexane; 3:2) R$_f$=0.67.

L. [1R-(1α,2α,3α,4α)]-1-[[[(1,1-Dimethylethyl)dimethylsilyl]oxy]methyl]-3-[(phenylmethoxy)methyl]-7-oxabicyclo[2.2.1]heptane-2-methanol, 2,2-dimethylbutanoate To a solution of Part K alcohol (1.80 g, 4.59 mmole) in dry pyridine (10 mL) at 0° C. (ice bath) under argon was added 2,2-dimethylbutyryl chloride (0.95 g, 7.1 mmole) and DMAP (0.058 g, 0.48 mmole). After stirring at 0° C. for 15 minutes and at room temperature for 18 hours, the mixture was evaporated to dryness (30° C., 0.5 mmHg). The residue was taken up in EtOAc and washed successively with 5% KHSO$_4$, saturated NaHCO$_3$, saturated NaCl, dried over Na$_2$SO$_4$ and evaporated to dryness. The crude product was purified by flash chromatography on silica gel (85 g, LPS-1) eluting with Et$_2$O-hexane (5:95) to give title ester (2.057 g, 91%) as a colorless oil.

TLC (EtOAc-hexane; 2:8) R$_f$=0.51 (R$_f$ of Part K alcohol=0.27).

M. [1R-(1α,2α,3α,4α)]-2-[(2,2-Dimethyl-1-oxobutoxy)methyl]-3-[(phenylmethoxy)methyl]-7-oxabicyclo[2.2.1heptane-1-carboxaldehyde To a solution of Part L silyl ether (2.057 g, 4.20 mmole) in acetonitrile (20 mL) was added 48% aqueous HF (0.75 mL, 21 mmole). After stirring at room temperature for 1.5 hours, the mixture was diluted with EtOAc, washed with saturated NaHCO$_3$ and saturated NaCl solutions, dried over Na$_2$SO$_4$ and evaporated to dryness to give crude alcohol (1.79 g, theory: 1.59 g) as a colorless oil.

TLC (EtOAc-hexane; 1:4) R$_f$=0.07 (R$_f$ of Part L silyl ether=0.64).

To a solution of Dess-Martin periodinane (3.61 g, 8.51 mmole) and t-butanol (810 μL, 8.59 mmole) in CH$_2$Cl$_2$ (20 mL) was added a solution of crude alcohol (1.79 g, theory 1.59 g, 4.23 mmole) in CH$_2$Cl$_2$ (5 mL). After stirring at room temperature for 2 hours, the mixture was diluted with CH$_2$Cl$_2$ (50 mL) and poured onto a solution of Na$_2$S$_2$O$_3$ (9.37 g, 59.3 mmole) in 1.0N NaHCO$_3$ solution (70 mL, 70 mmole) and stirred vigorously for 15 minutes. The organic phase was separated, dried over Na$_2$SO$_4$ and evaporated to dryness. The crude product was purified by flash chromatography on silica gel (80 g, LPS-1) eluting with acetone-hexane (1:9) to give title aldehyde (1.26 g, 80% overall from Part J silyl ether) as a colorless oil.

TLC (EtOAc-hexane; 4:6) $R_f$=0.78 ($R_f$ of alcohol=0.49).

N. [1S-[1α(R*,E),2α,3α,4α]]-3-[[(1,1-Dimethylethyl)dimethylsilyl]oxy]-7-[2-[2,2-dimethyl-1-oxobutoxy)methyl]-3-[(phenylmethoxy)methyl]-7-oxabicyclo[2.2.1]hept-1-yl]-5-oxo-6-heptenoic acid, methyl ester To a solution of (R)-6-(dimethoxyphosphinyl)-3-[[(1,1-dimethylethyl)dimethylsilyl]oxy]-5-oxohexanoic acid, methyl ester (1.79 g, 4.69 mmole) in dry acetonitrile (20 mL) at room temperature under argon was successively added anhydrous LiCl (0.200 g, 4.76 mmole), DBU (530 μL, 3.54 mmole) and a solution of Part M aldehyde (1.26 g, 3.37 mmole) in dry acetonitrile (5 mL). After 15 minutes, the LiCl went into solution and a cloudy precipitate began to form. After stirring at room temperature for 16 hours, the mixture was partitioned between EtOAc-5% KHSO$_4$, the organic phase washed with 5% KHSO$_4$, saturated NaHCO$_3$, and saturated NaCl solutions, dried over Na$_2$SO$_4$ and evaporated to dryness. The crude product was purified by flash chromatography on silica gel (100 g, LPS-1) eluting with acetone-hexane (1:15) to give title enone (1.665 g, 78%) as a colorless oil.

TLC (EtOAc-hexane; 4:6) $R_f$=0.59 ($R_f$ of Part M aldehyde=0.50).

O. [1S-[1α(R*,E),2α,3α,4α]]-7-[2-[(2,2-Dimethyl-1-oxobutoxy)methyl]-3-[(phenylmethoxy)methyl]-7-oxabicyclo[2.2.1]hept-1-yl]-3-hydroxy-5-oxo-6-heptenoic acid, methyl ester To a solution of Part N enone (0.460 g, 0.73 mmole) in acetonitrile (15 mL) was added 48% aqueous HF (0.10 mL). After stirring at room temperature for 90 minutes, the mixture was partitioned between EtOAc-saturated NaHCO$_3$ (50 mL each). The organic phase was washed with saturated NaCl solution, dried over Na$_2$SO$_4$ and evaporated to dryness to give title keto-alcohol (0.367 g, 97%) as a colorless oil.

TLC (EtOAc-hexane; 4:6) $R_f$=0.09 ($R_f$ of Part N enone=0.49).

P. [1S-[1α(3R*,5S*,6E),2α,3α,4α]]-7-[2-[(2,2-Dimethyl-1-oxobutoxy)methyl]-3-[(phenylmethoxy)methyl]-7-oxabicyclo[2.2.1]-hept-1-yl]-3,5-dihydroxy-6-heptenoic acid, methyl ester A solution of trimethylacetic acid (0.005 g, 0.05 mmole) in 1.0M triethylborane-THF (0.85 mL, 0.85 mmole) was stirred at room temperature under argon for 1 hour. To this solution was added a solution of Part O keto-alcohol (0.367 g, 0.711 mmole) in dry THF (6 mL). After stirring at room temperature under argon for an additional 1 hour, the mixture was cooled to −78° C. (dry ice-EtOH bath) and treated successively with NaBH$_4$ (0.085 g, 2.25 mmole) and methanol (1.4 mL, added dropwise). After stirring at −78° C. for 2.5 hours, the solution was treated dropwise with 30% H$_2$O$_2$ (1.7 mL)-water (6.0 mL) and allowed to warm to room temperature. After stirring at room temperature for 30 minutes, the mixture was partitioned between EtOAc-5% KHSO$_4$ (50 mL each). The organic phase was washed with saturated NaHCO$_3$ and saturated NaCl, dried over Na$_2$SO$_4$ and evaporated to dryness. The crude product was purified by flash chromatography on silica gel (40 g, LPS-1) eluting with acetone-hexane (2:8) to give title diol (0.300 g, 81%) as a colorless oil.

TLC (acetone-hexane; 35:65) $R_f$=0.27. ($R_f$ of Part O keto-alcohol=0.34).

Q. [1S-[1α(3R*,5S*,6E),2α,3α,4α]]-7-[2-[(2,2-Dimethyl-1-oxobutoxy)methyl]-3-[(phenylmethoxy)methyl]-7-oxabicyclo[2.2.1]hept-1-yl]-3,5-dihydroxy-6-heptenoic acid, monolithium salt To a solution of Part P methyl ester (0.300 g, 0.579 mmole) in dioxane (3.0 mL) was added 1.0N LiOH (0.61 mL, 0.61 mmole) and the resulting solution stirred at room temperature under argon for 30 minutes. The solution was then evaporated to dryness and the crude product purified by chromatography on HP-20 (15 mL bed volume, 1 inch diameter column) eluting first with water (30 mL) then with methanol-water (75:25; 500 mL). The product containing fractions were combined and evaporated to dryness. The residue was taken up in water, filtered through a polycarbonate membrane and lyophilized to give title lithium salt (0.260 g, 88%) as a fluffy, white solid.

TLC (AcOH-MeOH-CH$_2$Cl$_2$; 1:1:20) $R_f$=0.30.

[alpha]$_D$=+23.8° (c=0.56, MeOH) mp 195-200° C. (becomes glass).

$^1$H-NMR (270 mz, CD$_3$OD) δ 0.81 ppm (3H, t), 1.10 (6H, s), 1.48 (2H, q), 3.42 (1H, broad t), 3.53 (1H, dd), 4.05 (2H, m), 4.31 (1H, broad q), 4.47 (1H, d), 4.53 (2H, AB q), 5.81 (1H, dd), 5.99 (1H, d).

Anal. Cald'd for C$_{28}$H$_{39}$O$_8$Li+0.47 H$_2$O: C, 64.80; H, 7.76; H$_2$O, 1.63

Found: C, 64.80; H, 7.68; H$_2$O, 1.11 (KF).

EXAMPLE 8

[1R-[1α(βR*,δS*),2α,3α,4α]]-2-[(2,2-Dimethyl-1-oxobutoxy)methyl]-62 ,δ-dihydroxy-3-[(phenylmethoxy)methyl]-7-oxabicyclo[2.2.1]heptane-1-heptanoic acid, monolithium salt A. [1S-[1α(R*),2α,3α,4α]]-2-[(2,2-Dimethyl-1-oxobutoxy)methyl]-β-hydroxy-δ-oxo-3-[(phenylmethoxy)methyl]-7-oxabicyclo[2.2.1]heptane-1-heptanoic acid, methyl ester To a mixture of Example 7, Part N enone (0.986 g, 1.54 mmole) and dimethylphenylsilane (0.710 g, 5.22 mmole) was added tris(triphenylphosphine)rhodium chloride (0.015 g, 0.016 mmole) and the resulting mixture heated at 50° C. (bath temperature) for 2 hours. The excess silane was distilled off at 50° C., 0.5 mmHg.

TLC (EtOAc-hexane; 3:7) shows the silyl enol-ether at $R_f$=0.64 ($R_f$ of Example 7, Part N enone=0.45).

The crude silyl enol-ether was taken up in acetonitrile (20 mL) and treated with 48% aqueous HF (0.17 mL). After stirring at room temperature for 30 minutes, the mixture was partitioned between EtOAc-saturated NaHCO$_3$ (75 mL each). The organic phase was washed with saturated NaCl solution, dried over Na$_2$SO$_4$ and evaporated to dryness. The crude product was purified by flash chromatography on silica gel (80 g, LPS-1) eluting with EtOAc-hexane (4:6) to give title keto-alcohol (0.598 g, 75%) as a colorless oil.

TLC (acetone-hexane; 35:65) $R_f$=0.40.

B. [1R-[1α(βR*,δR*),2α,3α,4α]]-2-[(2,2-Dimethyl-1-oxobutoxy)methyl]-β,δ-dihydroxy-3-[(phenylmethoxy)methyl-7-oxabicyclo[2.2.1]heptane-1-heptanoic acid, methyl ester A solution of trimethylacetic acid (0.007 g, 0.07 mmole) in 1.0M triethylborane-THF (1.40 mL, 1.40 mmole) was stirred at room temperature under argon for 1 hour. To this solution was added a solution of Part A keto-alcohol (0.598 g, 1.15 mmole) in dry THF (10 mL). After stirring at room temperature under argon for an additional 1 hour, the mixture was cooled to −78° C. (dry ice-EtOH bath) and treated successively with NaBH$_4$ (0.138 g, 3.65 mmole) and methanol (2.5 mL, added dropwise). After stirring at −78° C. for 2.5 hours, the solution was treated dropwise with 30% H$_2$O$_2$ (2.8 mL)-water (8.0 mL) and allowed to warm to room temperature. After stirring at room temperature for 30 minutes, the mixture was partitioned between EtOAc-5% KHSO$_4$. The organic phase was washed with saturated NaHCO$_3$ and saturated NaCl, dried over Na$_2$SO$_4$ and evaporated to dryness. The crude product was purified by flash chromatography on silica gel (60 g, LPS-1) eluting with acetone-hexane (2:8) to give title diol (0.581 g, 97%) as a colorless oil.

TLC (acetone-hexane; 35:65) R$_f$=0.30. (R$_f$ of Part A keto-alcohol=0.40).

C. [1R-[1α(βR*,δR*),2α,3α,4α]]-2-[(2,2-Dimethyl-1-oxobutoxy)methyl]-β,δ-dihydroxy-3-[(phenylmethoxy)methyl]-7-oxabicyclo[2.2.1]heptane-1-heptanoic acid, monolithium salt To a solution of Part B methyl ester (0.581 g, 1.12 mmole) in dioxane (5.0 mL) was added 1.0N LiOH (1.2 mL, 1.2 mmole) and the resulting solution stirred at room temperature under argon for 30 minutes. The solution was then evaporated to dryness and the crude product purified by chromatography on HP-20 (25 mL bed volume, 1 inch diameter column) eluting first with water (300 mL) then with methanol-water (75:25). The product containing fractions were combined and evaporated to dryness. The residue was taken up in water, filtered through a polycarbonate membrane and lyophilized to give title lithium salt (0.496 g, 87%) as a fluffy, white solid.

TLC (AcOH-MeOH-CH$_2$Cl$_2$; 1:1:20) R$_f$=0.25.

[alpha]$_D$= +36.4° (c=0.53, MeOH) mp 195–200° C. (becomes glass).

$^1$H-NMR (270 MHz, CD$_3$OD) δ 0.81 ppm (3H, t), 1.09 (6H, s), 1.50 (2H, q), 3.40 (1H, broad t), 3.55 (1H, dd), 3.76 (1H, broad m), 3.90 (1H, dd), 4.10 (1H, broad m), 4.23 (1H, dd), 4.40 (1H, d), 4.50 (2H, AB q).

Anal. Calc'd for C$_{28}$H$_{41}$O$_8$Li+0.62 H$_2$O: C, 64.20; H, 8.15; H 0, 2.15

Found: C, 64.20; H, 7.86; H$_2$O, 0.83 (KF).

EXAMPLE 9

[1R-[1α(βR*,δR*),2α,3α,4α]]-2-[(2,2-Dimethyl-1-oxobutoxy)methyl]-62,δ-dihydroxy-3-(hydroxymethyl)-7-oxabicyclo[2.2.1-]heptane-1-heptanoic acid, monolithium salt To a solution of Example 8 benzyl ether (0.215 g, 0.420 mmole) in methanol (50 mL) was added 10% Pd-C (0.102 g) and the resulting mixture hydrogenated on a Parr apparatus at a pressure of 50 psi for 4 days. The catalyst was removed by filtration through Celite and the filtrate evaporated to dryness. TLC (AcOH-MeOH-CH$_2$Cl$_2$; 1:1:20) indicated the presence of a small amount of unreacted benzyl ether. The residue was again taken up in methanol (30 mL) treated with 10% Pd-C (0.230 g) and hydrogenated as before for an additional 4 days. The catalyst was again removed by filtration through Celite and filtrate evaporated to dryness. The residue was chromatographed on HP-20 (20 mL bed volume, 1 inch diameter column) eluting first with water then with 25% MeOH-water. The product containing fractions were pooled and evaporated to dryness. The glassy residue was taken up in water, filtered (polycarbonate membrane) and lyophilized to give title lithium salt (0.161 g, 91%) as a fluffy white solid.

TLC (AcOH-MeOH-CH$_2$Cl$_2$; 1:1:20) R$_f$=0.10 (R$_f$ of Example 8 benzyl ether=0.39).

[alpha]$_D$= +41.6 (c=0.55, MeOH).

$^1$H NMR (CD$_3$OD, 270 MHz) 0.85 (3H, t), 1.16 (6H, s), 1.45–2.42 (15H, m), 3.45 (1H,t), 3.68 (1H, dd), 3.76 (1H, broad m), 3.90 (1H, dd), 4.10 (1H, broad m), 4.23 (1H, dd), 4.42 (1H, d).

Anal. Calc'd for C$_{21}$H$_{35}$O$_8$Li: C, 57.20; H, 8.47

Found: C, 57.20; H, 8.16.

EXAMPLE 10

[1R-[1α(3R*,5S*,E),2α,4α,6β]]-7-[2-[(2,2-Dimethyl-1-oxobutoxy)methyl]-6-methyl-7-oxabicyclo[2.2.1]-hept-1-yl]-3,5-dihydroxy-6-heptenoic acid, monolithium salt A. 3-Methyl-2-furanoic acid A mixture of 3-methyl-2-furoic acid, methyl ester [20.0 g, 0.14 mole, 0.14 mole, Organic Synthesis 39, 49 (1959)] and 20% NaOH solution (46 mL) was refluxed under argon for 2 hours. The cooled mixture was acidified with concentrated HCl (28.5 mL). The resulting white precipitate was collected, washed with water and dried in vacuo to give the title acid (16.53 g, 94%) as a white crystalline solid, mp 132–134° C.

B. (R)-N-(2-Hydroxy-1-phenylethyl)-3-methyl-2-furamide

To a solution of the Part A acid (16.0 g, 0.127 mole), hydroxybenztriazole hydrate (17.2 g, 0.127 mole) and D-(−)-α-phenylglycinol (17.8 g, 0.127 mole) in methylene chloride (500 mL) at room temperature under argon was added dicyclohexylcarbodiimide (26.2 g, 0.127 mole). After stirring at room temperature for 22 hours, the mixture was filtered and evaporated to dryness. The residue was taken up in EtOAc (1.5L) and washed successively with 5% NaHCO$_3$, 5% KHSO$_4$ and saturated NaCl solutions, dried (MgSO$_4$) and evaporated to dryness. The residue (38 g) was purified by flash chromatography on silica gel (LPS-1) eluting with EtOAc-hexane (1:4 then 1:2) to give the title amide (29.2 g, 94%) as a white crystalline solid, mp 101–102° C.

TLC (EtOAc-hexane; 1:1) R$_f$=0.37.

C. (R)-N-(2-Hydroxy-1-phenylethyl)-3-methyl-2-aminomethylfuran

A solution of the Part B amide (15.4 g, 63 mmol) in dry THF (300 mL) was added dropwise to a suspension of LiAlH$_4$ (5.0 g) in dry THF (300 mL) at 0° C. (ice bath) under argon. The resulting mixture was refluxed for 3.0 hours, cooled in an ice bath and quenched by the sequential addition of H$_2$O (5.0 mL), 10% NaOH (7.5 mL) and H$_2$O (15.0 mL). The mixture was stirred for 30 minutes, mixed with Celite and filtered, washing the filter cake well with CH$_2$Cl$_2$ (500 mL). The combined filtrates were dried (MgSO$_4$) and evaporated to dryness. The crude product (17.85 g) was combined with that of another similar run starting with 15.0 g of the Part B amide and purified by flash chromatography on silica gel (LPS-1) eluting with acetone —CH$_2$Cl$_2$ (1:9 then 1:4) to give the title alcohol (23.44 g, 82%) as a colorless oil.

TLC (acetone-CH$_2$Cl$_2$; 1:4) R$_f$=0.34.

D. [3aS-[2(R*),3aα,4β,6α,7aβ]]-2,3,7,7a-Tetrahydro-2-(hydroxy-1-phenylethyl)-4-methyl-3a,6-epoxy-3aH-isoindol-1(7aH)-one and E. [3aR-[2(R*),3aα,4β,6α,7aβ]]-2,3,7,7a-Tetrahydro-2-(hydroxy-1-phenylethyl)-4-methyl-3a,6-epoxy-3aH-isoindol-1(7aH)-one A solution of the Part C amine (30.41 g, 0.13 mole), triethylamine (73 mL, 0.53 mole) and DMAP (3.3 g) in dry THF (580 mL) at 0° C. (ice bath) was treated dropwise with acryloyl chloride (27.4 mL, 0.33 mole). After stirring at 0° C. for 1 hour and at room temperature for 19 hours, the mixture was diluted with $Et_2O$ (1.0L), and filtered washing the filter cake with $Et_2O$ (1.0L) and EtOAc (1.0L). The combined filtrate was washed with water (200 mL) and saturated NaCl solution, dried ($MgSO_4$) and evaporated to dryness.

TLC (EtOAc) shows two products, $R_f$=0.73 (N-monoacyl) and $R_f$=0.95 (N,O-diacyl) ($R_f$ of Part C amine=0.60).

The crude mixture (38.60 g) was taken up in dioxane (400 mL) and treated with 1.0N LiOH solution (136 mL, 0.136 mole). After stirring at room temperature for 3 hours, the mixture was acidified with 10% HCl (55 mL) and evaporated to dryness. The residue was partitioned between $CH_2Cl_2$-saturated NaCl solution, the organic phase dried over $MgSO_4$ and evaporated to dryness. The residue was taken up in $CH_2Cl_2$ (2.0L), treated with Baker silica gel (115 g) and stirred at room temperature under argon for 48 hours. The mixture was filtered and evaporated to dryness. TLC (EtOAc) shows two products, $R_f$=0.28 (title D product) and $R_f$=0.18 (title E product). The crude mixture (31.44 g) was combined with crude product from a smaller run (10.0 g, total 41.44 g) and purified by flash chromatography on silica gel eluting successively with EtOAc-hexane (3:1 then 7:1), EtOAc(neat) and EtOAc-acetone (1:2) to give the title D product [12.63 g, 34%, $R_f$=0.28 (EtOAc)] and the title E product [19.22 g, 51%, $R_f$=0.18], both as colorless oils.

F. [3aR-[2(R*),3aα,4β,6α,7aβ]]-Hexahydro-2-(hydroxy-1-phenylethyl)-4-methyl-3a,6-epoxy-3aH-isoindol-1(7aH)-one A solution of the Part E olefin (1.50 g, 5.26 mmole) in methanol (60 mL) was treated with 5% Pt-C (75 mg) and hydrogenated at room temperature (1 atm). After 30 minutes, the mixture was filtered through Celite and evaporated to dryness. TLC (EtOAc-acetone; 2:1) shows two products, $R_f$=0.26 (title F product) and $R_f$=0.21 (methyl isomer). The crude product (1.51 g) was purified by flash chromatography eluting with EtOAc-acetone (4:1 then 1:1) to give the pure title compound (1.37 g, 91%) as a colorless oil.

TLC (EtOAc-acetone; 2:1) $R_f$=0.26.

G. [3aR-[2(R*),3aα,4β,6α,7aβ]]-Hexahydro-2-(methoxy-1-phenylethyl)-4-methyl-3a,6-epoxy-3aH-isoindol-1(7aH)-one A solution of the Part F alcohol (5.00 g, 17.4 mmole) in dry THF (440 mL) at 0° C. (ice bath) under argon was treated with 60% NaH oil dispersion (1.04 g, 26 mmol). After stirring at 0° C. for 30 minutes, the mixture was treated with methyl iodide (1.65 mL) and allowed to warm to room temperature. After stirring at room temperature for 3 hours, the reaction was quenched with 5% $KHSO_4$ (150 mL) and extracted with EtOAc (3×500 mL). The combined extracts were washed with saturated NaCl, dried ($MgSO_4$) and evaporated to dryness. The crude product was purified by flash chromatography on silica gel (LPS-1) eluting with EtOAc-acetone (5:1) to give 5.98 g (theory 5.24 g) of the title product as a colorless, viscous oil.

TLC (EtOAc-acetone; 2:1) $R_f$=0.63.

H. [3aR-[2(R*),3aα,4β,6α,7aβ]]-Hexahydro-4-methyl-3a,6-epoxy-3aH-isoindol-1(7aH)-one A solution of the Part G methyl ether (3.90 g, ca. 12.9 mmol) in dry THF (160 mL) was added to a flask containing liquid $NH_3$ (ca. 1.5L) at −78° C. The resulting solution was treated portionwise with sodium metal (2.65 g) over a period of 1.5 hours. After stirring an additional 2 hours at −78° C., the reaction was quenched with solid ammonium chloride (15.3 g). The solution was allowed to warm to room temperature overnight to evaporate off the ammonia, diluted with water (80 mL) and extracted with $CH_2Cl_2$ (3×400 mL). The combined extracts were washed with saturated NaCl solution, dried ($MgSO_4$) and evaporated to dryness. The residue was purified by flash chromatography on silica gel (Baker) eluting with EtOAc-acetone (7:1 then 4:1) to give the title compound (1.87 g, 86%) as a colorless oil. A sample crystallized from $Et_2O$ had mp 115–117° C.

$[\alpha]_D$= +53.6° (c=0.33, MeOH).

TLC (EtOAc-acetone; 2:1) $R_f$=0.23.

Anal. Calc'd for $C_9H_{13}NO_2$: C, 64.65; H, 7.84; N, 8.38 Found: C, 64,78; H, 7.98; N, 8.36.

I. [3aR-(3aα,4β,6α,7aβ)]-Hexahydro-4-methyl-3H-3a,6-epoxyisobenzofuran-1(7aH)-one A solution of Part H compound (2.6 g, 15.6 mmole) in a mixture of acetic anhydride (78.4 mL) and glacial acetic acid (15.6 mL) was cooled down to 0° C. (ice bath) under argon and treated over a period of 5 hours with sodium nitrite (23.2 g, 0.34 mole). The mixture was stirred at 0° C. (ice water) for another 20 hours and the resulting yellow green solution was poured onto ice water (125 mL) and extracted with dichloromethane (3×250 mL). The combined organic extracts were washed with saturated $NaHCO_3$ (125 mL), brine (130 mL), dried (anhydrous $MgSO_4$), filtered and evaporated to dryness. The crude product (2.8 g, yellow-green semi-solid) was chromatographed on a silica gel column (Baker, 60-200 mesh, 150 mL), eluting the column with EtOAc:Hexane mixtures (1:4; 1:1). The desired fractions were combined and evaporated to give the N-nitroso compound as a solid (2.19 g, 71.5%), m.p. 100–102° C.

TLC: $R_f$ 0.63 (Silica gel; EtOAc:Hexane-1:1).

A solution of the N-nitroso compound (2.19 g, 11.2 mmole) in absolute ethanol (28 mL) was cooled down to 0° C. (ice water) under argon and treated dropwise with a solution of 2N KOH in EtOH (16.5 mL). The mixture was stirred at 0° C. (ice water) for 20 minutes, acidified with 10% HCl (17.9 mL) and stirred for another 20 minutes at 0° C. The mixture was evaporated to dryness, chasing off the residual HCl by evaporating the semi-solid several times from acetonitrile. The product was triturated with ethyl acetate (3×250 mL) and the combined extracts were evaporated to dryness. The product mixture (~4.0 g) was dissolved in dry benzene (75 mL), treated with $TsOH \cdot H_2O$ (150 mg) and stirred overnight at room temperature under $N_2$. The solution was evaporated to dryness and the crude product chromatographed on a silica gel column (LPS-1), eluting the column with EtOAc:Hexane mixture (1:7; 1:4). The desired fractions were combined and evaporated to give title compound as a waxy solid (1.49 g, 56.8% overall yield).

TLC $R_f$ 0.56 (Silica gel; EtOAc:Hexane-1:1).

J. [1S-(1α,3aβ,4α,6β,7aα)]-Hexahydro-4-methyl-3H-3a,6-epoxyisobenzofuran-1-ol

A solution of Part I compound (1.41 g, 8.4 mmole) in dry toluene (40 mL) was cooled down to −78° C. (dry ice-acetone) under argon, treated dropwise with 1.5M DiBAL in toluene (7.26 mL, 1.55 g, 1.3 eq.) and stirred at −78° for 3 hours. The mixture was quenched by adding silica gel (10.4 g) and water (1.4 mL), allowed to warm up to room temperature and stirred for 30 minutes. The slurry was filtered, washing the silica gel well with ethyl acetate (3×150 mL), and EtOAc:MeOH (9:1, 300 mL). The combined filtrates were evaporated to dryness and the crude product mixture (1.43 g) was chromatographed on a silica gel column (Baker, 60-200 mesh, 150 mL), eluting the column with EtOAc:Hexane (1:4). The desired fractions were combined and evaporated to give title compound as a colorless oil (1.32 g, 92.6%).

TLC: $R_f$ 0.28 (Silica gel; EtOAc: MeOH-1:1).

K. [1R-(1α,2α,4α,6β)]-2-Ethenyl-6-methyl-7-oxabicyclo[2.2.1]heptane-1-methanol

A suspension of methyltriphenylphosphonium bromide (12.24 g, 34.3 mmole) in dry tetrahydrofuran (83 mL) was cooled down to −78° C. (dry ice-acetone) under argon, treated with 1.6M n-butyllithium (18.8 mL, 30.2 mmole, 3.9 eq.) in hexane and stirred at −78° C. for 30 minutes and at 0° (ice water) for 1.0 hour. The reaction mixture was then treated with a solution of Part J compound (1.32 g, 7.76 mmole) in dry tetrahydrofuran (34 mL), stirred at 0° for 30 minutes, allowed to warm up to room temperature and stirred for another 20 hours. The mixture was quenched with 25% NH₄Cl (13.9 mL) and the thick aqueous slurry was extracted with ethyl acetate (3×150 mL). The combined organic extracts were dried (anhydrous MgSO₄), filtered and evaporated to dryness. The crude product was chromatographed on a silica gel column (Baker, 60-200 mesh, 400 mL), eluting the column with EtOAc:Hexane (1:3) to give title compound as a colorless oil (1.25 g, 95.7%).

TLC: $R_f$ 0.52 (Silica gel; EtOAc:Hexane-1:1).

L. [1R-(1α,2α,4α,6β)]-1-[[[(1-Dimethylethyl)dimethylsilyl]oxy]methyl]-2-ethenyl-6-methyl-7-oxabicyclo[2.2.1]heptane A solution of Part K compound (1.2 g, 7.13 mmole) in dry methylene chloride (17 mL) was treated with t-butyl dimethylsilylchloride (1.28 g, 1.2 eq., 8.6 mmole), 4-dimethylaminopyridine (171.5 mg) and triethylamine (1.2 mL, 8.7 mmole) and stirred at room temperature under argon for 19 hours. The mixture was diluted with dichloromethane (34 mL) and partitioned between 5% KHSO₄ (50 mL) and dichloromethane (2×175 mL). The combined organic extracts were dried (anhydrous MgSO₄), filtered and evaporated to dryness. The crude product was chromatographed on a silica gel column (Baker, 60-200 mesh, 150 mL), eluting the column with EtOAc:Hexane (1:9) to give title compound as a colorless oil (1.98 g, 98.5%).

TLC: $R_f$ 0.68 (Silica gel; EtOAc:Hexane-1:9).

M. [1R-(1α,2α,4α,662 )]-1-[[[(1,1-Dimethylethyl)dimethylsilyl]oxy]methyl]-6-methyl-7-oxabicyclo[2.2.1]heptane-2-methanol A solution of Part L compound (1.0 g, 3.54 mmole) in dry methanol (44 mL) was cooled down to −78° (dry ice-acetone) and ozone was bubbled through the solution until a blue color persisted. The solution was then purged with nitrogen until the color disappeared, treated with dimethylsulfide (1.01 mL), stirred at −78° for 30 minutes and at 0° for 2.0 hours. The mixture was evaporated to dryness. The residual syrup was dissolved in dry tetrahydrofuran (44 mL), cooled down to 0° (ice water) and treated with lithium tri-tert-butoxyaluminum hydride (2.23 g, 8.78 mmole). The reaction mixture was allowed to warm up to room temperature, stirred for 1.5 hours under nitrogen then quenched with saturated sodium sulfate (10.1 mL) and stirred for 30 minutes. The suspension was filtered, washing the solids well with dichloromethane (175 mL). The combined organic extracts were dried (anhydrous MgSO₄), filtered and evaporated to dryness. The de product (1.16 g) was chromatographed on a silica gel column (Baker, 60-200 mesh, 150 mL), eluting the column with EtOAc:Hexane (1:4). The desired fractions were combined and evaporated to give title compound as a colorless oil (893.9 mg, 88.5%).

TLC: $R_f$ 0.19 (Silica gel; EtOAc:Hexane-1:4).

N. [1R-(1α,2α,4α,6β)]-1-[[[(1,1-Dimethylethyl)dimethylsilyl]oxy]methyl]-6-methyl-7-oxabicyclo[2.2.1]heptane-2-methanol, 2,2-dimethylbutanoate A solution of Part M compound (893.9 mg, 3.12 mmole) in dry pyridine (7.0 mL) was cooled down to 0° (ice water) under argon and treated with 4-dimethylaminopyridine (45 mg) and 2,2-dimethylbutyryl chloride (646 mg, 4.8 mmole). The mixture was stirred at 0° for 15 minutes, at room temperature for 18 hours and evaporated to dryness. The residual syrup was partitioned between 5% KHSO₄ (20 mL) and ethyl acetate (3×100 mL) and the combined organic extracts were washed with brine (25 mL), dried anhydrous MgSO₄), filtered and evaporated to dryness. The crude product (1.13 g) was chromatographed on a silica gel column (LPS-1), eluting the column with Et₂O:Hexane (1:9) to give title compound as a colorless oil (878.3 mg, 73.8%).

TLC: $R_f$ 0.37 (Silica gel; EtOAc:Hexane-1:4).

O. [1R-(1α,2α,4α,6β)]-6-Methyl-7-oxabicyclo[2.2.1]heptane-1,2-dimethanol, 2-(2,2-dimethylbutanoate)

A solution of Part N compound (775.9 mg, 2.03 mmole) in dry acetonitrile (46 mL) was treated with 48% hydrofluoric acid (0.78 mL) and stirred at room temperature for 1.5 hours under argon. The reaction mixture was partitioned between a solution of NaHCO₃ (1.81 g) in water (14.3 mL) and ethyl acetate (3×115 mL). The combined organic extracts were washed with brine (30 mL), dried (anhydrous MgSO₄), filtered and evaporated to dryness. The crude product (600 mg) was chromatographed on a silica gel column (Baker, 60-200 mesh, 100 mL), eluting the column with EtOAc:Hexane (1:4). The desired fractions were combined and evaporated to give title compound as a colorless oil (564.1 mg, 100%).

TLC: $R_f$ 0.17 (Silica gel; EtOAc:Hexane-1:4).

P. [1R-(1α,2α,4α,6β)]-2-[(2,2-Dimethyl-1-oxobutoxy)methyl]-6-methyl-7-oxabicyclo[2.2.1]heptane-1-carboxaldehyde A solution of Dess-Martin periodinane (749 mg; 1.67 mmole; 1.5 eq.) and t-butyl alcohol (0.17 mL, 1.5 eq.) in dry dichloromethane (5.5 mL) was stirred at room temperature for 15 minutes, treated with a solution of Part O compound (300 mg; 1.11 mmole) in dry dichloromethane (5.5 mL) and stirred for 20 hours under nitrogen at room temperature. The reaction mixture was then diluted with dichloromethane (70 mL) and poured into a solution of Na₂S₂O₃ (2.95 g, 7-fold excess) in 1N NaHCO₃ (16.3 mL), stirring the mixture until the precipitates went into solution. The aqueous phase was re-extracted with dichloromethane (2×70 mL) and the combined organic extracts were washed with brine (20 mL), dried (anhydrous MgSO4), filtered and evaporated to dryness. The crude product (360 mg) was chromatographed on a silica gel column (LPS-1), eluting the column with EtOAc:Hexane mixtures (1:9; 1:4). The desired fractions were combined and evaporated to dryness to give title compound as a colorless oil (272.7 mg, 91.5%).

TLC: $R_f$ 0.45 (Silica gel; EtOAc:Hexane-1:4).

Q. [1R-[1α(R*,E),2α,4α,6β]]-3-[[(1,1-Dimethylethyl)-dimethylsilyl]oxy]-7-[2-[(2,2-dimethyl-1-oxobutoxy)-methyl]-6-methyl-7-oxabicyclo[2.2.1]hept-1-yl]-5-oxo-6-heptenoic acid, methyl ester (R)-6(Dimethoxyphosphinyl)-3-[[(1,1-dimethylethyl)dimethylsilyl]oxy]-5-oxo-hexanoic acid, methyl ester (523 mg, 1.41 mmole) was dissolved in dry acetonitrile (7.1 mL) and treated successively with dry LiCl (57 mg), 1,8-diazabicyclo [5.4.0]undec-7-ene (96%, 170 μL) and a solution of Part P compound (272.7 mg, 1.02 mmole) in dry acetonitrile (7.1 mL). The mixture became cloudy within 10 minutes and was stirred at room temperature under argon for 20 hours, quenched with 5% KHSO4 (15 mL) and extracted with ethyl acetate (3×100 mL). The combined organic extracts were washed with saturated NaHCO3 (12 mL), brine (20 mL), dried (anhydrous MgSO4), filtered and evaporated to dryness. The crude product (757.1 mg) was chromatographed on a silica gel column (LPS-1), eluting the column with EtOAc:Hexane mixture (1:9; 1:4). The desired fractions were combined and evaporated to dryness to give title compound as a colorless oil (537.3 mg, 100%).

TLC: $R_f$ 0.40 (Silica gel; EtOAc:Hexane-1:4).

R. [1R-[1α(R*,E),2α,4α,6β]]-7-[2-[(2,2-Dimethyl-1-oxobutoxy)methyl]-6-methyl-7-oxabicyclo-[2.2.1]hept-1-yl]-3-hydroxy-5-oxo-6-heptenoic acid, methyl ester A solution of Example Q compound (527.3 mg, 1.02 mmole) in dry tetrahydrofuran (27 mL) was treated with glacial acetic acid (0.47 mL, 7.7 eq.), followed by 1M (C4H9)4NF/THF (6.1 mL, 5.7 eq.) and stirred at room temperature under argon for 4.0 days. The reaction mixture was diluted with ice water (15 mL) and extracted with ether (3×100 mL). The combined organic extracts were washed with saturated NaHCO3 (15 mL), brine (15 mL), dried (anhydrous MgSO4), filtered and evaporated to dryness. The crude product (697.6 mg) was chromatographed on a silica gel column (LPS-1), eluting the column with EtOAc:Hexane mixtures (1:4; 1:1) to give title compound as a colorless oil (345.5 mg, 90.6%).

TLC: $R_f$ 0.37 (Silica gel; EtOAc:Hexane-1:1).

S. [1R-[1α(3R*,5S*,E),2α,4α,6β]]-7-[2-[(2,2-Dimethyl-1-oxobutoxy)methyl]-6-methyl-7-oxa-bicyclo[2.2.1-]hept-1-yl]-3,5-dihydroxy-6-heptenoic acid, methyl ester A mixture of pivalic acid (6.0 mg, 0.06 mmole) and 1M (C2H5)3B-THF (1.0 mL, 1.0 mmole) was stirred at room temperature under argon for 1.0 hour, treated with a solution of Part R compound (345.5 mg, 0.84 mmole) in dry tetrahydrofuran (7.0 mL) and stirred at room temperature for another hour. The solution was cooled down to −78° (dry ice-acetone), treated with sodium borohydride (100.6 mg, 2.66 mmole) followed by the dropwise addition of methanol (1.66 mL) and the reaction mixture stirred at −78° for 2.5 hours. The mixture was quenched by treatment with −78° with 30% H2O2 (2.0 mL)-H2O (7.1 mL), warmed up to room temperature and stirred for 30 minutes. The mixture was partitioned between 5% KHSO4 (10 mL) and ethyl acetate (3×75 mL) and the combined organic extracts were washed with saturated NaHCO3 (10 mL), brine (20 mL), dried (anhydrous MgSO4), filtered and evaporated to dryness. The crude product (382 mg) was chromatographed on silica gel column (LPS-1), eluting the column with EtOAc: Hexane mixtures (1:4; 1:1). The desired fractions were combined and evaporated to dryness to give title ester as a colorless oil (282.6 mg, 81.8%).

TLC: $R_f$ 0.15 (Silica gel; EtOAc:Hexane-1:1).

T. [1R-[1α(3R*,5S*,E),2α,4α,6β]]-7-[2-[(2,2-Dimethyl-1-oxobutoxy)methyl]-6-methyl-7-oxabicyclo[2.2.1-]hept-1-yl]-3,5-dihydroxy-6-heptenoic acid, monolithium salt A solution of Part S ester (282.6 mg, 0.69 mmole) in dioxane (5.3 mL) was treated with 1N LiOH (0.80 mL, 1.15 mmole) and stirred at room temperature under argon for 2.0 hours. The reaction mixture was evaporated to dryness and the residue dissolved in steam-distilled water (3.0 mL) and chromatographed on an HP-20 column (1″×3″), eluting the column with steam-distilled water (200 mL), 20% aqueous CH3CN (200 mL) and 50% aqueous CH3CN (200 mL). The desired fractions were combined, evaporated to dryness. The residue was dissolved in water (10 mL) and lyophilized to give title salt as a fluffy solid (246 5 mg, 88.3%). IR (1581 cm$^{-1}$, strong, C=O of —COO$^-$: 1726 cm$^{-1}$, strong, C=O of —COOR; 2966 cm$^{-1}$, strong, —OH).

TLC: $R_f$ 0.26 (Silica gel; CH2Cl2: HOAc:CH3OH-20:1:1).

Anal. Calc'd for C21H33O7Li.0.43 H2O: C, 61.18; H, 8.28

Found: C, 60.82; H, 8.23.

H$^1$-NMR Spectrum (270 MHz, CD3OD): δ 0.84 (t, 3H, J=~7), 1.10 (d, 3H, J=~7), 1.14 (s, 6H), 1.49–2.52 (m, 14H), 3.70 (dd, 1H, J=8, 11 Hz), 4.00 (dd, 1H, J=6, 11 Hz), 4.07 (m, 1H), 4.31 (m, 1H), 4.41 (t, 1H, J=~5), 5.79–5.99 (m, 2H).

EXAMPLE 11

[1R-]1α(βR*,δR*),2α,4α,6β]]-2-[(2,2-Dimethyl-1-oxobutoxy)methyl]-β, δ-dihydroxy-6-methyl-7-oxabicyclo[2.2.1]heptane-1-heptanoic acid, monolithium salt A. [1R-[1α(R*),2α,4α,6β]]-β-[[(1,1-Dimethylethyl)-dimethylsilyl]oxy]-2-[(2,2-dimethyl-1-oxobutoxy)methyl]-6-methyl-δ-oxo-7-oxabicyclo[2.2.1]heptane-1-heptanoic acid, methyl ester A solution of Example 10, Part Q compound (800.7 mg, 1.52 mmole) in dry methanol (68 mL) was treated with 10% Pd/C (68 mg) and hydrogenated at room temperature. The reaction mixture, upon completion, was filtered through a millipore unit, washing the spent catalyst well with methanol. The clear filtrate was evaporated to dryness to give title compound as a colorless oil (769.1 mg, 96.1%).

TLC: $R_f$ 0.20 (Silica gel; EtOAc:Hexane-1:4).

B. [1R-[1α(R*),2α,4α,6β]]-2-[(2,2-Dimethyl-1-oxobutoxy)methyl]-β-hydroxy-6-methyl-δ-oxo-7-oxabicyclo[2.2.1]heptane-1-heptanoic acid, methyl ester A solution of Part A compound (769.1 mg, 1.46 mmole) in dry tetrahydrofuran (39 mL) was treated with glacial acetic acid (0.67 mL, 8 eq.) followed by 1M (C4H9)4NF/THF (8.7 mL, 6.0 eq.) and stirred at room temperature under argon for 3.0 days. The reaction mixture was diluted with ice water (25 mL) and extracted with ether (3×150 mL). The combined organic extracts were washed with saturated NaHCO3 (20 mL), brine (25 mL), dried (anhydrous MgSO4), filtered and evaporated to dryness. The crude product (664.8 mg) was chromatographed on a silica gel column (LPS-1), eluting the column with EtOAc: Hexane mixtures (1:4; 1:1) to give title compound as a colorless oil (479.9 mg, 96.9% yield based on recovered starting material).

TLC: R$_f$ 0.28 (Silica gel; EtOAc:Hexane-1:1).

C. [1R-[1α(βR*,δR*),2α,4α,6β]]-2-[(2,2-Dimethyl-1-oxobutoxy)methyl]-β,δ-dihydroxy-6-methyl-7-oxabicyclo[2.2.1]heptane-1-heptanoic acid, methyl ester A solution of Part B compound (479.9 mg, 1.16 mmole) in dry tetrahydrofuran (17 mL) was treated with 1M (C$_2$H$_5$)$_3$B (1.7 mL, 1.74 mmole, 1.5 eq.), stirred at room temperature under argon for 30 minutes, then cooled down to −78° C. (dry ice-acetone). The cooled solution was treated with sodium borohydride (102.5 mg, 2.7 mmole, 2.33 eq.), followed by the dropwise addition of methanol (4.27 mL) and the reaction mixture was stirred at −78° C. for 2.0 hours. The mixture was quenched by treatment at −78° C. with 30% H$_2$O$_2$ (2.56 mL)-H$_2$O (8.54 mL), stirred for 15 minutes, warmed up to room temperature and stirred for another 30 minutes. The mixture was then diluted with water (12 mL) and extracted with ethyl acetate (3×125 mL). The combined organic extracts were washed with saturated NaHCO3 (18 mL), brine (25 mL), dried (anhydrous MgSO4), filtered and evaporated to dryness. The crude product (536.1 mg) was chromatographed on a silica gel column (LPS-1), eluting the column with EtOAc:Hexane (1:2). The desired fractions were combined to give title compound as a colorless oil (420.3 mg, 87.3%).

TLC: R$_f$ 0.15 (Silica gel; EtOAc:Hexane-1:1).

D. [1R-[1α(βR*,δR*),2α,4α,6β]]-2-[(2,2-Dimethyl-1-oxobutoxy)methyl]-α,δ-dihydroxy-6-methyl-7-oxabicyclo[2.2.1]heptane-1-heptanoic acid, monolithium salt A solution of Part C ester (420.3 mg, 1.01 mmole) in dioxane (7.8 mL) was treated with 1N LiOH (1.27 mL, 1.27 mmole, 1.26 eq.) and stirred at room temperature for 3.0 hours. The reaction mixture was evaporated to dryness and the residue dissolved in steam-distilled water (5.0 mL) and chromatographed on an HP-20 column (1"×3"), eluting the column with steam-distilled water (200 mL), 5% aqueous CH$_3$CN (200 mL) and 20% aqueous CH$_3$CN (200 mL). The desired fractions were combined, evaporated to dryness. The product was dissolved in water (10 mL) and lyophilized to give title salt as a fluffy solid (367.5 mg, 89.5%). IR (1581 cm$^{-1}$, strong, C=O of —COO$^-$; 1727 cm$^{-1}$, strong, C=O of —COOR; 2967 cm$^{-1}$ strong, —OH).

TLC: R$_f$ 0.30 (Silica gel; CH$_2$Cl$_2$:HOAc:CH$_3$OH-20:1:1).

Anal. Calc'd for C$_{21}$H$_{35}$O$_7$Li.0.58 H$_2$O: C, 60.51; H, 8.74

Found: C, 60.51; H, 8.87.

H$^1$-NMR Spectrum (270 MHz, CD$_3$OD): δ 0.85 (t, 3H, J= ~7), 1.03 (d, 3H, J= ~6), 1.15 (s, 6H), 1.38–2.44 (m, 17H), 3.77–3.85 (m, 2H), 4.05–3.41 (m, 2H), 4.33 (t, 1H, J= ~5).

EXAMPLE 12

[1R-[1α(βR*,δR*),2α,3α,4α]]-2-[(2,2,-Dimethyl-1-oxobutoxy)methyl]-β,δ-dihydroxy-3-(methoxymethyl)-7-oxabicyclo[2.2.1]heptane-1-heptanoic acid, monolithium salt A. [1R-(1α,2α,3α,4α)]-1-[[[(1,1-Dimethylethyl)dimethylsilyl]oxy]methyl]-2-ethenyl-3-(methoxymethyl)-7-oxabicyclo[2.2.1]heptane To a solution of Example 7 Part I alcohol (0.952 g, 3.19 mmole) in dry THF (8.0 mL) at 0° C. under argon was added 60% NaH-oil dispersion (0.190 g, 4.75 mmole). After stirring at 0° C. for 0.5 hour, iodomethane (300 μL, 4.82 mmole) was added, the mixture warmed to room temperature and stirred for 2 hours. The mixture was then partitioned between EtOAc-5% KHSO4, the organic phase washed with saturated NaHCO3 and saturated NaCl solutions, dried over Na$_2$SO$_4$ and evaporated to dryness. The crude product was purified by flash chromatography on i silica gel (70 g, LPS-1) eluting with Et$_2$O-hexane (5:95) to give title benzyl ether (0.917 g, 92%) as a colorless oil.

TLC: (EtOAc-hexane; 1:1) R$_f$=0.76.

B. [1R-(1α,2α,3α,4α)]-1-[[[(1,1-Dimethylethyl)dimethylsilyl]oxy]methyl]-3-(methoxymethyl)-7-oxabicyclo[2.2.1]heptane-2-methanol A solution of Part A olefin (0.917 g, 2.94 mmole) in methanol (20 mL) at −78° C. (dry ice-EtOH bath) was treated with ozone until the blue color of excess ozone was observed. Nitrogen was passed through the solution until the blue color was discharged and dimethylsulfide (1.10 mL) was added. After stirring at −78° C. for 1 hour and at 0° C. for 2 hours, the mixture was evaporated to dryness to give the crude aldehyde as a colorless oil.

TLC: (EtOAc-hexane; 1:1) R$_f$=0.73 (R$_f$ of Part A olefin=0.76).

The crude aldehyde was taken up in dry THF (20 mL), cooled in an ice bath and treated with LiAl(OC$_4$H$_9$—t)$_3$H (1.87 g, 7.34 mmole) and then allowed to warm to room temperature. After stirring at room temperature for 1 hour, the mixture was placed in an ice bath and quenched with saturated Na$_2$SO$_4$ solution (6 mL). The mixture was dried over Na$_2$SO$_4$, filtered through Celite and evaporated to dryness. The crude product was purified by flash chromatography on silica gel (60 g, LPS-1), eluting with EtOAc:Hexane (2:8) to give title alcohol (0.800 g, 86%) as a colorless oil.

TLC: (EtOAc-Hexane; 1:1) R$_f$=0.40.

C. [1R-(1α,2α,3α,4α)]-1-[[[(1,1-Dimethylethyl)dimethylsilyl]oxy]methyl]-3-(methoxymethyl)-7-oxabicyclo[2.2.1]heptane-2-methanol,2,2-dimethylbutanoate To a solution of Part B alcohol (0.400 g, 1.26 mmole) in dry pyridine (4.0 mL) at 0° C. (ice bath) under argon was added 2,2-dimethylbutyryl chloride (0.265 g, 1.97 mmole) and DMAP (0.025 g, 0.20 mmole). After stirring at 0° C. for 15 minutes and at room temperature for 18 hours, the mixture was evaporated to dryness (30° C., 0.5 mmHg). The residue was taken up in EtOAc and washed successively with 5% KHSO4, saturated NaHCO3 and saturated NaCl, dried over Na$_2$SO$_4$ and evaporated to dryness. The crude product was purified by flash chromatography on silica gel (50 g, LPS-1), eluting with Et$_2$O-Hexane (15:85) to give title ester (0.482 g, 92%) as a colorless oil.

TLC: (EtOAc-hexane; 3:7) R$_f$=0.55 (R$_f$ of Part B alcohol=0.15).

D. [1R-(1α,2α,3α,4α)]-3-(Methoxymethyl)-7-oxabicyclo[2.2.1]heptane-1,2-dimethanol, 2-(2,2-dimethyl-1-oxobutanoate)

A solution of Part C compound (483.7 mg, 1.24 mmole) in dry acetonitrile (29 mL) was treated with 48% hydrofluoric acid (0.47 mL) and stirred at room temperature under argon for 1.0 hour. The reaction mixture was partitioned between a solution of NaHCO$_3$ (1.10 g) in water (9.2 mL) and ethyl acetate (2×75 mL). The combined organic extracts were washed with brine (17 mL), dried (anhydrous MgSO$_4$), filtered and evaporated to dryness. The crude product was chromatographed on a silica gel column (LPS-1), eluting the column with EtOAc:Hexane mixtures (1:4, 1:1). The desired fractions were combined and evaporated to give title compound as a colorless oil (349.1 mg, 93.7%).

TLC: R$_f$ 0.35 (Silica gel; EtOAc:Hexane-1:1).

E. [1R-(1α,2α,3α,4α)]-2-[(2,2-Dimethyl-1-oxobutoxy)methyl]-3-(methoxymethyl)-7-oxabicyclo[2.2.1]heptane-1-carboxaldehyde A solution of Dess-Martin periodinane (783.6 mg, 1.75 mmole, 1.15 eq.) and t-butyl alcohol (0.18 mL, 1.5 eq.) in dry dichloromethane (5.7 mL) was stirred at room temperature for 15 minutes, treated with a solution of Part D compound (349.1 mg, 1.16 mmole) in dry dichloromethane (5.7 mL) and stirred for 22 hours at room temperature under nitrogen. The reaction mixture was then diluted with dichloromethane (75 mL) and poured into a solution of Na$_2$S$_2$O$_3$ (3.1 g, 7-fold excess) in 1N NaHCO$_3$ (17 mL), stirring the mixture until the precipitates went into solution. The aqueous phase was separated and re-extracted with dichloromethane (2×75 mL) and the combined organic extracts were washed with brine (25 mL), dried (anhydrous MgSO$_4$), filtered and evaporated to dryness. The crude product (335 mg) was chromatographed on a silica gel column (LPS-1), eluting the column with EtOAc:Hexane (1:5). The desired fractions were combined and evaporated to dryness to give title compound as a colorless oil (301.8 mg, 87.2%).

TLC: R$_f$ 0.63 (Silica gel; EtOAc:Hexane-1:1).

F. [1S-[1α,(R*,E),2α,3α,4α]]-3-[[(1,1-Dimethylethyl)dimethylsilyl]oxy-7-[2-[(2,2-dimethyl-1-oxobutoxy)methyl]-3-(methoxymethyl)-7-oxabicyclo[2.2.1]hept-1-yl]-5-oxo-6-heptenoic acid, methyl ester (R)-6-(Dimethoxyphosphinyl)-3-[[(1,1-dimethylethyl)dimethylsilyl]oxy]-5-oxo-hexanoic acid, methyl ester (519 mg, 1.4 mmole) was dissolved in dry acetonitrile (7.0 mL) and treated successively with dry LiCl (56 mg), 1,8-diazabicyclo[5.4.0]undec-7-ene (96%, 168 μL) and a solution of Part E compound (301.8 mg, 1.01 mmole) in dry acetonitrile (7.0 mL). The mixture became cloudy within 5 minutes and was stirred at room temperature under argon for 20 hours, quenched with 5% KHSO$_4$ (15 mL) and extracted with ethyl acetate (3×100 mL). The combined organic extracts were washed with saturated NaHCO$_3$ (12 mL), brine (20 mL), dried (anhydrous MgSO$_4$), filtered and evaporated to dryness. The crude product (768 mg) was chromatographed on a silica gel column (LPS-1), eluting the column with EtOAc:Hexane (1:4). The desired fractions were combined and evaporated to dryness to give title compound as a colorless oil (539.2 mg, 96.2%).

TLC: R$_f$ 0.83 (Silica gel; EtOAc:Hexane-1:1).

G. [1S-[1α(R*),2α,3α,4α]]-β-[[(1,1-Dimethylethyl)dimethylsilyl]oxy]-2-[(2,2-dimethyl-1-oxobutoxy)methyl]-3-(methoxymethyl)-δ-oxo-7-oxabicyclo[2.2.1]heptane-1-heptanoic acid, methyl ester A solution of Part F compound (539.2 mg, 0.97 mmole) in dry methanol (45 mL) was treated with 10% Pd/C (43 mg) and hydrogenated at room temperature. The reaction mixture, upon completion, was filtered through a millipore unit, washing the spent catalyst well with methanol. The clear filtrate was evaporated to dryness to give title compound as a colorless oil (540.1 mg, 98.2%).

TLC: R$_f$ 0.75 (Silica gel; EtOAc:Hexane-1:1).

H. [1S-[1α(R*),2α,3α,4α]]-2-[(2,2-Dimethyl-1-oxobutoxy)methyl]-β-hydroxy-3-(methoxymethyl)-δ-oxo-7-oxabicyclo[2.2.1]heptane-1-heptanoic acid, methyl ester A solution of Part G compound (530 mg, 0.95 mmole) in dry tetrahydrofuran (25 mL) was treated with glacial acetic acid (0.44 mL, 7.28 mmole, 7.7 eq.), followed by 1M (C$_4$H$_9$)$_4$NF/THF (5.7 mL, 5.46 mmole, 5.7 eq.) and stirred at room temperature for 3.5 days. The reaction mixture was diluted with ice-water (15 mL) and extracted with ether (3×100 mL). The combined organic extracts were washed with saturated NaHCO$_3$ (15 mL), brine (15 mL), dried (anhydrous MgSO$_4$), filtered and evaporated to dryness. The crude product (501.8 mg) was chromatographed on a silica gel column (LPS-1), eluting the column with EtOAc:Hexane mixtures (1:4; 1:1) to give title compound as a colorless oil (399.6 mg, 95.1%).

TLC: R$_f$ 0.28 (Silica gel; EtOAc:Hexane-1:1).

I. [1R-[1α(βR*,δR*),2α,3α,4α]]-2-[(2,2-Dimethyl-1-oxobutoxy)methyl]-β,δ-dihydroxy-3-(methoxymethyl)-7-oxabicyclo[2.2.1]heptane-1-heptanoic acid, methyl ester A solution of Part H compound (399.6 mg; 0.93 mmole) in dry tetrahydrofuran (13.2 mL) was treated with 1M (C$_2$H$_5$)$_3$B (1.32 mL, 1.35 mmole, 1.45 eq.), stirred at room temperature under argon for 30 minutes, then cooled down to −78° C. (dry ice-acetone). The cooled solution was treated with sodium borohydride (80 mg, 2.1 mmole, 2.27 eq.), followed by the dropwise addition of methanol (3.32 mL) and the reaction mixture was stirred at −78° C. for 2 hours. The mixture was quenched by treatment at −78° C. with 30% H$_2$O$_2$ (1.99 mL)-H$_2$O (6.64 mL), stirred for 15 minutes, warmed to room temperature and stirred for another 30 minutes. The mixture was then diluted with water (10 mL) and extracted with ethyl acetate (3×100 mL) and the combined organic extracts were washed with saturated NaHCO$_3$ (14 mL), brine (20 mL), dried (anhydrous MgSO$_4$), filtered and evaporated to dryness. The crude product (464 mg) was chromatographed on a silica gel column (LPS-1), eluting the column with EtOAc:Hexane mixtures (1:2; 1:1) to give title ester as a colorless oil (328 mg, 79.3%).

TLC: R$_f$ 0.10 (Silica gel; EtOAc:Hexane-1:1).

J. [1R-[1α(βR*,δR*),2α,3α,4α]]-2-[(2,2-Dimethyl-1-oxobutoxy)methyl]-β,δ-dihydroxy-3-(methoxymethyl)-7-oxabicyclo[2.2.1]heptane-1-heptanoic acid, monolithium salt A solution of Part I compound (328 mg, 0.73 mmole) in dioxane (5.7 mL) was treated with 1N LiOH (0.93 mL, 1.27 mmole) and stirred at room temperature under argon for 4.0 hours. The reaction mixture was evaporated to dryness and the residue dissolved in steam-distilled water (5.0 mL) and chromatographed on an HP-20 column (1"×3"), eluting the column with steam-distilled water, 5% aqueous CH$_3$CN, 20% aqueous CH$_3$CN and 50% aqueous CH$_3$CN. The desired fractions were combined, evaporated to dryness. The residue was dissolved in steam-distilled water (10 mL) and lyophilized to give title salt as a fluffy solid (172.4 mg, 54.1%). IR (1579 cm$^{-1}$, strong, C=O of —COO$^-$; 1726 cm$^{-1}$, strong, C=O of —COOR; 2968 cm$^{-1}$, strong, —OH).

TLC: $R_f$ 0.25 (Silica gel; $CH_2Cl_2$:HOAc:$CH_3$OH-20:1:1).

Anal Calc'd for $C_{22}H_{37}O_8Li$·2.22 $H_2O$: C, 55.46; H, 8.76

Found C, 55.46; H, 8.49.

H$^1$-NMR Spectrum (270 MHz, CD$_3$OD): δ 0.87 (t, 3H), 1.17 (s, 6H), 1.52-1.83 (m, 11H), 1.95 (m, 1H), 2.20-2.43 (m, 4H), 3.32 (m, 2H), 3.44 (dd, 1H), 3.78 (quint, 1H), 3.93 (dd, 1H), 4.09 (quint, 1H), 4.20 (dd, 1H), 4.32 (d, 1H).

EXAMPLE 13

[1R-[1α(αR*,δR*),2α,3α,4α,6β]]-2-[(2,2-Dimethyl-1-oxobutoxy)methyl]-β,δ-dihydroxy-6-methyl-3-[(phenylmethoxy)methyl]-7-oxabicyclo[2.2.1]heptane-1-heptanoic acid, monolithium salt A. 3-Methyl-2-hydroxymethyl furan To a suspension of LiAlH$_4$ (4.80 g, 0.126 mole) in dry Et$_2$O (350 mL) at 0° C. (ice bath) under argon was added dropwise a solution of 3-methyl-2-furoic acid, methyl ester [17.63 g, 0.126 mole, see Organic Synthesis 39, 49 (1959)] in Et$_2$O (30 mL). When the addition was complete, the mixture was allowed to warm to room temperature and stirred for 1 hour. The mixture was again cooled in an ice bath and treated dropwise with water (4.8 mL), 15% NaOH (4.8 mL) and water (14.4 mL). The resulting suspension was filtered through Celite, the filter cake washed thoroughly with Et$_2$O and the combined filtrate evaporated to dryness. The residue was taken up in CH$_2$Cl$_2$, dried over Na$_2$SO$_4$ and evaporated to give the title alcohol (13.14 g, 93%) as a clear, colorless liquid.

TLC (EtOAc-hexane; 1:1) $R_f$=0.42 ($R_f$ of starting methyl ester=0.67).

$^1$H NMR (CDCl$_3$, 60 MHz) δ 2.03 ppm (3H, s), 2.77 (1H, broad t), 4.53 (2H, d), 6.20 (1H, d), 7.30 (1H, d).

B. (3aα,6α,7α,7aβ)-2,3,7,7a-Tetrahydro-1-oxo-4-methyl-3H-3a,6-epoxisobenzofuran-7-carboxylic acid A solution of the Part A alcohol (39.6 g, 0.354 mole) and maleic anhydride (35.26 g, 0.360 mole) in chloroform (180 mL) was stirred at room temperature under argon for 4 days. The precipitated product was filtered off and washed thoroughly with chloroform to give the title lactone-acid (33.91 g) as a white crystalline solid. The mother liquor was treated with charcoal, filtered and concentrated to a volume of ca 150 mL. To this solution was added DMAP (0.830 g, 6.80 mmole) and the mixture stirred at room temperature under argon for an additional 24 hours. The precipitated product was collected, washed thoroughly with chloroform and dried to give an additional 18.98 g of the title lactone-acid (total: 52.89 g, 71%). A sample recrystallized from acetonitrile-benzene had mp 132° C(d).

$^1$H NMR (d$^6$-acetone) δ 1.97 ppm (3H, d), 2.80 (1H, AB d), 3.12 (1H, AB d), 4.50 (1H, AB d), 4.81 (1H, AB d), 5.03 (1H, broad s), 6.09 (1H, t), 10.75 (1H, broad s).

Anal. Calc'd for C$_{10}$H$_{10}$O$_5$: C, 57.14; H, 4.80 Found: C, 57.28; H, 4.71.

C. (3aα,4β,6α,7α,7aβ)-Hexahydro-1-oxo-4-methyl-3H-3a,6-epoxisobenzofuran-7-carboxylic acid A solution of the Part B lactone-acid (20.0 g, 95.2 mmole) in methanol (800 mL) was treated with 5% Pt-C (1.5 g) and hydrogenated on a Parr apparatus at a pressure of 40 psi for 1.5 hours. The catalyst was filtered off through Celite and washed thoroughly with hot methanol to dissolve the crystallized product. The filtrate was evaporated to dryness to give the crude title product (19.45 g) as a white, crystalline solid. $^1$H-NMR (d$^6$-acetone, 270 MHz) shows that the crude product is a 14:1 mixture of endo (1.09 ppm): exo (0.88 ppm)-methyl isomers. The crude product was recrystallized by dissolving in 1000 mL of boiling acetonitrile, concentrating to 600 mL and diluting with 600 mL of benzene. On cooling, the pure endo-isomer (16.22 g, 81%) separated as white crystals, mp 248-251° C.

$^1$H NMR (d$^6$-acetone) δ 1.09 ppm (1H, d), 1.10 (1H, m), 2.15 (2H, m), 3.06 (1H, AB d), 3.45 (1H, AB d), 4.41 (2H, AB q), 4.60 (1H, d).

Anal. Calc'd for C$_{10}$H$_{12}$O$_5$: C, 56.60; H, 5.70 Found: C, 56.58; H, 5.95.

The structure of the title lactone-acid was confirmed by X-ray crystallography.

D. [3aR-(3aα,4β,6α,7α,7aβ)]-Hexahydro-1-oxo-4-methyl-3H-3a,6-epoxisobenzofuran-7-carboxylic acid, (S)-α-methylbenzenemethanamine salt The following procedure was used for the large scale resolution of the Part C lactone-acid. To a solution of the Part C lactone-acid (19.0 g, 89.6 mmole) in acetonitrile (1000 mL) was added S(−) alpha-methylbenzylamine (12.2 mL, 94.8 mmole). The solution was concentrated, diluted with Et$_2$O and precipitated product collected to give 28.644 g of a white solid. The solid was dissolved in hot MeOH (120 mL) and diluted with EtOAc (1000 mL). After standing at room temperature for 3 hours, the crystallized salt was collected to give 19.80 g of the less soluble S(−) amine salt. Concentration of the mother liquor gave 6.810 g of the more soluble S(−) amine salt. The less soluble salt (19.80 g) was dissolved in hot MeOH (100 mL) and diluted with warm EtOAc (1000 mL). After standing at room temperature for 4 hours, the crystallized salt was collected and washed with EtOAc (200 mL) to give 9.980 g of the less soluble S(−) amine salt. Concentration of the mother liquor gave 7.130 g of the more soluble S(−) amine salt. The less soluble salt (9.970 g) was combined with 9.970 g of material prepared in an identical fashion from an additional 19.0 g of racemic Part C acid, dissolved in hot MeOH (110 mL) and diluted with warm EtOAc (1000 mL). After standing at room temperature for 4 hours, the crystallized salt was collected and washed with EtOAc (200 mL) and air dried to give 16.814 g of the pure title less soluble S(−) amine salt (16.814 g, 28% based on the Part C acid) as white needles, mp 180-182° C(d).

[α]$_D$= −1.1° (c=0.54, MeOH).

The optical purity of the title salt can be checked by conversion to the corresponding amide. Thus, to a solution of the title salt (0.015 g 0.045 mmole) in CH$_2$Cl$_2$ (1 mL) at 0° C. under argon was added hydroxybenztriazole hydrate (0.008 g, 0.059 mmole) and 1-ethyl-3-(3-dimethylaminopropyl)carbodiimide hydrochloride (0.011 g, 0.057 mmole). The mixture was allowed to warm to room temperature, stirred for 1 hour and partitioned between CH$_2$Cl$_2$-5% KHSO$_4$. The organic phase was washed with saturated NaHCO$_3$, dried over Na$_2$SO$_4$ and evaporated to dryness to give the amide (0.013 g, 94%) as a white crystalline solid. TLC (MeOH-CH$_2$Cl$_2$-toluene; 1:2:8) single spot $R_f$=0.26.

The S(−) alpha-methylbenzylamineamide prepared in a similar fashion from the racemic Part C acid showed two spots $R_f$'s=0.26 and 0.21 (isomers).

E. [3aR-(3aα,4β,6α,7α,7aβ)]-Hexahydro-1-oxo-4-methyl-3H-3a,6-epoxisobenzofuran-7-carboxylic acid A solution of the Part D salt (18.270 g, 54.9 mmole) in water (150 mL) was passed through an AG50-X8 column (H+form, 200 mL bed volume, 2 inch diameter column) eluting with water. The product containing fractions were combined and lyophilized to give the title acid as a fluffy, white solid. The product was taken up in acetonitrile, evaporated and triturated with Et$_2$O to give the title lactone acid (10.937 g, 94%) as white crystals, mp 252-253° C.

$[α]_D = +38.9°$ (c=0.54, MeOH).

TLC (AcOH-MeOH-CH$_2$Cl$_2$; 1:1:20) R$_f$=0.42.

F. [3aS-(3aα,4β,6α,7β,7aα)]-Hexahydro-7-hydroxymethyl-6-methyl-4,7-epoxisobenzofuran-1(7aH)-one To a suspension of the Part E acid (10.824 g, 51 mmole) in dry CH$_2$Cl$_2$ (160 mL) at 0° C. under argon was added oxalyl chloride (5.60 mL, 64 mmole) and DMF (200 μL). The mixture was allowed to warm to room temperature, stirred for 2 hours and evaporated to dryness. The crude acid chloride was taken up in dry THF (180 mL), cooled in an ice bath and treated with LiAl(OBu$^t$)$_3$H (28.8 g, 113 mmole). After stirring at 0° C. for 45 minutes and at room temperature for 1.5 hours, the mixture was placed in an ice bath and quenched with saturated Na$_2$SO$_4$ solution (25 mL). The mixture was diluted with EtOAc (150 mL), dried over Na$_2$SO$_4$, filtered through Celite and evaporated to dryness. The crude product was purified by flash chromatography on silica gel (180 g, LPS-1) eluting with acetone-hexane (3:7) to give the title alcohol (7.425 g, 73%) as a white, crystalline solid. Trituration of a 55 mg sample with Et$_2$O gave 42 mg of the title alcohol as white crystals, mp 70-71° C.

$[α]_D = -35.1°$ (c=0.53, CHCl$_3$)

TLC (MeOH-CH$_2$Cl$_2$; 1:9) R$_f$=0.56.

G. [3aS-(3aα,4β,6α,7β,7aα)]-7-[[[(1,1-Dimethylethyl)dimethylsilyl]oxy]methyl]hexahydro-6-methyl-4,7-epoxisobenzofuran-1(7aH)-one To a solution of the Part F alcohol (7.370 g, 37.2 mmole) and triethylamine (6.16 mL, 44.5 mmole) in dry CH$_2$Cl$_2$ (50 mL) was added t-butyldimethylsilyl chloride (6.16 g, 40.9 mmole) and DMAP (0.89 g, 7.3 mmole). After stirring at room temperature for 6 hours, the mixture was washed with 5% KHSO$_4$, dried over Na$_2$SO$_4$ and evaporated to dryness. The crude product was purified by flash chromatography on silica gel (150 g LPS-1) eluting with EtOAc-hexane (2:8) to give the title alcohol (11.487 g, 99%) as a colorless oil which crystallized on standing, mp 47-59° C.

$[α]_D = -22.8°$ (c=0.53, CHCl$_3$).

TLC (acetone-Et$_2$O; 1:9) R$_f$=0.62 (R$_f$ of Part F alcohol=0.26).

H. [1R-(1α,3aα,4β,6α,7β,7aα)]-7-[[[(1,1-Dimethylethyl)dimethylsilyl]oxy]methyl]-octahydro-6-methyl-4,7-epoxisobenzofuran-1-ol To a solution of Part G lactone (11.43 g, 36.6 mmole) in dry toluene (100 mL) at −78° C. (dry ice-EtOH bath) under argon was added via syringe 1.5M DiBAL-toluene (27.0 mL, 40.5 mmole). After 2 hours at −78° C., the reaction was quenched by the addition of silica gel (50 g, Merck) and water (15.0 mL) and the mixture allowed to warm to room temperature. After stirring at room temperature for 30 minutes, the mixture was filtered, the silica gel washed thoroughly with EtOAc and the combined filtrate evaporated to dryness. The crude product was purified by flash chromatography on silica gel (120 g, LPS-1) eluting with EtOAc-hexane (3:7) to give the title lactol (11.488 g, 100%) as a colorless oil which crystallized on standing, mp 46-48° C.

$[α]_D = +8.8°$ (c=0.54, CHCl$_3$).

TLC (EtOAc-hexane; 1:1) R$_f$=0.30 (R$_f$ of the Part G lactone=0.43).

I. [1R-(1α,2α,3α,4α,6β)]-1-[[[(1,1-Dimethylethyl)dimethylsilyl]oxy]methyl]-2-ethenyl-6-methyl-7-oxabicyclo[2.2.1]heptane-3-methanol To a suspension of methyl triphenylphosphonium bromide (52.3 g, 146 mmole) in dry THF (380 mL) at −78° C. under argon was added 1.6M n-BuLi-hexane (80.0 mL, 128 mmole) dropwise via syringe. After stirring at −78° C. for 0.75 hour and at 0° C. for 1 hour, a solution of the Part H lactol (11.44 g, 36.4 mmole) in THF (20 mL) was added to the yellow-orange ylide solution and the mixture allowed to warm to room temperature. After stirring at room temperature for 16 hours, the reaction was quenched by the addition of saturated NH$_4$Cl solution (25 mL), dried over Na$_2$SO$_4$, filtered through Celite and evaporated to dryness. The crude product was purified by flash chromatography on silica gel (300 g, LPS-1) eluting with EtOAc-hexane (2:8) to give the title alcohol (10.64 g, 94%) as a colorless oil which crystallized on standing, mp 44-46° C.

$[α]_D = +38.4°$ (c=0.52, CHCl$_3$).

TLC (EtOAc-hexane; 1:1) R$_f$=0.50 (R$_f$ of the Part H lactol=0.34).

J. [1R-(1α,2α,3α,4α,6β)]-1-[[[(1,1-Dimethylethyl)dimethylsilyl]oxy]methyl]-2-ethenyl-6-methyl-3-[(phenylmethoxy)methyl]-7-oxa-bicyclo[2.2.1]heptane To a solution of the Part I alcohol (0.940 g, 3.01 mmole) in dry THF (10 mL) at 0° C. under argon was added 60% NaH-oil dispersion (0.180 g, 4.5 mmole). After stirring at 0° C. for 0.5 hour, benzylbromide (0.55 mL, 4.6 mmole) and tetrabutylammonium iodide (0.085 g) were added, the mixture warmed to room temperature and stirred for 16 hours. The mixture was then partitioned between EtOAc-5% KHSO$_4$ (50 mL each), the organic phase washed with saturated NaHCO$_3$ and saturated NaCl solutions, dried over Na$_2$SO$_4$ and evaporated to dryness. The crude product was purified by flash chromatography on silica gel (80 g, LPS-1) eluting with Et$_2$O-hexane (5:95) to give the title benzyl ether (1.10 g, 91%) as a colorless oil.

TLC (Et$_2$O-hexane; 3:7) R$_f$=0.71.

K. [1R-(1α,2α,3α,4α,6β)]-1-[[[(1,1-Dimethylethyl)dimethylsilyl]oxy]methyl]-6-methyl-3-[(phenylmethoxy)methyl]-7-oxabicyclo[2.2.1]heptane-2-methanol A solution of the part J olefin (1.054 g, 2.62 mmole) in methanol (15 mL) at −78° C. (dry ice-EtOH bath) was treated with ozone until the blue color of excess ozone was observed. Nitrogen was passed through the solution until the blue color was discharged and dimethylsulfide (0.95 mL) was added. After stirring at −78° C. for 1.5 hours and at 0° C. for 2 hours, the mixture was evaporated to dryness to give the crude aldehyde as a colorless oil.

TLC (EtOAc-hexane; 1:1) R$_f$=0.52 (R$_f$ of the Part J olefin=0.61).

The crude aldehyde was taken up in dry THF (20 mL), cooled in an ice bath and treated with LiAl(OBu$^t$)$_3$H (1.66 g, 6.52 mmole) and then allowed to warm to room temperature. After stirring at room temperature for 1 hour, the mixture was placed in an ice bath and quenched with saturated Na$_2$SO$_4$ solution (5 mL). The mixture was diluted with EtOAc (50 mL), dried over Na$_2$SO$_4$, filtered through Celite and evaporated to dryness. The crude product was purified by flash chromatography on silica gel (100 g, LPS-1) eluting with acetone-hexane (5:95) to give title alcohol (0.718 g, 67.5%) as a colorless oil.

TLC (acetone-hexane; 1:9) $R_f$=0.25.

L. [1R-(1α,2α,3α,4α,6β)]-1-[[[(1,1-Dimethylethyl)dimethylsilyl]oxy]methyl]-6-methyl-3-[(phenylmethoxy)methyl]-7-oxabicyclo[2.2.1]heptane-2-methanol, 2,2-dimethylbutanoate To a solution of the Part K alcohol (0.718 g, 1.77 mmole) in dry pyridine (4.0 mL) at room temperature under argon was added 2,2-dimethylbutyryl chloride (0.36 g, 2.67 mmole) and DMAP (0.030 g, 0.25 mmole). After stirring at room temperature for 16 hours, the mixture was evaporated to dryness (30° C., 0.5 mmHg). The residue was taken up in EtOAc and washed successively with 5% KHSO$_4$, saturated NaHCO$_3$ and saturated NaCl, dried over Na$_2$SO$_4$ and evaporated to dryness. The crude product was purified by flash chromatography on silica gel (80 g, LPS-1) eluting with Et$_2$O-hexane (7:93) to give the title ester (0.826 g, 93%) as a colorless oil.

TLC (EtOAc-hexane; 2:8) $R_f$=0.58 ($R_f$ of the Part K alcohol=0.30).

M. [1R-(1α,2α,3α,4α,6β)]-2-[(2,2-Dimethyl-yl-1-oxobutoxy)methyl]-6-methyl-3-[(phenylmethoxy)methyl]-7-oxabicyclo[2.2.1]heptane-1-carboxaldehyde To a solution of the Part L silyl ether (0.826 g, 1.64 mmole) in acetonitrile (8.0 mL) was added 48% aq. HF (0.30 mL, 8.3 mmole). After stirring at room temperature for 45 minutes, the mixture was diluted with EtOAc, washed with saturated NaHCO$_3$ and saturated NaCl solutions, dried over Na$_2$SO$_4$ and evaporated to dryness to give crude alcohol (0.656 g, theory: 0.639 g) as a colorless oil.

TLC (EtOAc-hexane; 1:4) $R_f$=0.10 ($R_f$ of the Part L silyl ether=0.58).

To a solution of Dess-Martin periodinane (1.41 g, 3.33 mmole) and t-butanol (320 μL, 3.39 mmole) in CH$_2$Cl$_2$ (8.0 mL) was added a solution of crude alcohol (0.656 g, theory 0.639 g, 1.64 mmole) in CH$_2$Cl$_2$ (5.0 mL). After stirring at room temperature for 2 hours, the mixture was diluted with CH$_2$Cl$_2$ (20 mL) and poured onto a solution of Na$_2$S$_2$O$_3$ (3.66 g, 23.2 r5 mmole) in 1.0N NaHCO$_3$ solution (30 mL, 30 mmole) and stirred vigorously for 15 minutes. The organic phase was separated, dried over Na$_2$SO$_4$ and evaporated to dryness. The crude product was purified by flash chromatography on silica gel (70 g, LPS-1) eluting with acetone-hexane (5:95) to give aldehyde (0.574 g, 90% overall from the Part L silyl ether) as a colorless oil.

TLC (EtOAc-hexane; 4:6) $R_f$=0.49 ($R_f$ of alcohol=0.25).

N. [1R-[1α(R*,E),2α,3α,4α,6β)]-3-[[[(1,1-Dimethylethyl)dimethylsilyl]oxy]-7-[2-[(2,2-dimethyl-1-oxobutoxy)methyl]-6-methyl-3-[(phenylmethoxy)methyl]-7-oxabicyclo[2.2.1]hept-1-yl]-5-oxo-6-heptenoic acid, methyl ester To a solution of (R)-6-(dimethoxyphosphinyl)-3-[[(1,1-dimethylethyl)dimethylsilyl]oxy]-5-oxohexanoic acid, methyl ester (0.720 g, 1.88 mmole) in dry acetonitrile (8.0 mL) at room temperature under argon was successively added anhydrous LiCl (0.080 g, 1.90 mmole), DBU (250 μL, 1.67 mmole) and a solution of the Part M aldehyde (0.560 g, 1.44 mmole) in dry acetonitrile (2 mL). After 15 minutes, the LiCl had gone into solution and a cloudy precipitate began to form. After stirring at room temperature for 4.5 hours, the mixture was partitioned between EtOAc-5% KHSO$_4$ (50 mL each), the organic phase washed with 5% KHSO$_4$, saturated NaHCO$_3$, and saturated NaCl solutions, dried over Na$_2$SO$_4$ and evaporated to dryness. The crude product was purified by flash chromatography on silica gel (60 g, LPS-1) eluting with Et$_2$O-hexane (1:4) to give the title enone (0.902 g, 97%) as a colorless oil.

TLC (EtOAc-hexane; 3:7) $R_f$=0.52 ($R_f$ of the Part M aldehyde=0.44).

O. [1R-[1α(R*),2α,3α,4α,6β]]-2-[(2,2-Dimethyl-1-oxobutoxy)methyl]-β-hydroxy-δ-oxo-6-methyl-3-[(phenylmethoxy)methyl-7-oxabicyclo[2.2.1]heptane-1-heptanoic acid, methyl ester To a mixture of the Part N enone (0.902 g, 1.40 mmole) and dimethylphenylsilane (0.760 g, 5.59 mmole) was added tris(triphenylphosphine)rhodium chloride (0.016 g, 0.016 mmole) and the resulting mixture heated at 50–55° C. (bath temperature) for 2.5 hours. The excess silane was distilled off at 50° C., 0.5 mmHg.

TLC (EtOAc-hexane; 3:7) shows the silyl enol-ether at $R_f$=0.56 ($R_f$ of Part N enone=0.40).

The crude silyl enol-ether was taken up in acetonitrile (20 mL) and treated with 48% aq. HF (0.25 mL). After stirring at room temperature for 1.5 hours, the mixture was partitioned between EtOAc-saturated NaHCO$_3$ (50 mL each). The organic phase was washed with saturated NaCl solution, dried over Na$_2$SO$_4$ and evaporated to dryness. The crude product was purified by flash chromatography on silica gel (80 g, LPS-1) eluting with EtOAc-hexane (4:6) to give the title keto-alcohol (0.546 g, 73%) as a colorless oil.

TLC (acetone-hexane; 35:65) $R_f$=0.35.

P. [1R-[1α(βR*,δR*),2α,3α,4α,6β]]-2-[(2,2-Dimethyl-1-oxobutoxy)methyl]-β,δ-dihydroxy-6-methyl-3-[(phenylmethoxy)methyl]-7-oxa-bicyclo[2.2.1]heptane-1-heptanoic acid, methyl ester A solution of trimethylacetic acid (0.006 g, 0.06 mmole) in 1.0M triethylborane-THF (1.16 mL, 1.16 mmole) was stirred at room temperature under argon for 1 hour. To this solution was added a solution of the Part O keto-alcohol (0.518 g, 0.97 mmole) in dry THF (8 mL). After stirring at room temperature under argon for an additional 1 hour, the mixture was cooled to −78° C. (dry ice-EtOH bath) and treated successively with NaBH$_4$ (0.115 g, 3.04 mmole) and methanol (2.0 mL, added dropwise). After stirring at −78° C. for 1.5 hours, the solution was treated dropwise with 30% H$_2$O$_2$ (2.3 mL)-water (6.6 mL) and allowed to warm to room temperature. After stirring at room temperature for 30 minutes, the mixture was partitioned between EtOAc-5% KHSO$_4$ (50 mL each). The organic phase was washed with saturated NaHCO$_3$ and saturated NaCl, dried over Na$_2$SO$_4$ and evaporated to dryness. The crude product was purified by flash chromatography on silica gel (60 g, LPS-1) eluting with acetone-hexane (2:8) to give the title diol (0.471 g, 91%) as a colorless oil.

TLC (acetone-hexane; 35:65) $R_f$=0.28 ($R_f$ of the Part O keto-alcohol=0.35).

Q. [1R-[1α(βR*,δR*),2α,3α,4α,6β]]-2-[(2,2-Dimethyl-1-oxobutoxy)methyl]-β,δ-dihydroxy-6-methyl-3-[(phenylmethoxy)methyl]-7-oxabicyclo[2.2.1]heptane-1-heptanoic acid, monolithium salt To a solution of the Part P methyl ester (0.453 g, 0.848 mmole) in dioxane (4.0 mL) was added 1.0N LiOH (0.90 mL, 0.90 mmole) and the resulting solution stirred at room temperature under argon for 1 hour. The solution was then evaporated to dryness and the crude product purified by chromatography on HP-20 (15 mL bed volume, 1 inch diameter column) eluting first with water (300 mL) then with methanol-water (75:25; 500 mL). The product containing fractions were combined and evaporated to dryness. The residue was taken up in water, filtered through a polycarbonate membrane and lyophilized to give the title lithium salt (0.377 g, 84%) as a fluffy, white solid.

TLC (AcOH-MeOH-CH$_2$Cl$_2$; 1:1:20) R$_f$=0.27.

[α]$_D$= +37.1° (c=0.64, MeOH).

Anal. Calc'd for C$_{29}$H$_{43}$O$_8$Li+0.30 H$_2$O: C, 65.48; H, 8.26

Found: C, 65.49; H, 8.24.

The following additional compounds of the invention may be prepared following the procedures set out hereinbefore in the description and working Examples.

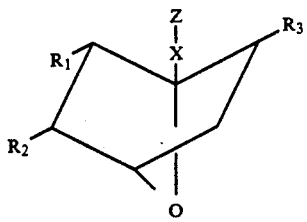

wherein Z is

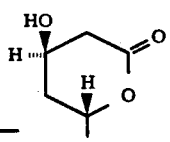

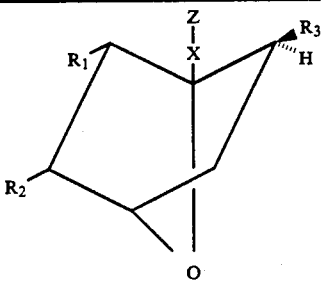

| Ex. No. | Z* | X | R$_1$ | R$_2$ | R$_3$ |
|---|---|---|---|---|---|
| 14 | | CH$_2$CH$_2$ | (CH$_3$)$_2$NC(O)– | CH$_3$OCH$_2$ | H |
| 15 | | CH$_2$CH$_2$ | C$_4$H$_9$ | H | C$_6$H$_5$CH$_2$ |
| 16 | | CH=CH | (C$_2$H$_5$)$_2$NC(O)– | C$_2$H$_5$OCH$_2$ | H |
| 17 | | CH$_2$CH$_2$ | C$_6$H$_5$CH$_2$OCH$_2$ | C$_6$H$_5$CH$_2$OCH$_2$ | CH$_3$ |
| 18 | | CH$_2$CH$_2$ | C$_2$H$_5$C(O)C(CH$_3$)$_2$NCH$_2$–CH$_3$ | C$_2$H$_5$OCH$_2$ | C$_2$H$_5$ |
| 19 | | CH=CH | (C$_2$H$_5$)$_2$NC(O)– | C$_6$H$_5$(CH$_2$)$_2$OCH$_2$ | CH$_3$ |
| 20 | | CH$_2$CH$_2$ | C$_3$H$_7$C(O)C(CH$_3$)$_2$OCH$_2$ | CH$_3$OCH$_2$ | iso-C$_3$H$_7$ |
| 21 | | CH$_2$CH$_2$ | C$_3$H$_7$ | CH$_3$OCH$_2$ | C$_6$H$_5$(CH$_2$)$_2$ |

*as defined hereinbefore

What is claimed is:

1. A compound having the structure

X is —CH$_2$CH$_2$— or —CH=CH—;

R$_1$ is alkyl, arylalkyl, alkanoyloxyalkyl, arylalkyloxyalkyl, alkylaminocarbonyl, dialkylaminocarbonyl, alkanoylaminoalkyl, alkanoyl(alkyl)aminoalkyl, or aralkyl(alkyl)aminocarbonyl;

R$_2$ is H, alkyl, aralkyl, alkoxyalkyl, aralkoxyalkyl, hydroxyalkyl, or alkanoyloxyalkyl; and R$_3$ is H, alkyl or aralkyl.

2. The compound as defined in claim 1 wherein X is —CH=CH—.

3. The compound as defined in claim 1 wherein X is —CH₂CH₂—.

4. The compound as defined in claim 1 wherein R₁ is arylalkyl.

5. The compound as defined in claim 1 wherein R₁ is branched alkanoyloxyalkyl or branched alkanoyl(alkyl)aminoalkyl, R₂ is arylalkyloxyalkyl, R₃ is alkyl and X is CH₂CH₂.

6. The compound as defined in claim 5 wherein R₁ is branched alkanoyloxyalkyl and X is CH₂CH₂.

7. The compound as defined in claim 1 wherein R₁ is alkanoyl(alkyl)aminoalkyl and X is CH₂CH₂.

8. The compound as defined in claim 1 wherein R₁ is arylalkyl(alkyl)aminocarbonyl and X is CH₂CH₂.

9. The compound as defined in claim 1 wherein R₁ is arylalkoxyalkyl.

10. The compound as defined in claim 5 wherein R₁ is

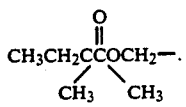

11. The compound as defined in claim 1 wherein R₁ is phenylalkyl, benzyl(alkyl)aminocarbonyl, 1,1-dimethylpropylcarbonyloxymethyl, 1,1-dimethylpropylcarbonyl(alkyl)aminoalkyl or benzyloxymethyl.

12. The compound as defined in claim 1 wherein Z is

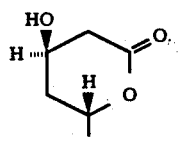

* * * * *

UNITED STATES PATENT AND TRADEMARK OFFICE
CERTIFICATE OF CORRECTION

PATENT NO. : 5,194,634

DATED : March 16, 1993

INVENTOR(S) : Donald S. Karanewsky

It is certified that error appears in the above-identified patent and that said Letters Patent is hereby corrected as shown below:

Claim 1, Column 70, line 67, please change "aikanoyloxyalkyl" to --alkanoyloxyalkyl--.

Signed and Sealed this

First Day of February, 1994

*Attest:*

BRUCE LEHMAN

*Attesting Officer*   Commissioner of Patents and Trademarks